(12) United States Patent
Sakai et al.

(10) Patent No.: US 11,911,108 B2
(45) Date of Patent: Feb. 27, 2024

(54) BLOOD FLOW MEASUREMENT APPARATUS

(71) Applicant: TOPCON CORPORATION, Tokyo (JP)

(72) Inventors: Jun Sakai, Kuki (JP); Shunsuke Nakamura, Kita-ku (JP); Kana Nishikawa, Itabashi-ku (JP); Masahiro Akiba, Wako (JP)

(73) Assignee: TOPCON CORPORATION, Tokyo (JP)

( * ) Notice: Subject to any disclaimer, the term of this patent is extended or adjusted under 35 U.S.C. 154(b) by 793 days.

(21) Appl. No.: 16/966,480

(22) PCT Filed: Dec. 26, 2018

(86) PCT No.: PCT/JP2018/047841
§ 371 (c)(1),
(2) Date: Jul. 31, 2020

(87) PCT Pub. No.: WO2019/150862
PCT Pub. Date: Aug. 8, 2019

(65) Prior Publication Data
US 2021/0038075 A1    Feb. 11, 2021

(30) Foreign Application Priority Data

Jan. 31, 2018 (JP) ................. 2018-014959
Sep. 26, 2018 (JP) ................. 2018-179660

(51) Int. Cl.
*A61B 3/00* (2006.01)
*A61B 3/10* (2006.01)
*A61B 3/12* (2006.01)

(52) U.S. Cl.
CPC .......... *A61B 3/1233* (2013.01); *A61B 3/0033* (2013.01); *A61B 3/102* (2013.01)

(58) Field of Classification Search
CPC ......... A61B 3/102; A61B 3/0025; A61B 3/12; A61B 3/1225; A61B 3/1241; A61B 3/152;
(Continued)

(56) References Cited

U.S. PATENT DOCUMENTS

2007/0222945 A1    9/2007   Tsukada et al.
2010/0118132 A1    5/2010   Yumikake et al.
(Continued)

FOREIGN PATENT DOCUMENTS

CN    101040776 A    9/2007
CN    101156769 A    4/2008
(Continued)

OTHER PUBLICATIONS

International Search Report and Written Opinion dated Mar. 12, 2019 for PCT/JP2018/047841 filed on Dec. 26, 2018, 6 pages including English Translation of the International Search Report.
(Continued)

*Primary Examiner* — Carl H Layno
*Assistant Examiner* — Anh-Khoa N Dinh
(74) *Attorney, Agent, or Firm* — XSENSUS LLP

(57) ABSTRACT

A blood flow measuring unit of a blood flow measurement apparatus of an embodiment includes an optical system for applying an OCT scan to an eye fundus and obtains blood flow information based on data acquired by the OCT scan. A movement mechanism moves the optical system. A controller applies a first movement control to the movement mechanism to move the optical system in a first direction orthogonal to an optical axis of the optical system by a predetermined distance from the optical axis. A judging unit judges occurrence of vignetting based on a detection result of return light of light incident on the eye through the optical system after the first movement control. The controller
(Continued)

applies a second movement control to the movement mechanism to further move the optical system based on a judgement result obtained by the judging unit.

26 Claims, 33 Drawing Sheets

(58) Field of Classification Search
CPC ............. A61B 3/0058; A61B 3/0083; A61B 3/0091; A61B 3/1233; A61B 3/14; A61B 3/0008; A61B 3/0016; A61B 3/0075; A61B 3/02; A61B 3/024; A61B 3/1005; A61B 5/0073; A61B 5/0261; A61B 5/7203; A61B 5/7264; A61B 3/1015; A61B 3/1025; A61B 3/113; A61B 3/117; A61B 3/154; A61B 3/156; A61B 3/16; A61B 3/18; A61B 5/0022; A61B 5/0066; A61B 5/1103; A61B 5/14555; A61B 5/163; A61B 5/7257; A61B 5/7267
See application file for complete search history.

(56) References Cited

U.S. PATENT DOCUMENTS

| | | | |
|---|---|---|---|
| 2012/0274897 A1 | 11/2012 | Narasimha-Lyer et al. | |
| 2013/0010259 A1* | 1/2013 | Carnevale | A61B 3/102 |
| | | | 351/209 |
| 2014/0055748 A1 | 2/2014 | Saito | |
| 2014/0068513 A1 | 3/2014 | Sakagawa | |
| 2014/0111770 A1 | 4/2014 | Ohta et al. | |
| 2015/0085252 A1 | 3/2015 | Fujimura et al. | |
| 2015/0374229 A1 | 12/2015 | Saito | |
| 2016/0287071 A1 | 10/2016 | Tan et al. | |
| 2016/0345822 A1 | 12/2016 | Fujimura et al. | |
| 2017/0258326 A1 | 9/2017 | Sakagawa et al. | |
| 2020/0288976 A1 | 9/2020 | Okuda et al. | |

FOREIGN PATENT DOCUMENTS

| | | |
|---|---|---|
| CN | 101677761 A | 3/2010 |
| CN | 103491858 A | 1/2014 |
| CN | 103654720 A | 3/2014 |
| CN | 103767672 A | 5/2014 |
| EP | 3430975 A1 | 1/2019 |
| JP | 2013-248376 A | 12/2013 |
| JP | 2017-042602 A | 3/2017 |
| JP | 2017-143994 A | 8/2017 |
| JP | 2017-169602 A | 9/2017 |
| WO | 2017/159018 A1 | 9/2017 |

OTHER PUBLICATIONS

Office Action dated Feb. 14, 2023, in corresponding Chinese patent Application No. 201880087949.6, 13 pages.

* cited by examiner

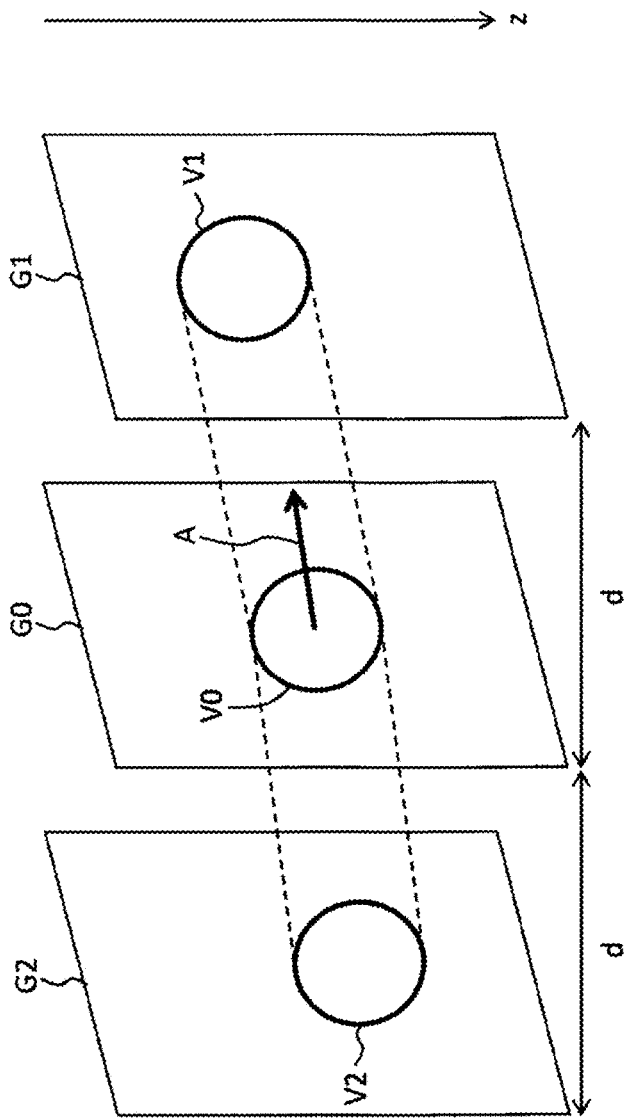

BLOOD FLOW MEASUREMENT APPARATUS

CROSS-REFERENCE TO RELATED APPLICATIONS

This application is a national stage (under 35 U.S.C. 371) of International Patent Application No. PCT/JP2018/047841, filed Dec. 26, 2018, claiming priority to Japanese Patent Application No. 2018-014959, filed Jan. 31, 2018 and Japanese Patent Application No. 2018-179660, filed Sep. 26, 2018, all of which are herein incorporated by reference in their entirety.

FIELD

Technical Field

The present disclosure relates generally to a blood flow measurement apparatus for measuring hemodynamics of an eye fundus.

Art

Researches in the field of ophthalmology have been pursuing development of an apparatus for measuring hemodynamics of an eye fundus using optical coherence tomography (OCT).

In order to obtain optimum Doppler signals for eye fundus blood flow measurement, light needs to be incident in an oblique manner with respect to the blood flow direction (the running direction of the targeted blood vessel). To do so, incident light may be shifted from the optical axis of the eye. As the shift amount increases, light can be made incident more obliquely on the blood vessel while the incident light or its return light becomes more likely to be vignetted at the pupil. Therefore, it is desirable to search for a position where the shift amount becomes maximum in the range where no vignetting at the pupil occurs. If automatically performing such an operation, a method may be considered of gradually increasing the shift amount so that vignetting does not occur. However, this method requires a long time to attain the optimum shift position and would impose a tremendous burden on the subject.

Further, since the incident angle with respect to the blood vessel varies depending on the direction and amount of the shift, optimization of the shift position is required in order to realize an appropriate incident angle with respect to the blood flow direction (running direction of the blood vessel).

PRIOR ART DOCUMENTS

Patent Documents

[PATENT DOCUMENT 1] Japanese Unexamined Patent Application Publication No. 2017-42602

SUMMARY

An object of the disclosure is to optimize the shift position of incident light for eye fundus blood flow measurement.

Another object of the disclosure is to shorten the time required for an operation of optimizing the shift position of incident light for eye fundus blood flow measurement.

A blood flow measurement apparatus according to some example aspects includes a blood flow measuring unit, a movement mechanism, a controller, and a judging unit. The blood flow measuring unit includes an optical system for applying an optical coherence tomography (OCT) scan to a fundus of a subject's eye, and is configured to obtain blood flow information based on data acquired by the OCT scan. The movement mechanism is configured to move the optical system. The controller is configured to apply a first movement control to the movement mechanism to move the optical system in a first direction orthogonal to an optical axis of the optical system by a predetermined distance from the optical axis. The judging unit is configured to judge occurrence of vignetting based on a detection result of return light of light incident on the subject's eye through the optical system after the first movement control. The controller applies a second movement control to the movement mechanism to further move the optical system based on a judgement result obtained by the judging unit.

A blood flow measurement apparatus according to some example aspects includes a scanning optical system, a movement mechanism, an image constructing unit, a direction setting unit, a controller, and a blood flow information acquiring unit. The scanning optical system is configured to apply an optical coherence tomography (OCT) scan to a fundus of a subject's eye. The movement mechanism is configured to move the scanning optical system. The image constructing unit is configured to construct an image from first data acquired by the scanning optical system. The direction setting unit is configured to analyze the image to set a first direction orthogonal to an optical axis of the scanning optical system.

The controller is configured to apply a first movement control to the movement mechanism to move the scanning optical system in the first direction.

The blood flow information acquiring unit is configured to acquire blood flow information from second data acquired by the scanning optical system after the first movement control.

BRIEF DESCRIPTION OF THE DRAWINGS

FIG. 6A is a schematic diagram for describing an example of the operation of the blood flow measurement apparatus according to the embodiment.

DETAILED DESCRIPTION

Blood flow measurement apparatuses according to some exemplary embodiments will be described in detail with reference to the drawings. The blood flow measurement apparatuses of the embodiments are configured to acquire fundus data using OCT and generate information showing hemodynamics (referred to as blood flow information). Any known techniques and/or technologies including the contents disclosed in the documents cited in the present specification may be incorporated into the embodiments.

The following embodiments described blood flow measurement apparatuses capable of measuring the fundus of a living eye using Fourier domain OCT such as swept source OCT. The type of OCT applicable is not limited to swept source OCT, and spectral domain OCT or time domain OCT may be applied, for example. The blood flow measurement apparatuses of the embodiments are configured as an apparatus in which an OCT apparatus and a fundus camera are combined. However, a fundus imaging apparatus other than the fundus camera may be combined with an OCT apparatus. Examples of such a fundus imaging apparatus include a scanning laser ophthalmoscope (SLO), a slit lamp microscope, and an ophthalmic surgical microscope.

First Embodiment

<Configuration>

Figure 1:
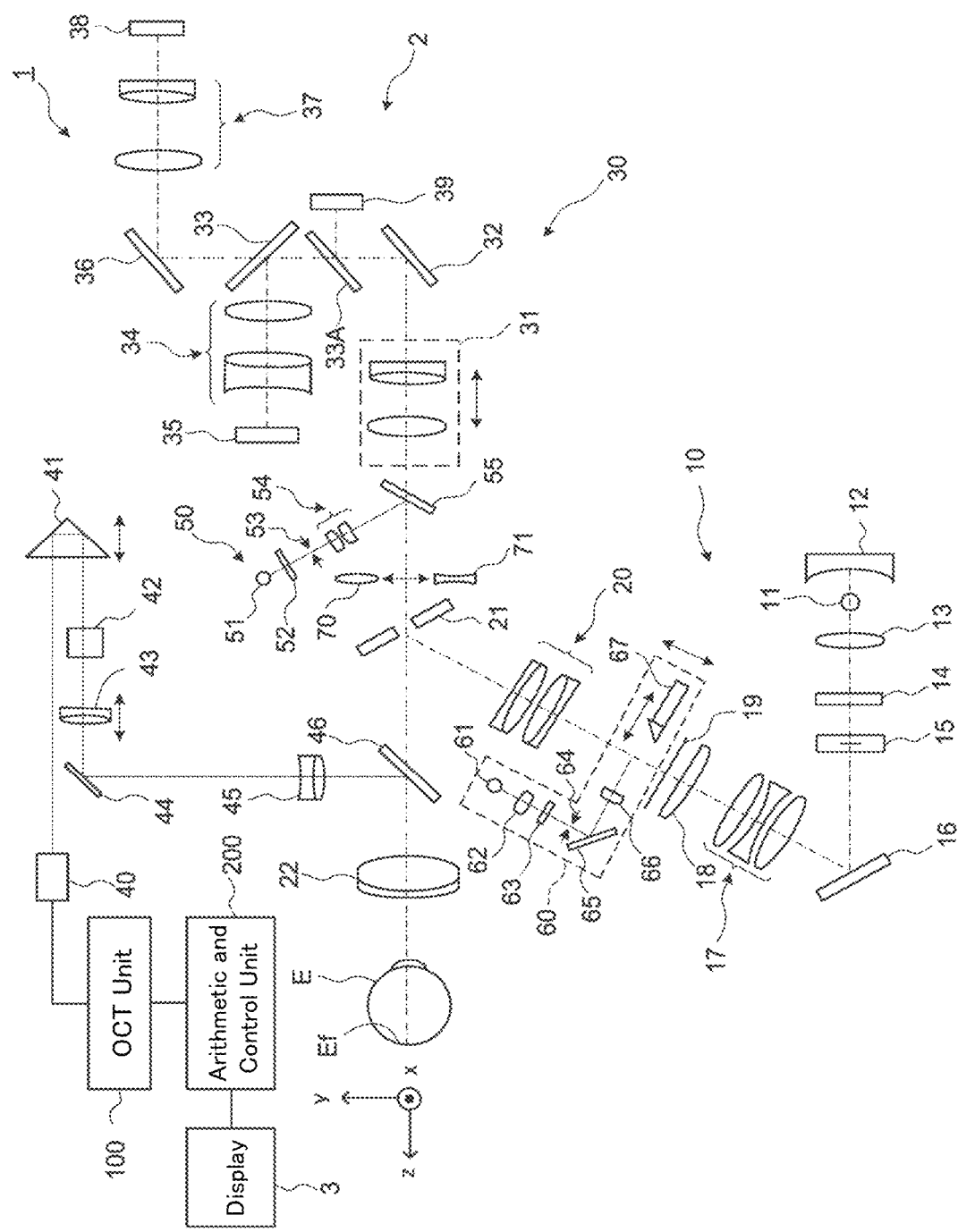
FIG. 1 is a schematic diagram illustrating an example of the configuration of the blood flow measurement apparatus according to the embodiment.

As shown in FIG. 1, the blood flow measurement apparatus 1 includes the fundus camera unit 2, the OCT unit 100 and the arithmetic and control unit 200. The fundus camera unit 2 is provided with an optical system and mechanisms for acquiring front images of the subject's eye. The OCT unit 100 includes part of an optical system and part of mechanisms for performing OCT scanning. Another part of the optical system and another part of the mechanisms for performing OCT scanning are provided in the fundus camera unit 2. The arithmetic and control unit 200 includes one or more processors configured and programmed to execute various calculations and controls. In addition to these, the blood flow measurement apparatus 1 may also include any elements or units such as a member for supporting the face of the subject (e.g., a chin rest, a forehead rest) and a lens unit for switching the sites subjected to OCT scanning (e.g., an attachment for anterior eye segment OCT scanning).

In the present specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The processor realizes the functions according to the embodiment, for example, by reading out and executing a program stored in a storage circuit or a storage device.

<Fundus Camera Unit 2>

The fundus camera unit 2 is provided with an optical system for photographing the fundus Ef of the subject's eye E. Images of the fundus Ef (referred to as fundus images, fundus photographs, or the like) obtained include front images such as observation images and photographed images. An observation image is obtained by capturing a moving image using near-infrared light. A photographed image is a still image obtained by using flash light.

The fundus camera unit 2 includes the illumination optical system 10 and the photographing optical system 30. The illumination optical system 10 projects illumination light onto the subject's eye E. The photographing optical system 30 detects the return light of the illumination light from the subject's eye E. The measurement light incident from the OCT unit 100 is directed to the subject's eye E through the optical path in the fundus camera unit 2, and the return light thereof is directed to the OCT unit 100 through the same optical path.

The light output from the observation light source 11 of the illumination optical system 10 (referred to as observation illumination light) is reflected by the concave mirror 12, passes through the condenser lens 13, and becomes near-infrared light after passing through the visible cut filter 14. Further, the observation illumination light is once converged at a location near the photographing light source 15, reflected by the mirror 16, and passes through the relay lens system 17, the relay lens 18, the diaphragm 19, and the relay lens system 20. Then, the observation illumination light is reflected on the peripheral part (i.e., the surrounding area of the aperture part) of the aperture mirror 21, penetrates the dichroic mirror 46, and refracted by the objective lens 22, thereby illuminating the subject's eye E (the fundus Ef thereof). The return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Furthermore, the return light passes through the half mirror 33A, is reflected by the dichroic mirror 33, and forms an image on the light receiving surface of the image sensor 35 by the condenser lens 34. The image sensor 35 detects the return light at a predetermined frame rate. Note that the focus of the photographing optical system 30 is adjusted to coincide with the fundus Ef or the anterior eye segment.

The light output from the photographing light source 15 (referred to as photographing illumination light) passes through the same route as that of the observation illumination light and is projected onto the fundus Ef. The return light of the photographing illumination light from the subject's eye E passes through the same route as that of the return light of the observation illumination light, is guided to the dichroic mirror 33, passes through the dichroic mirror 33, is reflected by the mirror 36, and forms an image on the light receiving surface of the image sensor 38 by the condenser lens 37.

The liquid crystal display (LCD) 39 displays a fixation target (fixation target image). Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

By changing the display position of the fixation target image on the screen of the LCD 39, the fixation position of the subject's eye E by the fixation target can be changed. Examples of the fixation position includes the followings: a fixation position for acquiring an image centered on the macula; a fixation position for acquiring an image centered on the optic nerve head; a fixation position for acquiring an image centered on the fundus center that is located between the macula and the optic nerve head; and a fixation position for acquiring an image of a site far away from the macula (periphery of the fundus). A user interface such as a graphical user interface (GUI) for designating at least one of such typical fixation positions can be provided. Further, a user interface such as a GUI for manually changing the fixation position (i.e., the display position of the fixation target) can be provided.

The configuration for presenting the fixation target, capable of changing the fixation position, to the subject's eye E is not limited to display devices such as an LCD. For example, a fixation matrix device can be adopted in place of a display device. The fixation matrix device includes a plurality of light emitting parts (e.g., light emitting diodes) that are disposed in a matrix-like arrangement (in a matrix array). In this case, the fixation position of the subject's eye E by the fixation target can be changed by lighting one (or more) of the plurality of light emitting parts in a selective manner. As another example, the fixation target usable for fixation position change may be generated by employing one or more movable light emitting parts.

The alignment optical system 50 generates an alignment indicator used for the alignment of the optical system with respect to the subject's eye E. The alignment light output from the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. The return light of the alignment light from the subject's eye E (e.g., the cornea reflection light) passes through the same route as that of the return light of the observation illumination light and is guided to the image sensor 35. Based on the received image, manual alignment and/or automatic alignment can be performed. The received image is referred to as an alignment indicator image.

As in a conventional case, the alignment indicator image of the present example includes two bright spot images whose positions change according to the alignment state. When the relative position between the subject's eye E and the optical system changes in the xy direction, the two bright spot images are shifted in the xy direction in an integrated manner. When the relative position between the subject's eye E and the optical system changes in the z direction, the relative position (distance) between the two bright spot images changes. When the distance between the subject's eye E and the optical system in the z direction matches with a working distance set in advance, the two bright spot images overlap with each other. When the position of the subject's eye E matches with the position of the optical system in the xy direction, the two bright spot images are presented within or near a given alignment target. When the distance between the subject's eye E and the optical system in the z direction matches with the working distance, and the position of the subject's eye E matches with the position of the optical system in the xy direction, the two bright spot images overlap with each other and are presented within the alignment target.

For the automatic alignment, the data processor 230 detects the positions of the two bright spot images, and the main controller 211 controls the movement mechanism 150 (described later) on the basis of the positional relationship between the two bright spot images and the alignment target. In the manual alignment, the main controller 211 displays the two bright spot images together with the observation image of the subject's eye E on the display 241, and the user operates the movement mechanism 150 using the operation device 242 while referring to the two bright spot images displayed.

The focus optical system 60 generates a split indicator used for the focus adjustment with respect to the subject's eye E. In conjunction with the movement of the photography focusing lens 31 along the optical path of the photographing optical system 30 (referred to as the photographing optical path), the focus optical system 60 is moved along the optical path of the illumination optical system 10 (referred to as the illumination optical path). The reflection rod 67 is inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64. The focus light, then, is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. The return light of the focus light from the subject's eye E (the fundus reflection light, etc.) passes through the same route as that of the return light of the alignment light and is guided to the image sensor 35. Based on the received image, manual focusing and/or automatic focusing can be performed. The received image is referred to as a split indicator image.

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT scanning (measurement arm). The dichroic mirror 46 reflects the light of wavelength bands used for OCT scanning and transmits the light for fundus photography. Listed from the OCT unit 100 side, the collimator lens unit 40, the retroreflector 41, the dispersion compensation member 42, the OCT focusing lens 43, the optical scanner 44, and the relay lens 45 are arranged in the measurement arm.

The retroreflector 41 is movable in the directions indicated by the arrow in FIG. 1, whereby the length of the measurement arm is changed. The change in the optical path length of the measurement arm may be utilized for correcting the optical path length according to the axial length, and for adjusting the interference condition, for example.

Together with the dispersion compensation member 113 (described later) arranged in the reference arm, the dispersion compensation member 42 acts to equalize the dispersion characteristics of the measurement light LS and the dispersion characteristics of the reference light LR with each other.

The OCT focusing lens 43 is moved along the measurement arm in order to perform the focus adjustment of the measurement arm. The movement of the photography focusing lens 31, the movement of the focus optical system 60, and the movement of the OCT focusing lens 43 may be controlled in an interlocking manner.

The optical scanner 44 is placed substantially at a position optically conjugate with the pupil of the subject's eye E. The optical scanner 44 deflects the measurement light LS guided through the measurement arm. The optical scanner 44 is, for example, a galvanometer scanner capable of two dimensional scanning.

<OCT Unit 100>

Figure 2:
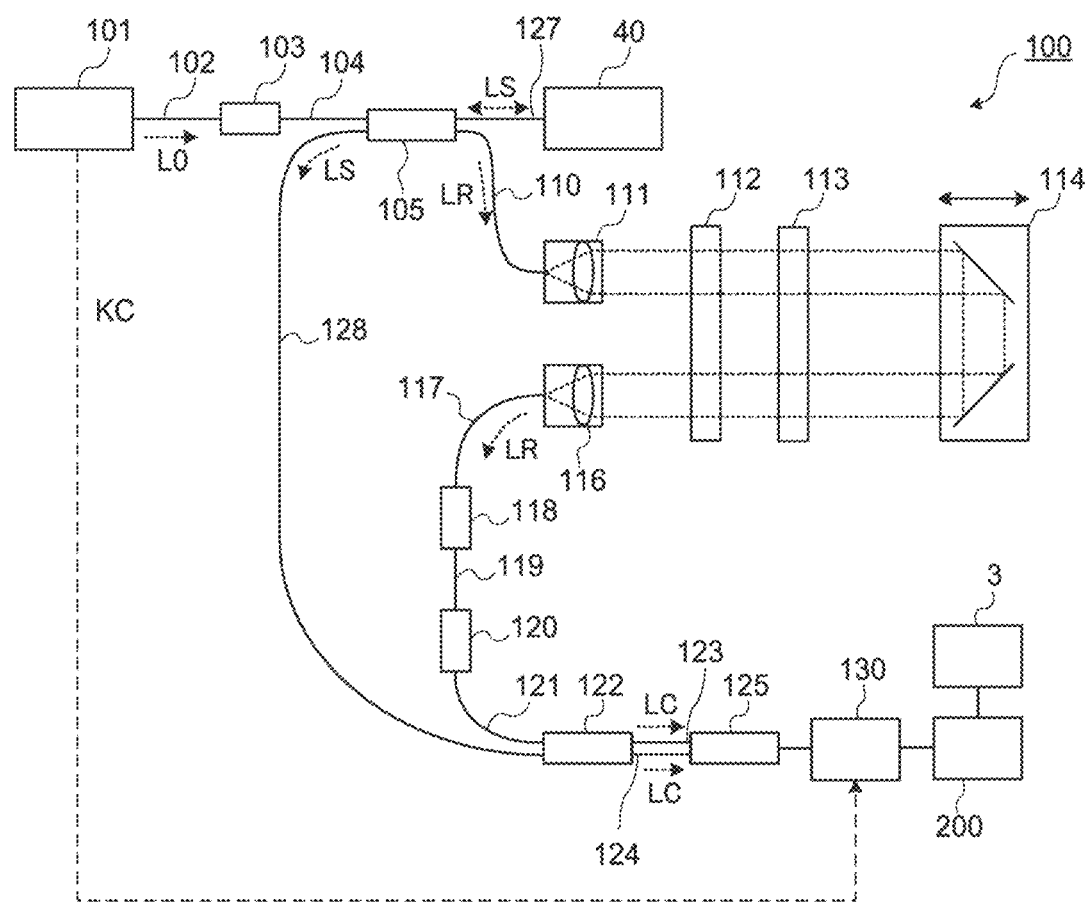
FIG. 2 is a schematic diagram illustrating an example of the configuration of the blood flow measurement apparatus according to the embodiment.

As illustrated in FIG. 2, the OCT unit 100 is provided with the optical system for performing swept source OCT. The optical system includes an interference optical system. The interference optical system is configured to split the light emitted from the light source of wavelength tunable type (or wavelength sweeping type) into measurement light and reference light, superpose the return light of the measurement light from the subject's eye E and the reference light having traveled through the reference optical path to generate interference light, and detect the interference light. The detection result (i.e., detection signal) obtained by the interference optical system is a signal representing a spectrum of the interference light. The detection signal is sent to the arithmetic and control unit 200.

The light source unit 101 includes, for example, a near infrared tunable laser configured to change the wavelengths of emitted light at high speed. The light L0 output from the light source unit 101 is guided to the polarization controller 103 through the optical fiber 102, and the polarization state of the light L0 is regulated. Further, the light L0 is guided to the fiber coupler 105 through the optical fiber 104 and is split into the measurement light LS and the reference light LR. The optical path of the measurement light LS is referred to as a measurement arm, a sample arm, or the like, and the optical path of the reference light LR is referred to as a reference arm or the like.

The reference light LR is guided through the optical fiber 110 to the collimator 111, is converted into a parallel light beam, travels through the optical path length correction member 112 and the dispersion compensation member 113, and is guided to the retroreflector 114. The optical path length correction member 112 acts to match the optical path length of the reference light LR and the optical path length of the measurement light LS with each other. The dispersion compensation member 113 acts to equalize the dispersion characteristics of the reference light LR and the dispersion characteristics of the measurement light LS with each other, together with the dispersion compensation member 42 arranged in the measurement arm. The retroreflector 114 is movable along the optical path of the reference light LR incident on the retroreflector 114. With this, the length of the reference arm is changed. The change in the optical path length of the reference arm can be utilized, for example, for the correction of the optical path length according to the axial length, and for the regulation of the interference condition.

The reference light LR that has passed through the retroreflector 114 travels through the dispersion compensation member 113 and the optical path length correction member 112, is converted from a parallel light beam to a convergent light beam by the collimator 116, and is incident on the optical fiber 117. The reference light LR incident on the optical fiber 117 is guided to the polarization controller 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided through the optical fiber 127 and is converted to a parallel light beam by the collimator lens unit 40. Then, the measurement light LS passes through the retroreflector 41, the dispersion compensation member 42, the OCT focusing lens 43, the optical scanner 44, and the relay lens 45, and then reaches the dichroic mirror 46. The measurement light LS is reflected by the dichroic mirror 46, is refracted by the objective lens 22, and is projected onto the subject's eye E. The measurement light LS is reflected and scattered at various depth positions of the subject's eye E. The return light of the measurement light LS from the subject's eye E travels along the same route as the outward way in the opposite direction, is directed to the fiber coupler 105, and then reaches the fiber coupler 122 via the optical fiber 128.

The fiber coupler 122 superposes the measurement light LS incident through the optical fiber 128 and the reference light LR incident through the optical fiber 121 with each other, to generate interference light. The fiber coupler 122 splits the generated interference light at a predetermined splitting ratio (e.g., 1 to 1) to generate a pair of interference light LC. The pair of the interference light LC is guided to the detector 125 through the optical fibers 123 and 124, respectively.

The detector 125 includes, for example, a balanced photo diode. The balanced photodiode includes a pair of photodetectors for respectively detecting the pair of the interference light LC. The balanced photodiode outputs the difference between the pair of detection results obtained by the pair of photodetectors. The detector 125 sends the output (i.e., detection signal) to the data acquisition system (DAQ) 130.

The clock KC is supplied from the light source unit 101 to the data acquisition system 130. The clock KC is generated in the light source unit 101 in synchronization with the output timings of the respective wavelengths varied within a predetermined wavelength range by the wavelength tunable type light source. For example, the light source unit 101 splits the light L0 of each output wavelength to generate two pieces of split light, optically delays one of the two pieces of split light, combines the two pieces of split light, detects the combined light obtained, and generates the clock KC based on the result of the detection of the combined light. The data acquisition system 130 performs the sampling of the detection signal input from the detector 125 based on the clock KC. The data acquisition system 130 sends the result of the sampling of the detection signal from the detector 125 to the arithmetic and control unit 200.

The present example is provided with both an element for changing the optical path length of the measurement arm (e.g., the retroreflector 41) and an element for changing the optical path length of the reference arm (e.g., the retroreflector 114 or a reference mirror). However, only one of these elements may be provided in other embodiments. Elements for changing the difference between the optical path length of the measurement arm and the optical path length of the reference arm (i.e., elements for changing the optical path length difference) are not limited to the aforesaid elements, and may be any type of element such as any type of optical members and any type of mechanisms.

<Control System>

Figure 3:
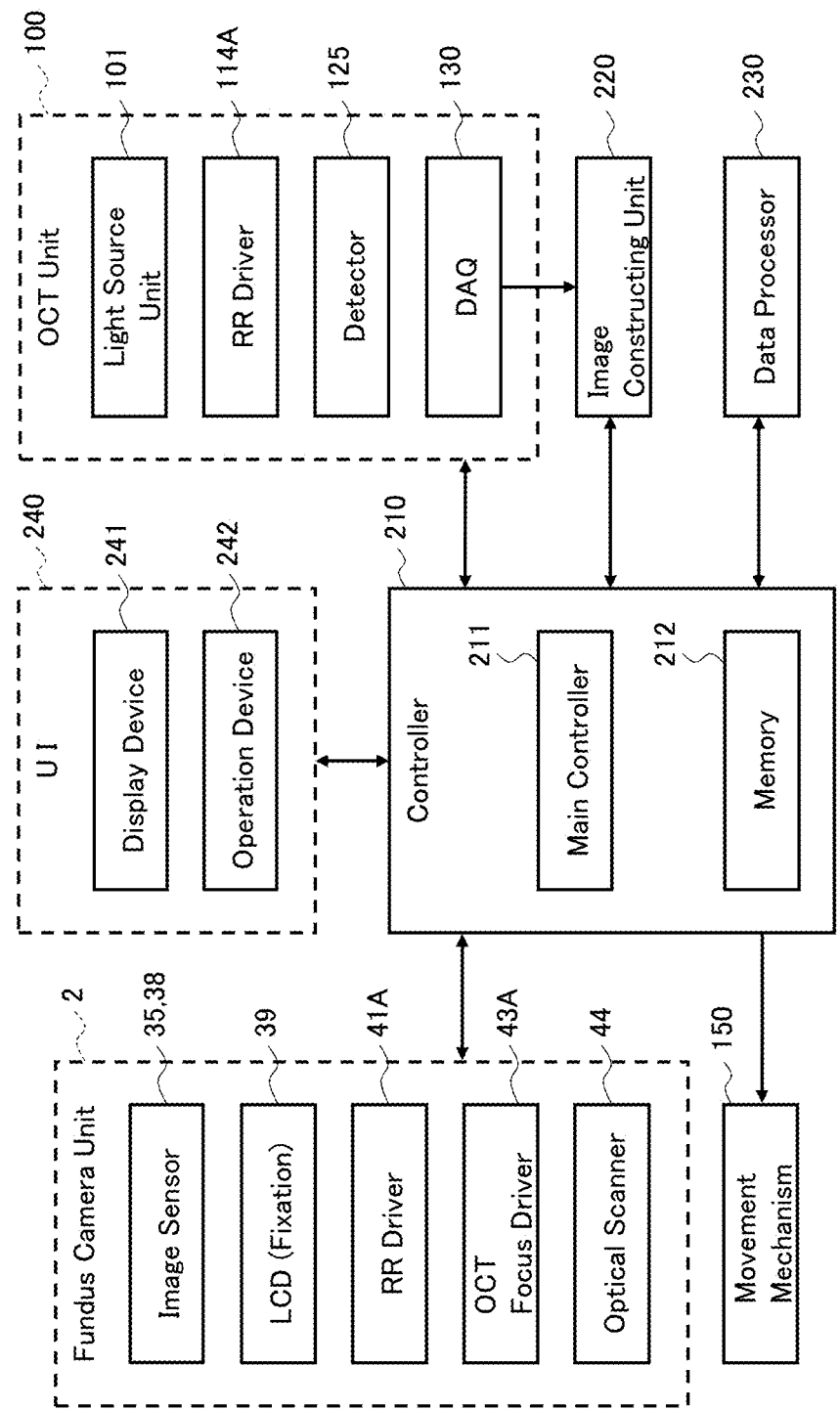
FIG. 3 is a schematic diagram illustrating an example of the configuration of the blood flow measurement apparatus according to the embodiment.
Figure 4:
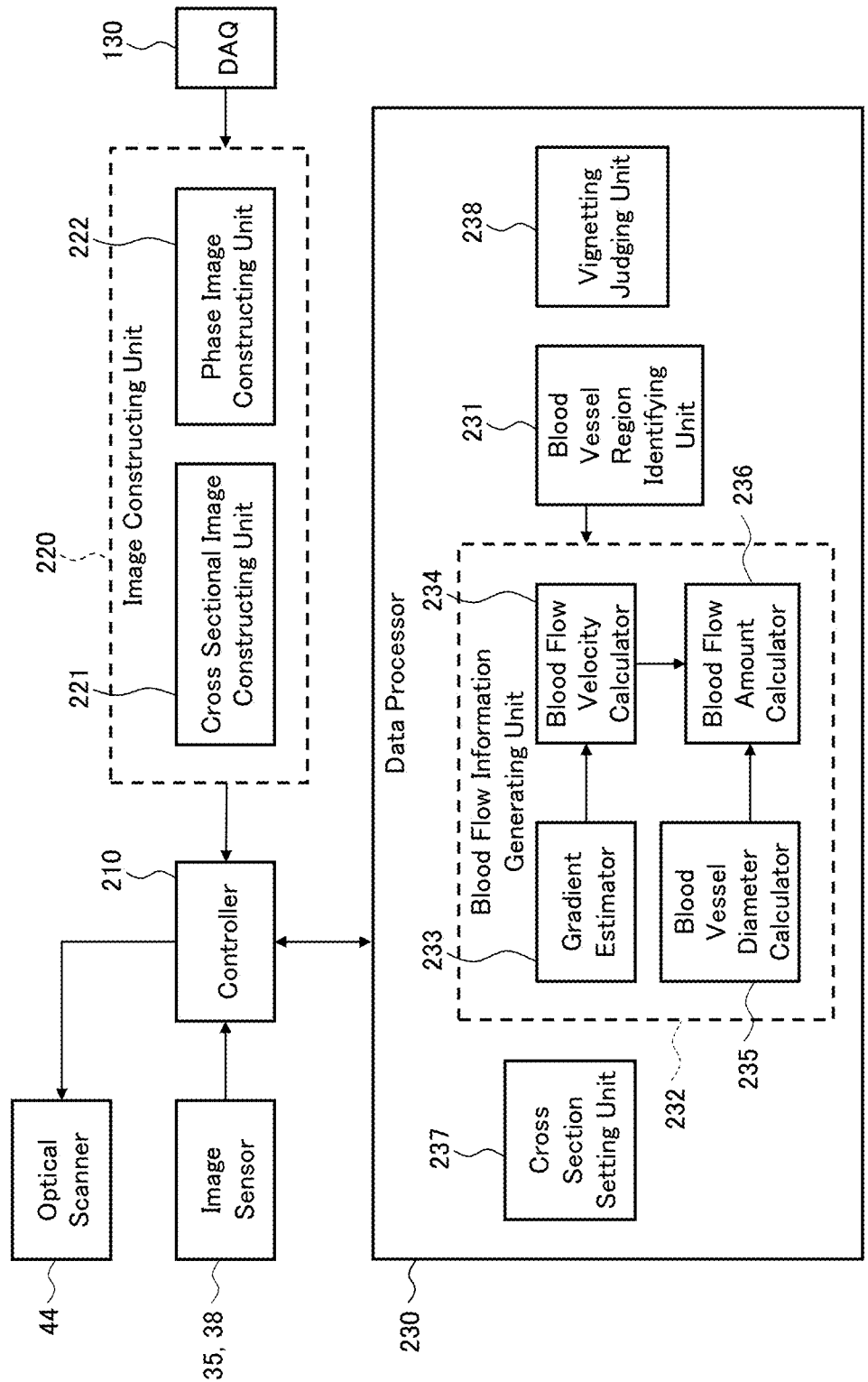
FIG. 4 is a schematic diagram illustrating an example of the configuration of the blood flow measurement apparatus according to the embodiment.

FIG. 3 and FIG. 4 show an example of the configuration of the control system of the blood flow measurement apparatus 1. The controller 210, the image constructing unit 220 and the data processor 230 are provided in the arithmetic and control unit 200.

<Controller 210>

The controller 210 performs various kinds of controls. The controller 210 includes the main controller 211 and the memory 212.

<Main Controller 211>

The main controller 211 includes a processor and controls each unit and element of the blood flow measurement apparatus 1 (including the units and elements shown in FIG. 1 to FIG. 4).

The photography focusing lens 31 disposed in the photographing optical path and the focus optical system 60 disposed in the illumination optical path are moved in a synchronized manner by a photographing focus driver (not shown in the figures) under the control of the main controller 211. The retroreflector 41 disposed in the measurement arm is moved by the retroreflector driver (RR driver) 41A under the control of the main controller 211. The OCT focusing lens 43 disposed in the measurement arm is moved by the OCT focus driver 43A under the control of the main controller 211. The optical scanner 44 disposed in the measurement arm operates under the control of the main controller 211. The retroreflector 114 disposed in the reference arm is moved by the retroreflector driver (RR driver) 114A under the control of the main controller 211. Each of the aforesaid drivers includes an actuator such as a pulse motor which operates under the control of the main controller 211.

The movement mechanism 150 moves, for example, at least the fundus camera unit 2 in a three dimensional manner. In a typical example, the movement mechanism 150 includes the followings: an x stage movable in the ±x direction (i.e., left and right direction); an x movement mechanism that moves the x stage; a y stage movable in the ±y direction (i.e., up and down direction); a y movement mechanism that moves the y stage; a z stage movable in the ±z direction (i.e., depth direction); and a z movement mechanism that moves the z stage. Each of the aforesaid movement mechanisms includes an actuator such as a pulse motor which operates under the control of the main controller 211.

The main controller 211 controls the LCD 39. For example, the main controller 211 displays the fixation target at a preset position on the screen of the LCD 39. Further, the main controller 211 may change the display position of the fixation target displayed on the LCD 39. That is, the main controller 211 may change the fixation position. The fixation target movement may be performed in any manner such as continuous movement, intermittent movement, and discrete movement. Some examples of manners of moving the fixation position in the present embodiment will be described later.

The fixation position is represented by the display position (the pixel coordinates) of the fixation target image on the LCD 39, for example. The pixel coordinates are defined, for example, by using coordinates represented by a two dimensional coordinate system predefined on the display screen of the LCD 39. If the aforementioned fixation matrix device is used, the fixation position is represented, for example, by the position (coordinates) of the light emitting part lit for fixation. The coordinates of that light emitting part are, for example, the coordinates represented by a two dimensional coordinate system defined in advance on the plane on which the plurality of light emitting parts are arranged.

<Memory 212>

The memory 212 stores various kinds of data. Examples of the data stored in the memory 212 include OCT images, fundus images, and subject's eye information. The subject's eye information includes subject information such as the patient ID and the patient's name, identification information for the left eye and the right eye, and electronic medical record information.

<Image Constructing Unit 220>

The image constructing unit 220 constructs OCT image data of the fundus Ef based on the signal (sampling data, or sampled data) input from the data acquisition system 130. The image constructing unit 220 may construct B-scan image data (i.e., two dimensional cross sectional image data) and phase image data of the fundus Ef. These pieces of OCT image data will be described later. The image constructing unit 220 includes, for example, a circuit board and/or a microprocessor. In the present specification, "image data" and an "image" displayed or rendered based thereon may not be distinguished from one another unless otherwise mentioned.

The blood flow measurement of the present embodiment performs two types of scans on the fundus Ef. The two types of scans will be referred to as a main scan and a supplementary scan.

The main scan performs repetitive scanning (iterative scanning), with the measurement light LS, on a cross section of the fundus Ef that intersects a blood vessel of interest in order to acquire phase image data. The cross section of the fundus Ef that intersects a blood vessel of interest is referred to as a cross section of interest.

The supplementary scan performs scanning on a predetermined cross section with the measurement light LS in order to estimate the gradient (or, inclination, tilt, slope, slant, or the like) of the blood vessel of interest at the cross section of interest. The cross section to which the supplementary scan is applied is referred to as a supplementary cross section. In some examples, the supplementary cross section may be a cross section that intersects the blood vessel of interest and is located in the vicinity of the cross section of interest. Such a supplementary cross section is referred to as the first supplementary cross section. In some other examples, the supplementary cross section may be a cross section that intersects the cross section of interest and is oriented along the blood vessel of interest. Such a supplementary cross section is referred to as the second supplementary cross section.

Figure 5A:
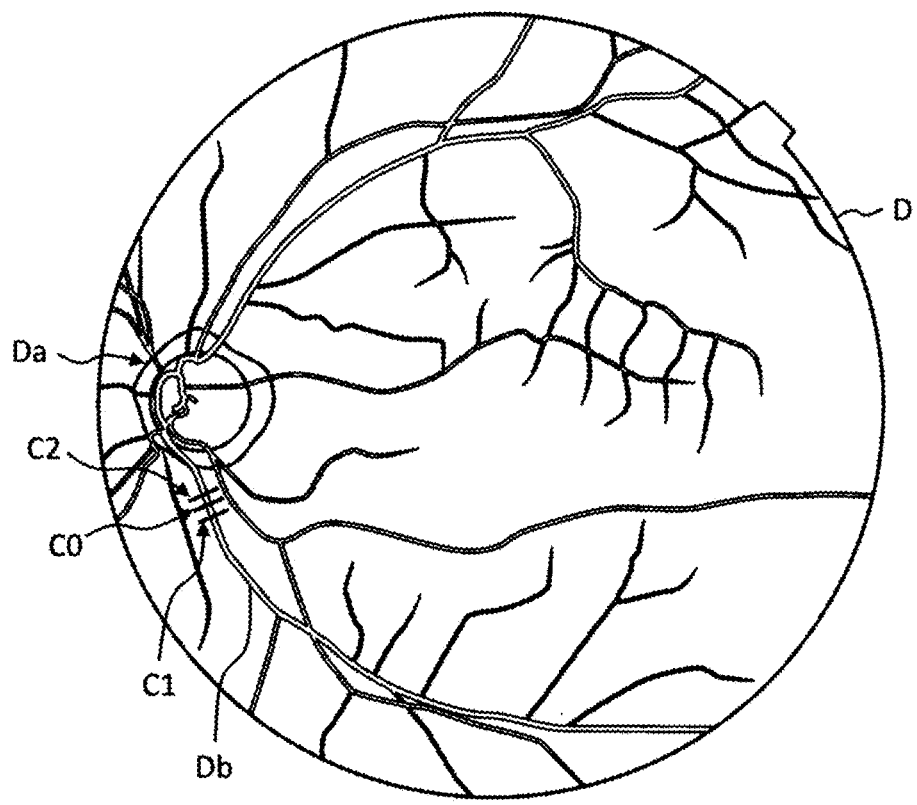
FIG. 5A is a schematic diagram for describing an example of the operation of the blood flow measurement apparatus according to the embodiment.

FIG. 5A shows an example in which the first supplementary cross section is employed. In the present example, as shown on the fundus image D, one cross section of interest C0 and two supplementary cross sections C1 and C2 are set to intersect the blood vessel of interest db. Here, the cross section of interest C0 is located near the optic nerve head Da of the fundus Ef, and the supplementary cross sections C1 and C2 are located near the cross section of interest C0. One of the two supplementary cross sections C1 and C2 is located on the upstream side of the blood vessel of interest db with respect to the cross section of interest C0, and the other is located on the downstream side. The cross section of interest C0 and the supplementary cross sections C1 and C2 are each oriented to be substantially orthogonal to the running direction of the blood vessel of interest db, for example.

Figure 5B:
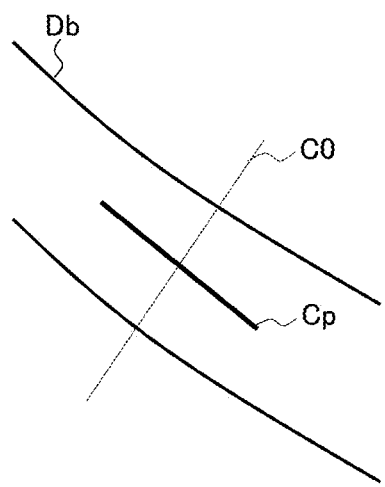
FIG. 5B is a schematic diagram for describing an example of the operation of the blood flow measurement apparatus according to the embodiment.

FIG. 5B shows an example in which the second supplementary cross section is employed. Similar to the above example shown in FIG. 5A, the cross section of interest C0 is set to be substantially orthogonal to the blood vessel of interest db in the present example. Further, in the present example, the supplementary cross section Cp is set to be substantially orthogonal to the cross section of interest C0. The supplementary cross section Cp is oriented along the blood vessel of interest db. As an example, the supplementary cross section Cp may be set to pass through the intersection between the central line of the blood vessel of interest db and the cross section of interest C0.

In the exemplary blood flow measurement, the main scan performs repetitive scanning over a period of time containing at least one cardiac cycle of the patient's heart. This makes it possible to obtain hemodynamics information for all cardiac phases. The period of time during which the main scan is performed may be a fixed length of time set in advance, or a length of time set for a target patient or an examination to be conducted. In the former case (fixed length of time), a period of time longer than the standard cardiac cycle is set (e.g., 2 seconds). In the latter case (non-fixed length of time), biometric data (medical parameters) such as the patient's electrocardiogram may be referred to. Here, any factor other than cardiac cycles may be considered. Examples of such factors include the length of time required for conduction of examination (e.g., burden on patients), the response time of the optical scanner 44 (e.g., scanning time interval), the response time of the detector 125 (e.g., scanning time interval), and the like.

The image constructing unit 220 includes the cross sectional image constructing unit 221 and the phase image constructing unit 222.

<Cross Sectional Image Constructing Unit 221>

The cross sectional image constructing unit 221 constructs cross sectional images that represent a temporal change (or, temporal variation, chronological change, chronological variation, time course, or the like) in the morphology (or structure) of the cross section of interest, based on sampling data obtained by the data acquisition system 130 with the main scan. Such a cross sectional image is referred to as a main cross sectional image. This cross sectional image construction process will be described in more detail. As described above, the main scan performs repetitive scanning on the cross section of interest C0. Sampling data is sequentially input from the data acquisition system 130 to the cross sectional image constructing unit 221 in response to the repetition of scans. The cross sectional image constructing unit 221 constructs one main cross sectional image corresponding to the cross section of interest C0, based on the sampling data corresponding to one scan performed on the cross section of interest C0. The cross sectional image constructing unit 221 repeats such processing as many times as the number of repetition of scans in the main scan, to construct a series of main cross sectional images in time series. Here, these main cross sectional images may be put into a plurality of groups, and then two or more main cross sectional images belonging to one group may be synthesized or composed to create an image having an improved image quality. Such processes are referred to as image averaging.

Further, the cross sectional image constructing unit 221 constructs a cross sectional image that represents the morphology (or structure) of the supplementary cross section, based on sampling data obtained by the data acquisition system 130 with the supplementary scan for the supplementary cross section(s). Such a cross sectional image is referred to as a supplementary cross sectional image. The supplementary cross sectional image constructing process may be executed in the same manner as the main cross sectional image constructing process described above. Here, the main cross sectional image is a series of cross sectional images in time series, but the supplementary cross sectional image may be one cross sectional image. Further, the supplementary cross sectional image may be an image having an improved image quality created by synthesizing or composing a plurality of cross sectional images acquired by a plurality of scans on the supplementary cross section (image averaging).

When the supplementary cross sections C1 and C2 illustrated in FIG. 5A are employed, the cross sectional image constructing unit 221 constructs a supplementary cross sectional image corresponding to the supplementary cross section C1 and a supplementary cross sectional image corresponding to the supplementary cross section C2. On the other hand, when the supplementary cross section Cp illustrated in FIG. 5B is employed, the cross sectional image constructing unit 221 constructs a supplementary cross sectional image corresponding to the supplementary cross section Cp.

The process of constructing a cross sectional image as described thus far includes noise elimination (noise reduction), filtering, and fast Fourier transform (FFT), as in conventional Fourier domain OCT. In the cases where an OCT apparatus of another type is employed, the cross sectional image constructing unit 221 executes a known process according to the type of OCT apparatus employed.

<Phase Image Constructing Unit 222>

The phase image constructing unit 222 constructs a phase image that represents a temporal change (or, temporal variation, chronological change, chronological variation, time course, or the like) in the phase differences in the cross section of interest, based on sampling data obtained by the data acquisition system 130 with the main scan. The sampling data used for constructing the phase image may be the same as the sampling data used for constructing the main cross sectional image by the cross sectional image constructing unit 221. Doing so makes it possible to perform registration between the main cross sectional image and the phase image. In other words, a natural correspondence may be defined between the pixels of the main cross sectional image and the pixels of the phase image.

An example will be described of a method of constructing such phase images. A phase image in the present example is obtained by calculating the phase difference between adjacent A-line complex signals (that is, signals corresponding to mutually adjacent scan points). In other words, the phase image in the present example is constructed based on the temporal change in the pixel values (brightness values) of the main cross sectional image. For an arbitrary pixel of the main cross sectional image, the phase image constructing unit 222 creates a graph of the temporal change in the brightness value of that pixel. The phase image constructing unit 222 determines the phase difference $\Delta\varphi$ between two time points t1 and t2 separated by a predetermined time interval $\Delta t$ in the graph created (t2=t1+$\Delta t$). Then, the phase difference $\Delta\varphi$ is defined as the phase difference $\Delta\varphi$ (t1) at the time point t1. More generally, the phase difference $\Delta\varphi$ may be defined as the phase difference at an arbitrary time point between the time points t1 and t2. By performing this process for each of a large number of time points set in advance, a temporal change in the phase difference for that pixel is obtained.

A phase image is an image representation of phase difference values of each pixel at each time point. This imaging process may be realized, for example, by representing the values of the phase difference with display colors or brightness. When applying such image representation, a display color indicating that a phase has increased in time series may be different from a display color indicating that a phase has decreased in time series. For example, red is assigned to phase increase, and blue is assigned to phase decrease. Further, the magnitude of the amount of change in a phase may be represented by the density of display colors. By adopting representation methods as described above, the direction and quantity of blood flow may be clearly indicated using display colors. A phase image is constructed by executing the above processing for each pixel.

Note that the temporal change in phase difference may be obtained by sufficiently reducing the time interval $\Delta t$ described above to secure the correlation in phases. Here, oversampling may be performed in which the time interval $\Delta t$ is set to a value less than the time period corresponding to the resolution of a cross sectional image in the scanning of the measurement light LS.

<Data Processor 230>

The data processor 230 performs various kinds of data processing. For example, the data processor 230 applies various kinds of image processing and/or various kinds of analysis processing, to an image constructed by the image constructing unit 220. As a specific example, the data processor 230 executes various kinds of correction processing such as brightness correction of an image and/or dispersion correction of an image. Further, the data processor 230 may perform various kinds of image processing and/or various kinds of analysis processing, on an image obtained by the fundus camera unit 2 (e.g., a fundus image, an anterior eye segment image), an image input from the outside, or other images.

The data processor 230 may construct three dimensional image data of the fundus Ef. Three dimensional image data means image data in which the positions of pixels are defined using a three dimensional coordinate system. Stack data and volume data are examples of such three dimensional image data.

Stack data is image data constructed by arranging a plurality of cross sectional images respectively obtained for a plurality of scan lines in a three dimensional fashion, based on the positional relationship of the scan lines. In other words, stack data is image data constructed by representing a plurality of cross sectional images, which are originally defined using mutually different two dimensional coordinate systems, using a common three dimensional coordinate system. In further other words, stack data is image data constructed by embedding such a plurality of cross sectional images in a common three dimensional space.

Volume data is image data whose picture elements are voxels that are arranged in a three dimensional manner. Volume data is also referred to as voxel data. Volume data is constructed by applying known interpolation, voxelization, or the like, to stack data.

The data processor 230 may construct an image to be displayed, by applying rendering to three dimensional image data. Examples of applicable rendering methods and techniques include volume rendering, surface rendering, maximum intensity projection (MIP), minimum intensity projection (MinIP), and multi planar reconstruction (MPR).

The data processor 230 includes the following exemplary elements for obtaining blood flow information: the blood vessel region identifying unit 231, the blood flow information generating unit 232, the cross section setting unit 237, and the vignetting judging unit 238. The blood flow information generating unit 232 includes the gradient estimator 233, the blood flow velocity calculator 234, the blood vessel diameter calculator 235, and the blood flow amount calculator 236.

<Blood Vessel Region Identifying Unit 231>

For each of the main cross sectional image, the supplementary cross sectional image, and the phase image, the blood vessel region identifying unit 231 identifies a blood vessel region in that image corresponding to the blood vessel of interest db. This processing may be performed by analyzing the pixel values of the image (e.g., thresholding).

Note that although the main cross sectional image and the supplementary cross sectional image have sufficient resolution to be subjected to analysis processing, the phase image may not have resolution enough to identify the boundary of a blood vessel region in some cases. However, since blood flow information is generated based on the phase image, it is necessary to identify a blood vessel region included therein with high precision and high accuracy. To do so, for example, the following processes may be employed to more accurately identify a blood vessel region in the phase image.

As described above, the main cross sectional image and the phase image are constructed from the same sampling data. Therefore, a natural correspondence between the pixels of the main cross sectional image and the pixels of the phase image may be established. For example, the blood vessel region identifying unit 231 may be configured to perform the following processes to identify a blood vessel region in the phase image: analyzing the main cross sectional image to identify a blood vessel region therein; identifying an image region in the phase image corresponding to the blood vessel region identified in the main cross sectional image based on the pixel correspondence described above; and adopting the image region identified in the phase image as a blood vessel region therein. Such processed make it possible to identify a blood vessel region in the phase image with high precision and high accuracy.

<Blood Flow Information Generating Unit 232>

The blood flow information generating unit 232 generates blood flow information on the blood vessel of interest db. As described above, the blood flow information generating unit 232 includes the gradient estimator 233, the blood flow velocity calculator 234, the blood vessel diameter calculator 235, and the blood flow amount calculator 236.

<Gradient Estimator 233>

The gradient estimator 233 derives an estimated value of the gradient of the blood vessel of interest db based on data of the supplementary cross section (e.g., cross sectional data, supplementary cross sectional image) acquired by the supplementary scan described above. The estimated gradient value may be, for example, a measured value or an approximate value of the gradient of the blood vessel of interest db at the cross section of interest.

An example is described of the case in which the gradient value of the blood vessel of interest db is actually measured (the first example of gradient estimation). In the cases where the supplementary cross sections C1 and C2 shown in FIG. 5A are applied, the gradient estimator 233 may calculate the gradient value of the blood vessel of interest db at the cross section of interest C0, based on the positional relationship between the cross section of interest C0, the supplementary cross section C1, and the supplementary cross section C2, and further based on the result of identification of the blood vessel regions obtained by the blood vessel region identifying unit 231.

A method of calculating the gradient of the blood vessel of interest db will be described with reference to FIG. 6A. The reference characters G0, G1 and G2 indicate the main cross sectional image at the cross section of interest C0, the supplementary cross sectional image at the supplementary cross section C1, and the supplementary cross sectional image at the supplementary cross section C2, respectively. The reference characters V0, V1 and V2 indicate a blood vessel region in the main cross sectional image G0, a blood vessel region in the supplementary cross sectional image G1, and a blood vessel region in the supplementary cross sectional image G2, respectively. The z coordinate axis shown in FIG. 6A substantially coincides with the incident direction of the measurement light LS. Further, the distance between the main cross sectional image G0 (the cross section of interest C0) and the supplementary cross sectional image G1 (the supplementary cross section C1) is denoted by d, and the distance between the main cross sectional image G0 (the cross section of interest C0) and the supplementary cross sectional image G2 (the supplementary cross section C2) is also denoted by d. The interval between adjacent cross sectional images, that is, the interval between adjacent cross sections is referred to as a distance between cross sections.

The gradient estimator 233 may calculate the gradient A of the blood vessel of interest db at the cross section of interest C0 based on the positional relationship between the three blood vessel regions V0, V1 and V2. This positional relationship is determined, for example, by connecting the three blood vessel regions V0, V1 and V2. As a specific example, the gradient estimator 233 may identify feature positions respectively of the three blood vessel regions V0, V1 and V2, and connect the feature positions. Examples of such a feature position include a center position, a center of gravity position, an uppermost location (i.e., the position having the smallest z coordinate value), a lowermost location (i.e., the position having the largest z coordinate value), and the like. In addition, examples of methods of connecting the feature positions include a method of connecting with a line segment, a method of connecting with an approximate curve (e.g., spline curve, Bezier curve), and the like.

Further, the gradient estimator 233 calculates the gradient A based on the lines connecting the feature positions identified from the three blood vessel regions V0, and V2. When connecting with line segments, for example, the gradient A may be calculated based on the gradient of the first line segment and the gradient of the second line segment. Here, the first line segment connects the feature position of the cross section of interest C0 and the feature position of the supplementary cross section C1, and the second line segment connects the feature position of the cross section of interest C0 and the feature position of the supplementary cross section C2. An example of this calculation processing may be operated to calculate the average value of the gradients of the two line segments. On the other hand, an example of connecting with an approximate curve may be operated to calculate the gradient of the approximate curve at the position where the approximate curve intersects the cross section of interest C0. Note that the distance between cross sections d may be used, for example, when the cross sectional images G0 to G2 are embedded in the xyz coordinate system in the process of determining a line segment or an approximate curve.

In the above examples, the blood vessel regions in three cross sections are taken into consideration; however, other examples may take two cross sections into consideration to calculate the gradient. As a specific example thereof, one of the gradient of the first line segment and the gradient of the second line segment mentioned above may be selected as a targeted gradient. Furthermore, in the above examples, a single value of the gradient is obtained, but two or more values of the gradient may be obtained respectively for two or more positions (or regions) in the blood vessel region V0. If this is the case, the two or more gradient values obtained may be used separately. Alternatively, the two or more gradient values obtained may be subjected to statistical processing to derive a statistic (e.g., the mean value, the maximum value, the minimum value, the median, the mode), and the statistic may be used as the gradient A.

An example is described of the case in which an approximate value of the gradient of the blood vessel of interest is calculated (the second example of gradient estimation). In the event that the supplementary cross section Cp shown in FIG. 5B is applied, the gradient estimator 233 may analyze the supplementary cross sectional image corresponding to the supplementary cross section Cp to calculate an approximate value of the gradient of the blood vessel of interest db at the cross section of interest C0.

A method of approximating the gradient of the blood vessel of interest db will be described with reference to FIG. 6B. The reference character Gp denotes a supplementary cross sectional image of the supplementary cross section Cp. The reference character A denotes the gradient of the blood vessel of interest db, as in the example shown in FIG. 6A.

In the present example, the gradient estimator 233 may identify an image region corresponding to a predetermined tissue of the fundus Ef by analyzing the supplementary cross sectional image Gp. For example, the gradient estimator 233 may identify an image region M corresponding to the inner limiting membrane (ILM) that is a surface tissue of the retina. The image region M is referred to as an inner limiting membrane region. For example, any known segmentation processing may be used for the image region identification.

It is known that the internal limiting membrane and fundus blood vessels are substantially parallel to each other. The gradient estimator 233 calculates the gradient $A_{app}$ of the inner limiting membrane region M at the cross section of interest C0. The gradient $A_{app}$ of the inner limiting membrane region M at the cross section of interest C0 may be used as an approximate value of the gradient A of the blood vessel of interest db at the cross section of interest C0.

Figure 6B:
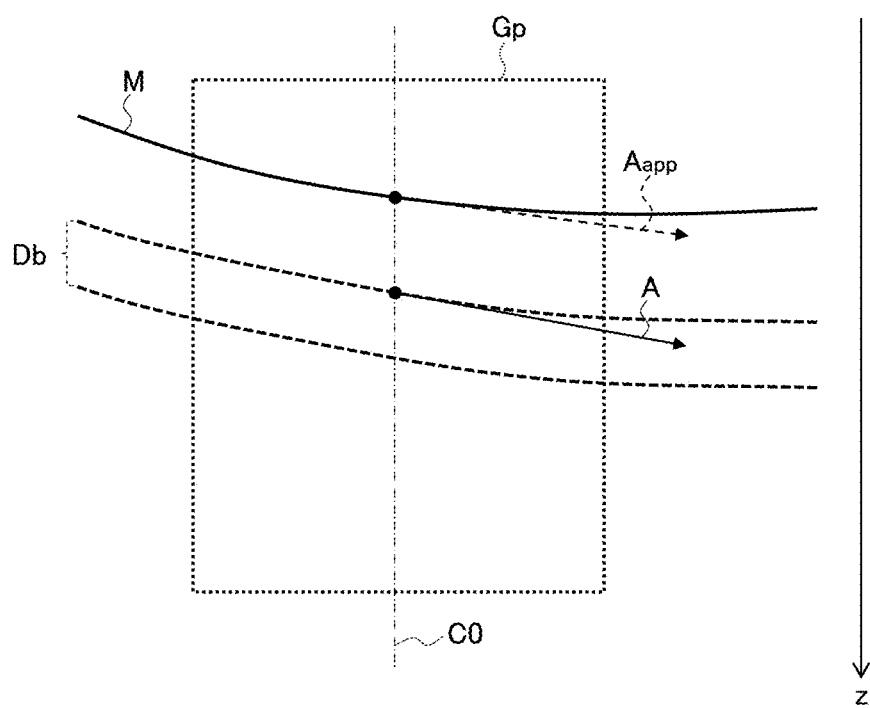
FIG. 6B is a schematic diagram for describing an example of the operation of the blood flow measurement apparatus according to the embodiment.

Note that the gradient A shown in FIG. 6A and the gradient A shown in FIG. 6B are vectors representing the orientation of the blood vessel of interest db, and the definition of such vector values may be arbitrary. As an example, the value of the gradient A may be defined to be the angle formed by the gradient (vector) A and the z axis. Similarly, the gradient $A_{app}$ shown in FIG. 6B is a vector representing the orientation of the inner limiting membrane region M, and the definition of the value of the vector may be arbitrary. For example, the value of the gradient $A_{app}$ may be defined to be the angle formed by the gradient (vector) $A_{app}$ and the z axis. Note that the direction of the z axis is substantially the same as the incident direction of the measurement light LS.

The processing executed by the gradient estimator 233 is not limited to the above processing examples, and may be any processing capable of deriving an estimated value of the gradient of the blood vessel of interest db (e.g., a gradient value of the blood vessel of interest db itself, a value approximating the gradient of the blood vessel of interest db) based on cross sectional data acquired by applying OCT scanning to a cross section of the fundus Ef.

<Blood Flow Velocity Calculator 234>

Based on the temporal change in phase difference obtained as a phase image, the blood flow velocity calculator 234 calculates the blood flow velocity (or blood flow rate) at the cross section of interest C0 for blood flowing in the blood vessel of interest db. A parameter obtained by this calculation may be blood flow velocity at a certain time point, or may be a temporal change in blood flow velocity. The temporal change in blood flow velocity is referred to as blood flow velocity variation information. When blood flow velocity at a certain time point is to be determined, the blood flow velocity at a predetermined time phase in an electrocardiogram (e.g., a time phase corresponding to the R wave) may be selectively acquired, for example. When blood flow velocity variation information is to be determined, a time period during which blood flow velocity is measured is the whole or an arbitrary part of the time period taken for OCT scanning of the cross section of interest C0.

When the blood flow velocity variation information is acquired, the blood flow velocity calculator 234 may further calculate a statistic of the blood flow velocity in the measurement period. Examples of the statistic include the mean value, the standard deviation, the variance, the median, the mode, the global maximum, the global minimum, the local maximum, and the local minimum. The blood flow velocity calculator 234 may create a histogram on the blood flow velocity values.

The blood flow velocity calculator 234 calculates the blood flow velocity using Doppler OCT technique. In the blood flow velocity calculation, the gradient A (or its approximate value $A_{app}$) of the blood vessel of interest db at the cross section of interest C0 calculated by the gradient estimator 233 is taken into account. More specifically, the blood flow velocity calculator 234 may be configured to use the following relationship.

$$\Delta f = \frac{2nv\cos\theta}{\lambda} \qquad \text{[Equation 1]}$$

Here: $\Delta f$ denotes the Doppler shift given to scattered light of the measurement light LS; n denotes the refractive index of medium; v denotes the flow velocity of the medium (blood flow velocity); θ denotes the angle between projection direction of the measurement light LS and the flow vector of the medium; and λ denotes the center wavelength of the measurement light LS.

In the present embodiment, n and λ are known, $\Delta f$ is derived from the temporal change of the phase difference, and θ is derived from the gradient A (or, from the approximate gradient value $A_{app}$). In some typical examples, θ is equal to the gradient A (or, to the approximate gradient value $A_{app}$). Substituting these values into the above equation yields the blood flow velocity v.

<Blood Vessel Diameter Calculator 235>

The blood vessel diameter calculator 235 calculates the diameter of the blood vessel of interest db at the cross section of interest C0. Examples of the blood vessel diameter calculation include the first calculation method on the basis of a fundus image (a front image of an eye fundus) and the second calculation method on the basis of a cross sectional image.

When applying the first calculation method, an area of the fundus Ef including the location of the cross section of interest C0 is photographed in advance. A fundus image thus obtained may be an observation image (e.g., a frame(s) thereof), or may be a photographed image. When the photographed image is a color image, any image obtained from the color image (e.g., a red-free image) may be used. The photographed image may be a fluorescence image obtained by fundus fluorescence angiography (e.g., fluorescein angiography), or may be a blood vessel emphasized image obtained by OCT angiography. An image created using OCT angiography is also referred to as an angiogram or a motion contrast image.

The blood vessel diameter calculator 235 sets a scale for fundus images based on various kinds of factors used to determine the relationship between the scale for images and the scale in the real space. Examples of such factors include the photographing angle of view (photographing magnification), the working distance, and information on an ocular optical system. The scale for fundus images may represent a length in the real space. As a specific example, the scale for fundus images may be configured to associate interval between adjacent pixels with a scale (distance) in the real space (e.g., pixel interval=10 µm). Note that it is possible to determine, in advance, the relationship between various values of the above factors and scales (values) in the real space, and then store a table or a graph that represents the relationship determined. In this case, the blood vessel diameter calculator 235 may select, from the table or the graph, a scale corresponding to the above factors and adopt the scale selected.

Based on the scale and the pixels included in the blood vessel region V0, the blood vessel diameter calculator 235 calculates the diameter of the blood vessel of interest db at the cross section of interest C0, that is, the diameter of the blood vessel region V0. As a specific example, the blood vessel diameter calculator 235 may calculate the maximum or the mean value of a plurality of diameters of the blood vessel region V0 corresponding to different directions. In some other examples, the blood vessel diameter calculator 235 may determine an approximate circle or an approximate ellipse of the contour of the blood vessel region V0, and then calculate the diameter of the approximate circle or the approximate ellipse. Note that once the blood vessel diameter of the blood vessel region V0 is determined, the area of the blood vessel region V0 can (substantially) be calculated. That is, it is possible to substantially associate blood vessel diameters with blood vessel areas in a one-to-one fashion. Therefore, an area of a blood vessel may be calculated in place of a diameter of the blood vessel.

The second calculation method will be described. In the second calculation method, typically, a cross sectional image at the cross section of interest C0 is used. The cross sectional image may be a main cross sectional image or any other image.

The scale of the cross sectional image is determined based on OCT measurement conditions. In the present embodiment, the cross section of interest C0 is scanned as shown in FIG. 5A or FIG. 5B. The length of the cross section of interest C0 is determined based on various kinds of factors that define the relationship between the scale of an image and the scale in the real space such as the working distance and information about ocular optical system. The blood vessel diameter calculator 235, for example, determines the interval between adjacent pixels based on the length of the cross section of interest C0, and calculates the diameter of the blood vessel of interest db at the cross section of interest C0 in the same manner as in the first calculation method.

<Blood Flow Amount Calculator 236>

Based on the calculation result of the blood flow velocity and the calculation result of the blood vessel diameter, the blood flow amount calculator 236 calculates a flow amount (or, flow volume) of blood that flows in the blood vessel of interest db. An example of the blood flow amount calculation will be described below.

It is assumed that the blood flow in a blood vessel is the Hagen-Poiseuille flow. The blood vessel diameter is denoted by w, and the maximum blood flow velocity is denoted by Vm. Then, the blood flow amount Q is expressed as in the following equation.

$$Q = \frac{\pi w^2}{8} Vm \qquad \text{[Equation 2]}$$

The blood flow amount calculator 236 substitutes the blood vessel diameter w calculated by the blood vessel diameter calculator 235 and the maximum blood flow velocity Vm based on the blood flow velocity calculated by the blood flow velocity calculator 234 into the above equation, thereby determining the targeted blood flow amount Q.

<Cross Section Setting Unit 237>

The main controller 211 displays a front image of the fundus Ef on the display 241. The front image may be any type of image, and may be any of an observation image, a photographed image, a fluorescence image, an OCT angiography image, an OCT projection image, and an OCT shadowgram.

The user operates the operation device 242 to designate one or more cross sections of interest in the displayed front image of the fundus Ef. Each cross section of interest is designated to intersect a blood vessel of interest. Based on the designated one or more cross sections of interest and the front image of the fundus Ef, the cross section setting unit 237 may set one or more supplementary cross sections for each of the one or more cross sections of interest. Note that a supplementary cross section may be set manually.

In another example, the cross section setting unit 237 may be configured to analyze a front image of the fundus Ef to identify one or more blood vessels of interest. The identification of the blood vessels of interest is performed based on, for example, the thickness of a blood vessel, the positional relationship between a blood vessel of interest and a predetermined site of a fundus (e.g., the optic nerve head, the macula), the type of a blood vessel (e.g., artery or vein), or the like. In addition, the cross section setting unit 237 may set one or more cross sections of interest and one or more supplementary cross sections, for each of the one or more blood vessels of interest identified.

In this manner, a cross section of interest and a supplementary cross section as illustrated in FIG. 5A or FIG. 5B are set with respect to the fundus Ef by the user, by the cross section setting unit 237, or by the cooperation between the user and the cross section setting unit 237.

<Vignetting Judging Unit 238>

The vignetting judging unit 238 judges (determines) occurrence (presence or absence) of vignetting based on a detection result of the return light of the light incident on the subject's eye E through the optical system provided in the blood flow measurement apparatus 1.

The type, purpose, and intensity (amount) of the light incident on the subject's eye E for the vignetting judgement may be arbitrary. The type of the incident light may be infrared light or visible light, for example. The purpose of the incident light may be, for example, imaging, examination, or measurement.

The incident light that can be employed for the present embodiment may be, for example, the measurement light LS for OCT scanning, or the observation illumination light, the photographing illumination light or excitation light for fundus imaging. The result of detection of the return light of the incident light may be, for example, an OCT image, an observation image, a photographed image, or a fluorescence image.

The "vignetting" in the present embodiment includes vignetting (decrease in brightness) that occurs when part or all of incident light for eye fundus blood flow measurement or the return light of the incident light is blocked by the pupil. The "occurrence of vignetting" in the present embodiment includes any of the following: whether or not vignetting occurs; whether or not the degree of vignetting exceeds a predetermined level.

Examples of the processing executed by the vignetting judging unit 238 will be described. The first example and the second example will be described below regarding the vignetting judgement methods and techniques. However, the methods and techniques of judging the occurrence of vignetting are not limited thereto.

In the first example, the incident light for the vignetting judgement is the measurement light LS, and a predetermined OCT scan is applied. For example, the mode of the OCT scan in the present example may be an OCT scan for the cross section of interest C0 (or for the supplementary cross section C1 and/or for the supplementary cross section C2) shown in FIG. 5A. As an alternative, the mode of the OCT scan may be an OCT scan for the supplementary cross section Cp shown in FIG. 5B. The OCT scan in the present example is repetitive scanning for the same cross section, for example.

When applying the repetitive scanning to the supplementary cross section Cp (or, to the supplementary cross section C1 and/or to the supplementary cross section C2), the gradient estimation of the blood vessel of interest db may be performed in parallel with the vignetting judgement. Alternatively, when applying the repetitive scanning to the supplementary cross section Cp (or, to the supplementary cross section C1 and/or to the supplementary cross section C2), a smooth transition from the vignetting judgement to the gradient estimation of the blood vessel of interest db is possible.

Figure 7A:
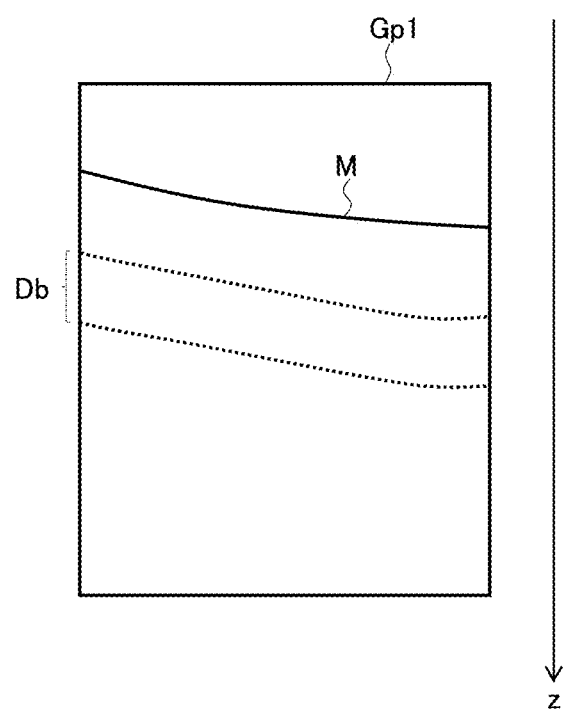
FIG. 7A is a schematic diagram for describing an example of the operation of the blood flow measurement apparatus according to the embodiment.
Figure 7B:
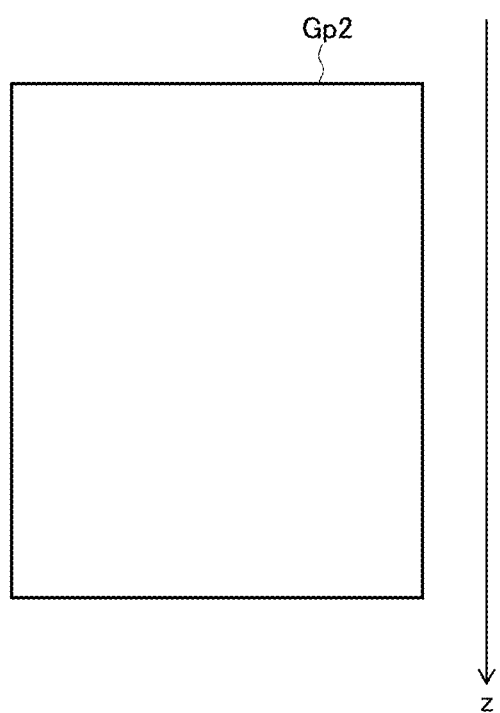
FIG. 7B is a schematic diagram for describing an example of the operation of the blood flow measurement apparatus according to the embodiment.

In the cases where the supplementary cross section Cp is employed to be subjected to the repetitive scanning and if there is no occurrence of vignetting, the cross sectional image Gp1 (cross sectional data) is obtained. The cross sectional image Gp1 represents the morphology (or structure) of the supplementary cross section Cp as shown in FIG. 7A. On the other hand, if there is occurrence of vignetting, the cross sectional image Gp2 (cross sectional data) is obtained in which the morphology (or structure) of the supplementary cross section Cp is not depicted as shown in FIG. 7B. Note that, in a state where the alignment is appropriate, the optical scanner 44 is placed at a position substantially conjugate with the pupil of the subject's eye E, and thus the deflection center (pivot) of the measurement light LS substantially coincides with the pupil. Therefore, when the vignetting of the measurement light LS occurs on the pupil, the cross sectional image Gp2 (cross sectional data) is obtained in which the morphology (or structure) of the supplementary cross section Cp is not depicted.

The vignetting judging unit 238 analyzes the cross sectional image obtained through the OCT scan for the supplementary cross section Cp and judges whether or not the morphology (or structure) of the supplementary cross section Cp is depicted. For example, the vignetting judging unit 238 may be configured to judge whether or not the inner limiting membrane region (M) is depicted in the cross sectional image. The judgement result that "the inner limiting membrane region is depicted in the cross sectional image" corresponds to the judgement result that "vignetting does not occur (or no occurrence of vignetting)". On the contrary, the judgement result that "the inner limiting membrane region is not depicted in the cross sectional image" corresponds to the judgement result that "vignetting occurs (or occurrence of vignetting)".

The second example of the processing executed by the vignetting judging unit 238 will be described. In the present example, the incident light for the vignetting judgement is the illumination light for fundus photography (fundus imaging). The incident light may also be the observation illumination light or the photographing illumination light. The vignetting judging unit 238 analyzes a fundus image to judge whether or not a decrease in light amount attributable to the vignetting has occurred. For example, the vignetting judging unit 238 judges whether or not there is a difference between the brightness of the central part of the fundus image and the brightness of the peripheral part of the fundus image. More specifically, the vignetting judging unit 238 judges whether or not the light amount in the peripheral part of the fundus has decreased. Such a judgement on the decrease in the light amount is performed with reference to the values of the pixels that constitute the fundus image. In some typical examples, the values of the pixels here refer to the brightness distribution over the pixels. The judgement includes, for example, image processing such as thresholding and labeling.

According to the second example, the degree of vignetting may be easily judged. The degree of vignetting is evaluated based on, for example, the characteristics or features of the image region in which the peripheral light amount of the fundus image has decreased. The vignetting judging unit 238 may calculate an evaluation value in this way, and may judge the occurrence of vignetting based on the magnitude of the evaluation value. The evaluation value may be, for example, the size (area) of the region in which the peripheral light amount has decreased. The "occurrence (presence or absence) of vignetting" in the present example corresponds to, for example, whether or not the degree of vignetting exceeds a predetermined degree. In some typical examples, the vignetting judging unit 238 compares the calculated evaluation value with a threshold value and judges that "vignetting occurs" if the evaluation value exceeds the threshold value. If the evaluation value is less than or equal to the threshold value, the vignetting judging unit 238 judges that "no vignetting occurs".

The data processor 230 that functions as described above may include, for example, a processor, a RAM, a ROM, a hard disk drive, and the like. A storage device such as a hard disk drive may store, in advance, a computer program that causes the processor to execute the above functions.

<User Interface 240>

The user interface (UI) 240 includes the display device 241 and the operation device 242. The display device 241 includes the display 3 shown in FIG. 1 and/or another display device. The operation device 242 includes any types of operation devices. The user interface 240 may include, for example, a device having both a display function and an operation function, such as a touch panel.

<Operation>

Figure 8:
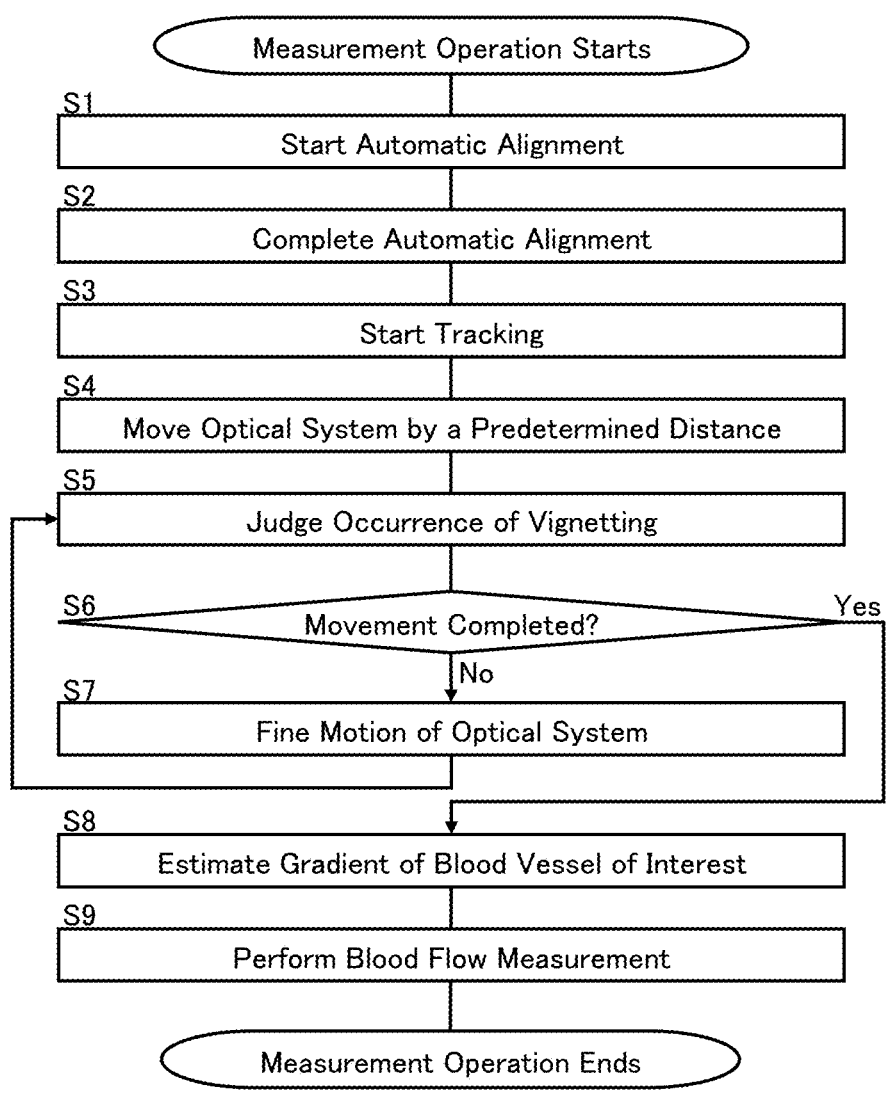
FIG. 8 is a flowchart showing an example of the operation of the blood flow measurement apparatus according to the embodiment.

An example of the operation of the blood flow measurement apparatus 1 will be described. FIG. 8 shows an example of the operation of the blood flow measurement apparatus 1. It is assumed that preparatory processing such as input of the patient ID has already been performed.

(S1: Start Automatic Alignment)

First, the blood flow measurement apparatus 1 executes automatic alignment. The automatic alignment is performed using the alignment indicator as described above, for example. Alternatively, the automatic alignment may be performed using two or more anterior eye segment cameras, as disclosed in Japanese Unexamined Patent Application Publication No. 2013-248376. The method and technique of performing automatic alignment are not limited to these examples.

(S2: Complete Automatic Alignment)

The automatic alignment is completed when the relative position between the subject's eye E and the optical system matches with each other in all the x, y, and z directions.

(S3: Start Tracking)

After the completion of the automatic alignment, the blood flow measurement apparatus 1 starts tracking in order to move the optical system in accordance with the movement of the subject's eye E (the fundus Ef). The tracking is carried out by the combination of the following operations, for example: an operation of acquiring an observation image of the fundus Ef using infrared light; an operation of analyzing the observation image to detect the movement of the fundus Ef; and an operation of moving the optical system in accordance with the movement of the fundus Ef detected.

Here, setting of the fundus imaging conditions such as focus adjustment with respect to the fundus Ef and setting of the OCT measurement conditions such as optical path length adjustment may be performed. Further, the selection of a blood vessel of interest, the setting of a cross section of interest, the setting of a supplementary cross section, and the like may be executed at this stage or at any other timing. In the present operation example, it is assumed that the blood vessel of interest db, the cross section of interest C0, and the supplementary cross section Cp shown in FIG. 5B are set.

(S4: Move Optical System by a Predetermined Distance)

At this stage, the corneal apex (or the center of the pupil) and the optical axis of the optical system substantially match with each other in the xy directions as well as the distance between the subject's eye E and the optical system (the objective lens 22) in the z direction substantially matches with the working distance.

The main controller 211 controls the movement mechanism 150 to move the optical system by a predetermined distance in a predetermined direction in the xy plane. In other words, the main controller 211 applies the first movement control to the movement mechanism 150 in order to move the optical system by a predetermined distance from the optical axis of the optical system in a predetermined direction that is orthogonal to the optical axis of the optical system. As a result, the optical axis of the optical system is moved from the position H0 to the position H1. Here, the position H0 is a position that substantially coincides with the corneal apex (or the center of the pupil) in the xy directions while the position H1 is a position that is separated from the position H0 by a predetermined distance in the upper left direction.

The movement direction of the optical system in the first movement control (referred to as an initial movement direction) may be any direction and may be set in advance. The movement distance of the optical system in the first movement control (referred to as an initial movement amount) may be any distance, and may be a distance set as a default, for example. Note that the initial movement amount may be, for example, a distance set according to the occurrence (presence or absence) of mydriasis, or a distance set according to the pupil diameter of the subject's eye E. The details regarding the initial movement amount thus defined will be described later.

(S5: Judge Occurrence of Vignetting)

After the step S4, the main controller 211 starts the scanning of the supplementary cross section Cp shown in FIG. 5B. This scanning is employed as an OCT scan for the vignetting judgement. The vignetting judging unit 238 judges the occurrence of vignetting based on cross sectional data acquired by the OCT scan. The judgement of the occurrence of vignetting includes the following processes, for example: the image constructing unit 220 (the cross sectional image constructing unit 221) constructs a cross sectional image of the supplementary cross section Cp from the cross sectional data acquired by the OCT scan; and the vignetting judging unit 238 judges the occurrence of vignetting by determining whether or not the morphology (or structure) of the supplementary cross section Cp is depicted in the cross sectional image constructed.

(S6: Movement Completed?)

If a predetermined condition (referred to as a movement completion condition) is satisfied, the blood flow measurement apparatus 1 determines that the movement of the optical system has been completed (S6: Yes), and the process proceeds to the step S8. If the movement completion condition has not been satisfied (S6: No), the process proceeds to the step S7. The movement completion condition will be described later.

(S7: Fine Motion of Optical System)

If the blood flow measurement apparatus 1 determines that the movement completion condition has not been satisfied in the step S6 (S6: No), the main controller 211 applies the second movement control to the movement mechanism 150 in order to perform fine adjustment of the position of the optical system, based on the judgement result obtained in the step S5.

Figure 9A:
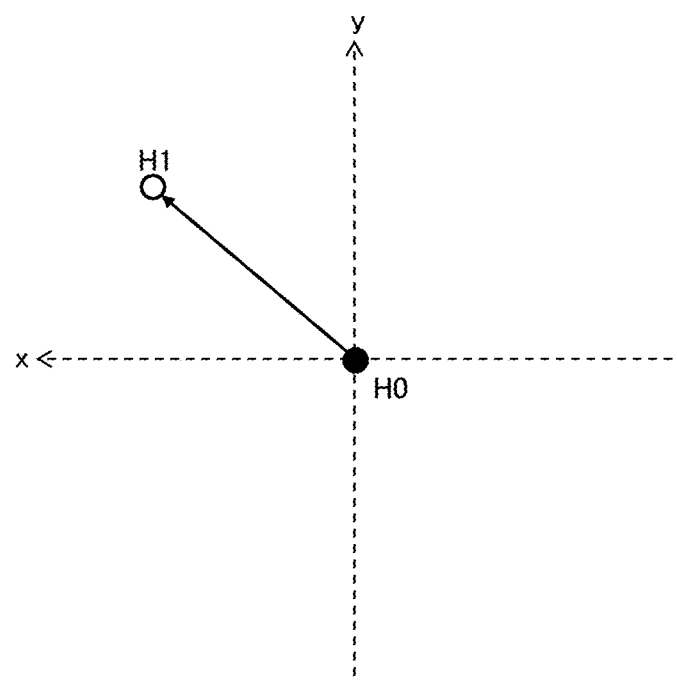
FIG. 9A is a schematic diagram for describing an example of the operation of the blood flow measurement apparatus according to the embodiment.
Figure 9B:
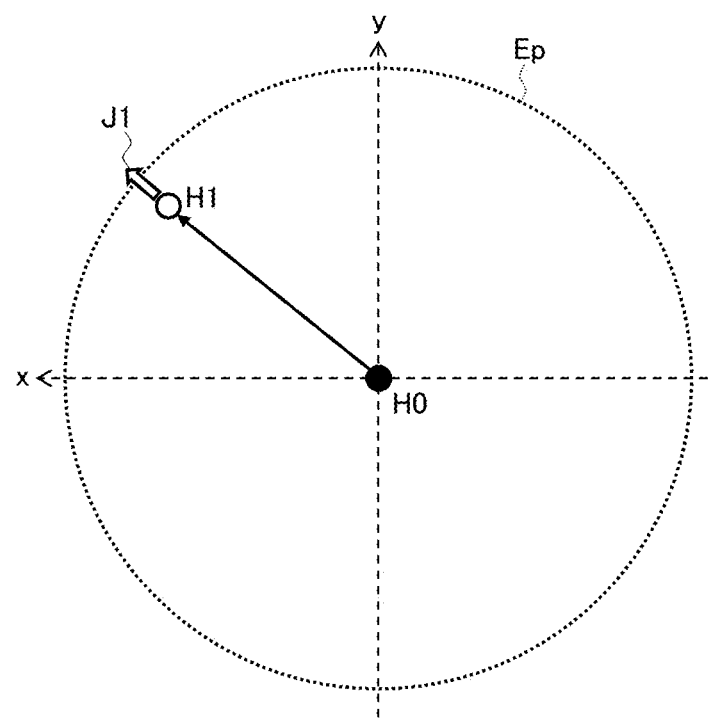
FIG. 9B is a schematic diagram for describing an example of the operation of the blood flow measurement apparatus according to the embodiment.

As an example, in the cases where the vignetting judging unit 238 judges in the step S5 that the vignetting has not occurred, the main controller 211 executes the second movement control to further move the optical system in the initial movement direction. For example, as shown in FIG. 9B, when the optical axis position H1 after the first movement control is located inside the pupil Ep, the OCT scan for the supplementary cross section Cp is appropriately performed and a cross sectional image in which the morphology (or structure) of the supplementary cross section Cp is depicted, as shown in FIG. 7A, is acquired. As a result of this, the vignetting judging unit 238 judges that no vignetting occurs. As indicated by the reference character J1 in FIG. 9B, the main controller 211 controls the movement mechanism 150 to move the optical system in the initial movement direction by a predetermined distance. Here, the predetermined distance is a predetermined amount of fine motion. In this manner, when the vignetting judging unit 238 judges in the step S5 that the vignetting has not occurred, the optical axis of the optical system is moved in the direction toward the outer edge of the pupil Ep. In other words, the optical axis of the optical system is moved in the direction away from the optical axis position H0 that is the position of the optical axis immediately after the automatic alignment.

Figure 9C:
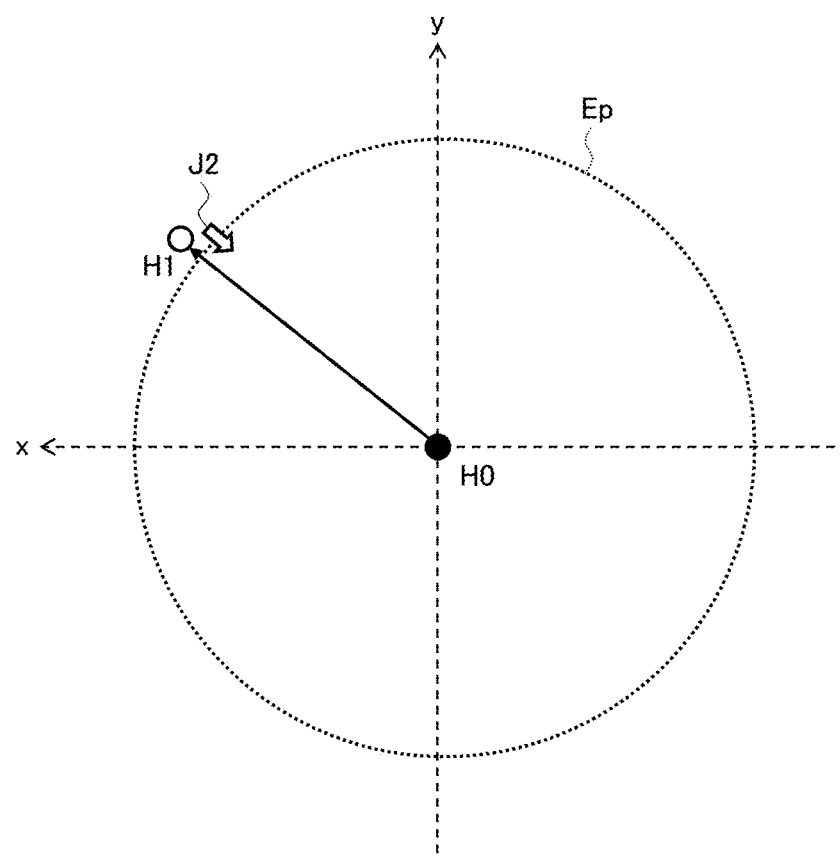
FIG. 9C is a schematic diagram for describing an example of the operation of the blood flow measurement apparatus according to the embodiment.

On the contrary, in the cases where the vignetting judging unit 238 judges in the step S5 that the vignetting has occurred, the main controller 211 executes the second movement control to move the optical system in the direction opposite to the initial movement direction. For example, as shown in FIG. 9C, when the optical axis position H1 after the first movement control is located outside the pupil Ep, the measurement light LS is blocked by the iris etc. Consequently, a cross sectional image is obtained in which the morphology (or structure) of the supplementary cross section Cp is not depicted, as shown in FIG. 7B. As a result of this, the vignetting judging unit 238 judges that the vignetting has occurred. As indicated by the reference character J2 in FIG. 9C, the main controller 211 controls the movement mechanism 150 to move the optical system in the direction opposite to the initial movement direction by a predetermined distance. Here, as in the case above, the predetermined distance is a predetermined amount of fine motion. In this fashion, when the vignetting judging unit 238 judges in the step S5 that the vignetting has occurred, the optical axis of the optical system is moved in the direction toward the optical axis position H0 that is the position of the optical axis immediately after the automatic alignment.

After the fine movement of the optical system has been performed, the process returns to the step S5. The steps S5 to S7 are repeated until the determination result becomes "Yes" in the step S6. Note that when the steps S5 to S7 have been repeated a predetermined number of times or when the steps S5 to S7 have been repeated for a predetermined period of time, the blood flow measurement apparatus 1 may output the determination indicating an error.

The movement completion condition in the step S6 will be described. For example, the movement completion condition corresponds to a state in which no vignetting occurs, and also a state in which the optical system is located at a position where a shift (deviation, displacement) from the position of the optical axis immediately before the first movement control becomes maximum. If this is the case, the main controller 211 repeatedly executes the steps S5 to S7 (the second movement control) until the following conditions are met: the vignetting judging unit 238 judges that there is no occurrence of vignetting; and the optical system is located at a position where a shift from the position of the optical axis immediately before the first movement control becomes maximum.

As an example, if the vignetting judging unit 238 judges that the vignetting occurs after the fine movement in the initial movement direction, the optical system may be returned to the optical axis position before the fine movement in order to satisfy the movement completion condition of the present example. As another example, if the vignetting judging unit 238 judges that the vignetting does not occur after the fine movement in the direction opposite to the initial movement direction, the position of the optical system after the fine movement satisfies the movement completion condition of the present example.

Note that the determination of whether or not the movement completion condition of the present example is satisfied is not limited to these examples. Further, the movement completion condition is not limited to that of the present example.

(S8: Estimate Gradient of Blood Vessel of Interest)

When the movement of the optical system is determined to be completed in the step S6 (S6: Yes), the blood flow measurement apparatus 1 performs the estimation of the gradient of the blood vessel of interest db. For the gradient estimation of the present example, the cross sectional data of the supplementary cross section Cp may be used as in the vignetting judgement, for example.

(S9: Perform Blood Flow Measurement)

After the estimated value of the gradient of the blood vessel of interest db is obtained in the step S8, the blood flow measurement apparatus 1 performs the blood flow measurement on the cross section of interest C0 and then generates blood flow information in the same manner as described above.

Some modification examples of the operation described above will be described. In eye fundus blood flow measurements using OCT scanning, having an appropriate angle formed by the direction of the blood vessel of interest db and the incident direction of the measurement light LS is important, as described above. Here, the angle formed by the direction of the blood vessel of interest db and the incident direction of the measurement light LS is referred to as a measurement angle.

Hence, by displaying the value of the measurement angle obtained by the gradient estimator 233 (estimated value) and the value of a preset appropriate measurement angle (target angle) on the display device 241, the blood flow measurement apparatus 1 is capable of presenting the measurement angle and the target angle to the user. Such display control is executed by the main controller 211.

The target angle is set, for example, in the range of 78 degrees to 85 degrees, and more preferably in the range of 80 degrees to 85 degrees. The target angle may be a single value or a range defined by an upper limit and/or a lower limit. The target angle may be any of the followings, for example: a default value; a default range; a value or a range set by the user or another person such as a maintenance service person; and a value or a range set by the blood flow measurement apparatus 1 or another apparatus such as a server in a medical facility or a health facility or an apparatus that monitors the operation of the blood flow measurement apparatus 1. Examples of ways of setting the target angle, in the cases where the blood flow measurement apparatus 1 or the like sets the target angle, include the followings: setting once again the target angle applied to the subject's eye E in the past; setting the target angle according to the attributes of the subject; and setting the target angle according to the attributes of the subject's eye E.

In the present example, the main controller 211 may display the measurement angle obtained at any timing after the first movement control by the gradient estimator 233 on the display device 241 together with the target angle. In some typical examples, the main controller 211 may display the measurement angle obtained after the first movement control by the gradient estimator 233 on the display device 241 together with the target angle, or display the measurement angle obtained after the second movement control by the gradient estimator 233 on the display device 241 together with the target angle The user may input an instruction by referring to the measured value of the measurement angle and the value of the target angle. For example, if a measurement angle that (substantially) matches with the target angle is obtained, the user may input a blood flow measurement start instruction using the operation device 242. Further, the main controller 211 may be configured to compare the measured value of the measurement angle with the target angle, and execute the blood flow measurement start control if these values (substantially) match with one another. In addition, the main controller 211 may be configured to further perform the second control if these values do not meet one another.

An appropriate measurement angle may not be achieved even though the second movement control is repeatedly performed. If this is the case, the user may change the target angle using the operation device 242. Alternatively, the target angle may be changed by the blood flow measurement apparatus 1. For example, the main controller 211 may be configured to change the target angle when the second movement control has been repeated a predetermined number of times or when the second movement control has been executed for a predetermined period of time. Note that a range within which the target angle can be changed may be set in advance.

If the target angle has been changed, the main controller 211 may execute the first movement control again. For example, in response to the change of the target angle, the main controller 211 may execute the step S4 of the operation shown in FIG. 8 again and further execute the processes of the step S5 and thereafter again.

The main controller 211 may be configured to start the blood flow measurement and acquire the blood flow information if the value of the measurement angle obtained by the gradient estimator 233 (substantially) matches with the target angle. In some typical examples, the main controller 211 may start blood flow measurement if the value of the measurement angle obtained by the gradient estimator 233 after the second movement control (substantially) matches with the target angle.

According to such a modification example, the blood flow measurement apparatus 1 may be used in the following way. Assume that the initial value of the target angle is set to 80 degrees. If the measurement angle of 80 degrees is not achieved even after having repeatedly performed the second movement control, the user changes the target angle to 78 degrees, for example. Then, the blood flow measurement apparatus 1 performs the first movement control again (S4), and further executes the vignetting judgement (S5), the second movement control and the like. Then, the user checks the value of the measurement angle obtained after the second movement control displayed on the display device 241 and inputs a blood flow measurement start instruction if the measurement angle of 78 degrees is achieved. On the other hand, if the measurement angle of 78 degrees is not achieved even after having repeated the second movement control, the user may select, for example, any of the following actions: changing the target angle again; performing another measurement from the start; and discontinuing the measurement.

<Actions and Effects>

Some actions and effects of the blood flow measurement apparatus according to the embodiment will be described.

The blood flow measurement apparatus (1) of the embodiment includes a blood flow measuring unit, a movement mechanism, a controller, and a judging unit.

The blood flow measuring unit includes an optical system for performing optical coherence tomography (OCT) scanning, and is configured to acquire blood flow information based on data acquired by the OCT scanning. In the above embodiment, the optical system of the blood flow measuring unit includes the measurement arm shown in FIG. 1 and the optical system shown in FIG. 2. Further, the blood flow measuring unit includes the image constructing unit 220 and the data processor 230 (the blood flow information generating unit 232).

The movement mechanism has a configuration for moving the optical system of the blood flow measuring unit. In the above embodiment, the movement mechanism includes the movement mechanism 150.

The controller is configured to apply the first movement control to the movement mechanism to move the optical system in the first direction orthogonal to an optical axis of the optical system of the blood flow measuring unit by a predetermined distance from the optical axis. In the above embodiment, the controller includes the main controller 211. As illustrated in FIG. 9A, the main controller 211 applies the first movement control to the movement mechanism 150 to move the measurement arm (the optical axis thereof) to the position H1 that is apart from the optical axis position H0 immediately after the automatic alignment by a predetermined distance in the upper left direction.

After the first movement control, the judging unit judges occurrence of vignetting based on a detection result of return light of light incident on the subject's eye through the optical system of the blood flow measuring unit. In the above embodiment, the judging unit includes the vignetting judging unit 238.

The light incident on the subject's eye for the vignetting judgement may be light for OCT scanning (e.g., the measurement light LS), light for fundus imaging (e.g., the observation illumination light or the photographing illumination light), light dedicated to the vignetting judgement, or any light other than these.

The light incident on the subject's eye for the vignetting judgement may typically be light for blood flow measurement (light for OCT scanning) or another light incident on the subject's eye traveling along the axis of the blood flow measurement light.

In the cases where vignetting judgement uses incident light that is not traveling along the axis of the blood flow measurement light, the optical system may be configured to have the light for the blood flow measurement and the light for the vignetting judgement pass through substantially the same position in or near the pupil.

In some alternative examples for the cases where vignetting judgement uses incident light that is not traveling along the axis of the blood flow measurement light, if the light path for the blood flow measurement and the light path for the vignetting judgement are both known or recognizable, then the vignetting judgement on the light for the blood flow measurement may be carried out based on the relative positional relationship between the paths and on a state of vignetting of the light for the vignetting judgement.

Then, the controller applies the second movement control to the movement mechanism to further move the optical system of the blood flow measuring unit based on the judgement result obtained by the judging unit.

According to such an embodiment, in the offset operation of the measurement arm for obtaining optimum Doppler signals for the eye fundus blood flow measurement, the vignetting judgement can be performed after the measurement arm is displaced by a predetermined distance by the first movement control, and then the position of the measurement arm can be adjusted by performing the second movement control according to the result of the vignetting judgement. Such a configuration makes it possible to shorten the time required to achieve the optimum offset position (shift position) in comparison to the method of gradually increasing the shift amount of the measurement arm with respect to the optical axis of the subject's eye so that vignetting caused by the pupil does not occur. As a result, the burden on the subject can be reduced by the embodiment.

In some embodiments, the optical system of the blood flow measuring unit may apply an OCT scan to a cross section lying along a blood vessel of interest of the fundus to acquire cross section data after the first movement control. Further, the judging unit may judge the occurrence of the vignetting based on the cross sectional data. In the embodiment described above, the OCT scan may be applied to the supplementary cross section Cp shown in FIG. 5B to obtain cross sectional data (i.e., a supplementary cross sectional image), and the vignetting judging unit 238 may judge the occurrence of vignetting based on the cross sectional data obtained (see FIG. 7A and FIG. 7B).

In some embodiments, an estimated value of the gradient of the blood vessel of interest may be obtained based on the cross sectional data acquired by applying the OCT scan to the cross section oriented along the blood vessel of interest of the fundus (gradient estimator). In the above embodiment, the gradient estimator 233 may derive the gradient of the blood vessel of interest db itself, or the gradient of the internal limiting membrane that approximates the gradient of the blood vessel of interest db.

According to such a configuration, the OCT scan is applied to the cross section lying along the blood vessel of interest of the fundus for both the OCT scan for the vignetting judgement and the OCT scan for the blood vessel gradient estimation. Therefore, the gradient estimation of the blood vessel can be performed in parallel with the vignetting judgement, and also a smooth transition from the vignetting judgement to the gradient estimation of the blood vessel becomes possible. These advantages contribute to shortening of the time required for the measurement and reduction of the burden on the subject.

In some embodiments, the controller displays the estimated value of the gradient of the blood vessel of interest obtained by the gradient estimator after the second movement control and a target value of the gradient set in advance on a display device. In the above embodiment, the main controller 211 may display the following pieces of information on the display device 241: the estimated value of the gradient of the blood vessel of interest db obtained by the gradient estimator 233 at an arbitrary timing after the first movement control (e.g., after the second movement control) (the measurement angle); and the target value of the gradient set in advance (the target angle).

With such a configuration, the user can recognize the measurement angle of the blood vessel of interest and further compare the measurement angle with the target angle. This allows the user to input an instruction such as an instruction(s) to start and/or stop the blood flow measurement as desired.

In some embodiments, the user may change the target angle using the operation unit (242). The controller may execute the first movement control again if the target angle has been changed.

With such a configuration, first, the user may change the target angle as desired. Furthermore, in response to the change in the target angle, the blood flow measurement apparatus 1 may again perform the offset operation of the measurement arm for obtaining optimum Doppler signals for the eye fundus blood flow measurement. This makes it possible to reset the target angle and search again for an appropriate shift position when an appropriate offset state cannot be achieved even if the second movement control has been repeated.

In some embodiments, the controller may control the blood flow measuring unit to obtain blood flow information if the estimated value of the gradient of the blood vessel of interest obtained by the gradient estimator after the second movement control substantially matches with the target value of the gradient set in advance. In the above embodiment, the main controller 211 may start the blood flow measurement in response to having the measurement angle (substantially) matching with the target angle.

With such a configuration, the blood flow measurement apparatus can start the blood flow measurement automatically in response to having obtained an appropriate measurement angle. As a result, the blood flow measurement apparatus will not miss the timing at which an appropriate measurement angle is obtained, and thus, the time required for the measurement can be shortened.

In some embodiments, the controller may perform the second movement control to further move the optical system of the blood flow measuring unit in the first direction same as the movement direction in the first movement control if the judging unit has judged that the vignetting has not occurred. On the contrary, the controller may perform the second movement control to move the optical system of the blood flow measuring unit in a direction opposite to the first direction if the judging unit has judged that the vignetting has occurred.

If the judging unit has judged that the vignetting has not occurred, the optical axis of the measurement arm is considered to be located inside the pupil of the subject's eye. This means that there is room for increasing the shift amount of the measurement arm in order to obtain optimum Doppler signals for the eye fundus blood flow measurement. Therefore, some embodiments may move the optical system of the blood flow measuring unit further in the first direction same as the movement direction in the first movement control to search for a more appropriate shift position.

On the contrary, if the judging unit has judged that the vignetting has occurred, the optical axis of the measurement arm is considered to be located outside the pupil of the subject's eye. Therefore, some embodiments may move the optical system of the blood flow measuring unit in the direction opposite to the movement direction in the first movement control to adjust the shift position so that the optical axis of the measurement arm passes through the inside of the pupil.

With the configuration as described above, it becomes possible to maximize the shift amount of the measurement arm within the range where vignetting does not occur.

In some embodiments, the controller may repeatedly perform the second movement control until the judging unit judges that the vignetting does not occur and the optical system is located at a position in which a shift from the position of the optical axis immediately before the first movement control becomes maximum.

In the above embodiment, the main controller 211 may repeatedly perform the second movement control until the vignetting judging unit 238 judges that the vignetting does not occur and also until the optical axis of the measurement arm is located at a position in which the shift amount from the position H0 of the optical axis of the measurement arm immediately before the first movement control becomes maximum. Furthermore, the main controller 211 may start the blood flow measurement when the shift amount of the measurement arm is maximized in the range where vignetting does not occur.

Second Embodiment

As described in the operation example of the first embodiment, tracking for moving the optical system according to the movement of the subject's eye (the fundus) may be applied to the eye fundus blood flow measurement in some cases. Since the time required for OCT scanning in the eye fundus blood flow measurement is about several seconds, it is common to employ tracking to reduce the bad influence of eye movement.

As described above, tracking is typically implemented by the combination of the following operations: the operation of acquiring an infrared observation image of the eye fundus; the operation of analyzing the infrared observation image to detect the movement of the eye fundus; and the operation of controlling the movement mechanism according to the movement of the eye fundus detected (that is, the operation of moving the optical system to follow the movement of the fundus).

Figure 10:
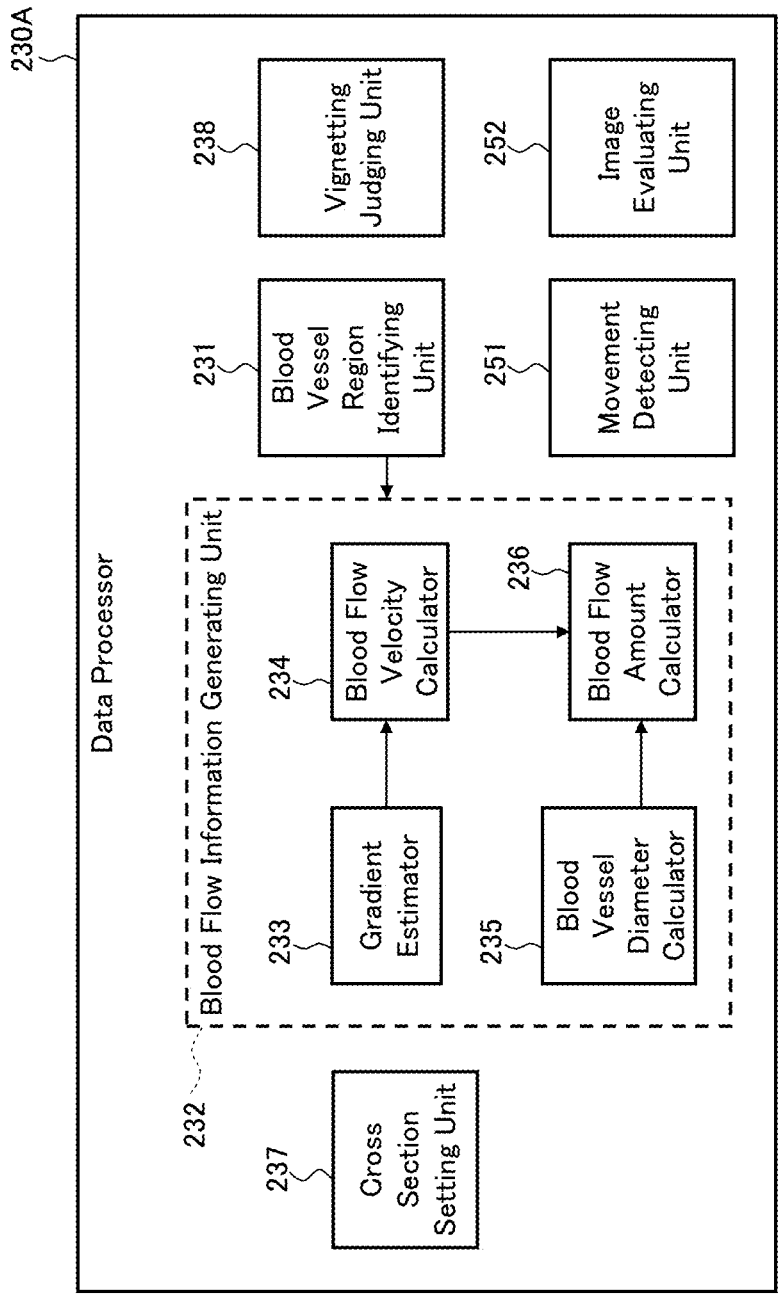
FIG. 10 is a schematic diagram illustrating an example of the configuration of the blood flow measurement apparatus according to the embodiment.

An example of the configuration of the blood flow measurement apparatus according to the present embodiment will be described with reference to FIG. 10. The data processor 230A is employed in place of the data processor 230 (FIG. 3 and FIG. 4) of the first embodiment. In addition, any element other than the data processor 230 among the elements of the blood flow measurement apparatus 1 according to the first embodiment may be applied to the present embodiment. Some elements of the first embodiment will be applied to the description below of the present embodiment as necessary.

The data processor 230A includes the movement detecting unit 251 and the image evaluating unit 252 in addition to the group of elements in the data processor 230 shown in FIG. 4.

The blood flow measurement apparatus according to the present embodiment is capable of acquiring an infrared observation image of the fundus Ef using the observation system (the illumination optical system 10 and the photographing optical system 30). The infrared observation image includes a time series image group (a frame group) acquired at a predetermined time interval.

The movement detecting unit 251 analyzes frames acquired by the observation system to detect the movement of the fundus Ef. The movement detection may be applied to all the frames acquired by the observation system, or may be applied to only part of all the frames acquired by the observation system.

The movement detecting unit 251 performs the first process and the second process. For example, the first process identifies an image region corresponding to a feature site of the fundus Ef (e.g., the optic nerve head, the macula, a blood vessel, a lesion, a laser treatment mark) from a frame. The image region corresponding to the feature site is referred to as a feature region. The second process obtains a temporal change in positions of a plurality of feature regions respectively identified from a plurality of frames. In other words, the second process obtains a temporal change in the depicted position of the feature region in a time series image group.

In some examples, the first process and the second process are executed in real time and in parallel with the acquisition of the infrared observation image using the observation system. The first process is executed to sequentially analyze the frames sequentially acquired by the observation system and sequentially identify the feature region. In addition, the second process is executed to sequentially calculate the shift (displacement) of the depicted position of the feature region between two frames that are temporally adjacent to each other.

The main controller 211 applies control to the movement mechanism 150 to move the optical system (including at least the measurement arm) in accordance with the movement of the fundus Ef detected by the movement detecting unit 251. Thereby, tracking is carried out.

The image evaluating unit 252 evaluates infrared observation images (time series image group, frame group) acquired by the observation system. The evaluation may be an evaluation of whether or not the infrared observation image is appropriate for tracking. In some typical examples, the evaluation includes the judgement of the occurrence of vignetting of the light used for acquiring the infrared observation image. The light here is, for example, the observation illumination light and/or its return light. If vignetting occurs, a decrease in the peripheral light amount of the infrared observation image is detected. The evaluation of the infrared observation image in the present embodiment may be performed, for example, in the same manner as the "second example of the processing executed by the vignetting judging unit 238" described in the first embodiment.

The main controller 211 may execute the second movement control like that of the first embodiment, based on the judgement result obtained by the vignetting judging unit 238 and the evaluation result obtained by the image evaluating unit 252. In the present embodiment as well, the main controller 211 applies the first movement control to the movement mechanism 150 to move the measurement arm by a predetermined distance from the optical axis in the first direction orthogonal to the optical axis of the measurement arm, and also the main controller 211 applies the second movement control to the movement mechanism 150 to further move the measurement arm based on the judgement result obtained by the vignetting judging unit 238.

In short, the present embodiment is configured to perform the second movement control in consideration of both the vignetting judgement and the infrared observation image evaluation. Some examples of such processing will be described below.

The main controller 211 may perform the second movement control to further move the optical system (the measurement arm) in the same first direction as the first movement control if the vignetting judging unit 238 has judged that the vignetting has not occurred and the image evaluating unit 252 has evaluated that the infrared observation image has been appropriate.

On the contrary, the main controller 211 may perform the second movement control to move the optical system (the measurement arm) in a direction opposite to the first direction if the vignetting judging unit 238 has judged that the vignetting has occurred or if the image evaluating unit 2 has evaluated that the infrared observation image is not appropriate.

Further, the main controller 211 may repeatedly perform the second movement control until the following conditions are all satisfied: the vignetting judging unit 238 judges that the vignetting does not occur; the image evaluating unit 252 evaluates that the infrared observation image is appropriate; and the optical system (the objective lens 22 of the measurement arm) is located at a position in which a shift from the position (H0) the optical axis immediately before the first movement control becomes maximum.

According to the present embodiment, the offset operation of the measurement arm for obtaining optimum Doppler signals for the eye fundus blood flow measurement can be performed while performing the tracking in an appropriate manner. Doing so makes it possible to avoid having an error in the offset operation caused by failure in tracking. This contributes to further reduction of the burden on the subject.

Third Embodiment

The blood flow measurement apparatus according to the present embodiment is capable of setting the initial movement amount. The initial movement amount is the movement distance of the optical system in the first movement control and is, for example, the distance between the position H0 and the position H1 in FIG. 9A.

Figure 11:
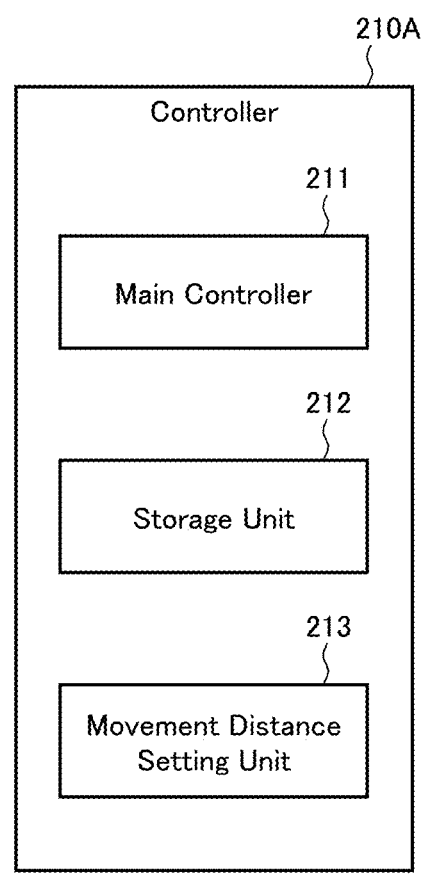
FIG. 11 is a schematic diagram illustrating an example of the configuration of the blood flow measurement apparatus according to the embodiment.

An example of the configuration of the blood flow measurement apparatus according to the present embodiment will be described with reference to FIG. 11. The controller 210A is employed in place of the controller 210 (FIG. 3 and FIG. 4) of the first embodiment. Note that any element other than the controller 210 among the elements of the blood flow measurement apparatus 1 according to the first embodiment may be applied to the present embodiment. Some elements of the first embodiment will be applied to the description below of the present embodiment as necessary. The blood flow measurement apparatus according to the present embodiment may include any one of the data processor 230 and the data processor 230A.

The controller 210A includes the movement distance setting unit 213 in addition to the group of elements inside the controller 210 shown in FIG. 3.

In the cases where the subject's eye E has a small pupil or cataract, or where the blood vessel of interest is located in the peripheral part of the fundus Ef, a drug (a mydriatic agent) may be administered to the subject's eye E for dilating the pupil in some cases. The movement distance setting unit 213 is configured to set the initial movement amount according to whether or not the mydriatic agent has been administered to the subject's eye E. The movement distance setting unit 213 is an example of the first setting unit.

An example will be described of the movement distance setting unit 213. The exemplary movement distance setting unit 213 stores, in advance, the first initial movement amount and the second initial movement amount. The first initial movement amount is an initial movement amount applied to the cases where the mydriatic agent is not administered and the second initial movement amount is a movement distance applied to the cases where the mydriatic agent is administered. The first initial movement amount is set to a value that is a half of a standard pupil diameter (the radius of a pupil of a standard size), for example. The second initial movement amount is set to a value that is a half of the diameter of a dilated pupil after the mydriatic agent has been administered to an eye having a standard pupil diameter. Note that an initial movement amount(s) according to the attributes (age, sex, etc.) of subjects or an initial movement amount(s) according to the attributes of subject's eye may be stored in advance.

The fact whether or not the mydriatic agent has been administered to the subject's eye E may be input by the user using the operation device 242, for example. Alternatively, the fact whether or not the mydriatic agent has been administered may be determined by referring to the electronic medical record of the subject.

The movement distance setting unit 213 selects one of a plurality of stored initial movement amounts based on information indicating whether or not the mydriatic agent has been administered to the subject's eye E. The main controller 211 executes the first movement control with the initial movement amount selected by the movement distance setting unit 213.

According to the present embodiment, the initial movement amount for the first movement control may be set according to the size of the pupil of the subject's eye E (in particular, the pupil diameter according to whether or not the mydriatic agent has been administered). Therefore, the time required for achieving an optimum shift position can further be shortened in the offset operation of the measurement arm for obtaining optimum Doppler signals for the eye fundus blood flow measurement. As a result of this, the burden on the subject can further be reduced.

Fourth Embodiment

The blood flow measurement apparatus according to the present embodiment is capable of setting the initial movement amount (e.g., the distance between the position H0 and the position H1 in FIG. 9A) that is the movement distance of the optical system in the first movement control. Note that the present embodiment is configured to set the initial movement amount according to the actual pupil diameter of the subject's eye E while the third embodiment is configured to set the initial movement amount according to the fact whether or not the mydriatic agent is administered.

Figure 12:
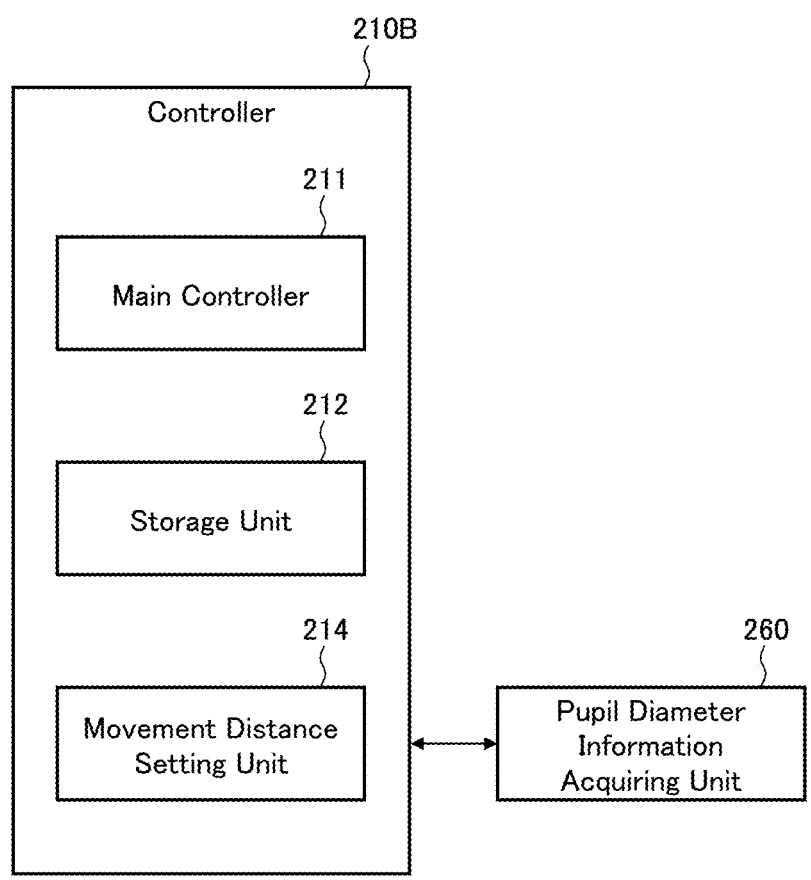
FIG. 12 is a schematic diagram illustrating an example of the configuration of the blood flow measurement apparatus according to the embodiment.

An example of the configuration of the blood flow measurement apparatus according to the present embodiment will be described with reference to FIG. 12. The blood flow measurement apparatus according to the present embodiment includes the pupil diameter information acquiring unit 260. Further, the controller 210B is employed in place of the controller 210 (FIG. 3 and FIG. 4) of the first embodiment. Note that any element other than the controller 210 among the elements of the blood flow measurement apparatus 1 according to the first embodiment may be applied to the present embodiment. Some elements of the first embodiment will be applied to the description below of the present embodiment as necessary. The blood flow measurement apparatus according to the present embodiment may include any one of the data processor 230 and the data processor 230A.

The pupil diameter information acquiring unit 260 is configured to acquire a value of the pupil diameter of the subject's eye E. For example, the pupil diameter information acquiring unit 260 includes an element for measuring the pupil diameter of the subject's eye E. As a specific example thereof, the pupil diameter information acquiring unit 260 may include a processor that analyzes an anterior eye segment image of the subject's eye E acquired by the illumination optical system 10 and the photographing optical system 30 to identify a pupil region, and then calculates the diameter of the pupil region identified. The identification of the pupil region may include a process such as thresholding and/or edge detection. The calculation of the diameter of the pupil region may include a process such as an approximation by ellipse and/or an approximation by circle.

In some other examples, the pupil diameter information acquiring unit 260 acquires, from the electronic medical record of the subject, a measured value of the pupil diameter of the subject's eye E acquired in the past. The pupil diameter information acquiring unit 260 of the present example includes a communication device for accessing an apparatus in which the electronic medical records or the like are stored.

The controller 210B includes the movement distance setting unit 214 in addition to the group of elements in the controller 210 shown in FIG. 3. The movement distance setting unit 214 may set the initial movement amount for the first movement control based on the value of the pupil diameter acquired by the pupil diameter information acquiring unit 260. The movement distance setting unit 214 may set, as the initial movement amount, a value that is a half of the value of the pupil diameter acquired by the pupil diameter information acquiring unit 260, for example. Such an initial movement amount corresponds to the value of the radius of the pupil of the subject's eye E or its approximate value. The movement distance setting unit 214 is an example of the second setting unit.

The main controller 211 executes the first movement control by applying the initial movement amount selected by the movement distance setting unit 214.

According to the present embodiment, the initial movement amount for the first movement control can be set based on the value of the pupil diameter of the subject's eye E actually measured. Therefore, the time required for achieving an optimum shift position can further be shortened in the offset operation of the measurement arm for obtaining optimum Doppler signals for the eye fundus blood flow measurement. This leads to further reduction of the burden on the subject.

The embodiments described above are merely illustrative aspects of the implementation of the present invention. Therefore, any modifications (e.g., omission, substitution, replacement, addition, etc.) may be made within the scope of the present invention.

Fifth Embodiment

Among the elements described in the present embodiment, the same or similar elements as or to those described in any of the first to fourth embodiments are given the same reference characters.

<Configuration>

Figure 13:
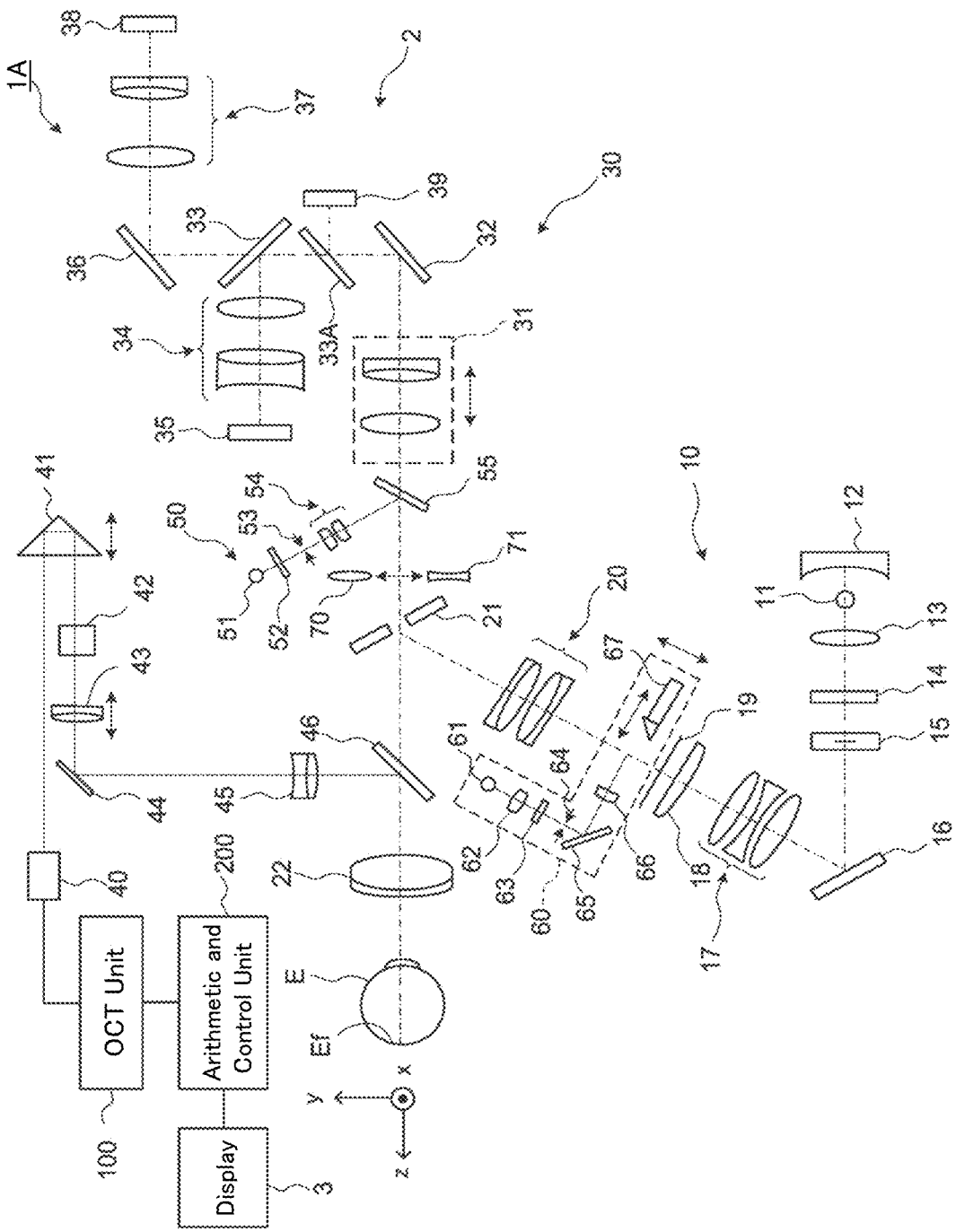
FIG. 13 is a schematic diagram illustrating an example of the configuration of the blood flow measurement apparatus according to the embodiment.

As shown in FIG. 13, the blood flow measurement apparatus 1A includes the fundus camera unit 2, the OCT unit 100 and the arithmetic and control unit 200. The fundus camera unit 2 is provided with an optical system and mechanisms for acquiring front images of the subject's eye. The OCT unit 100 includes part of an optical system and part of mechanisms for performing OCT scanning. Another part of the optical system and another part of the mechanisms for performing OCT scanning are provided in the fundus camera unit 2. The arithmetic and control unit 200 includes one or more processors configured and programmed to execute various calculations and controls. In addition to these, the blood flow measurement apparatus 1A may also include any elements or units such as a member for supporting the face of the subject (e.g., a chin rest, a forehead rest) and a lens unit for switching the sites subjected to OCT scanning (e.g., an attachment for anterior eye segment OCT scanning).

In the present specification, the term "processor" is used to mean, for example, a circuit such as a central processing unit (CPU), a graphics processing unit (GPU), an application specific integrated circuit (ASIC), a programmable logic device (for example, a simple programmable logic device (SPLD), a complex programmable logic device (CPLD), or a field programmable gate array (FPGA)), or the like. The processor realizes the functions according to the embodiment, for example, by reading out and executing a program stored in a storage circuit or a storage device.

<Fundus Camera Unit 2>

The fundus camera unit 2 is provided with an optical system for photographing the fundus Ef of the subject's eye E. Images of the fundus Ef (referred to as fundus images, fundus photographs, or the like) obtained include front images such as observation images and photographed images. An observation image is obtained by capturing a moving image using near-infrared light. A photographed image is a still image obtained by using flash light.

The fundus camera unit 2 includes the illumination optical system 10 and the photographing optical system 30. The illumination optical system 10 projects illumination light onto the subject's eye E. The photographing optical system 30 detects the return light of the illumination light from the subject's eye E. The measurement light incident from the OCT unit 100 is directed to the subject's eye E through the optical path in the fundus camera unit 2, and the return light thereof is directed to the OCT unit 100 through the same optical path.

The light output from the observation light source 11 of the illumination optical system 10 (referred to as observation illumination light) is reflected by the concave mirror 12, passes through the condenser lens 13, and becomes near-infrared light after passing through the visible cut filter 14. Further, the observation illumination light is once converged at a location near the photographing light source 15, reflected by the mirror 16, and passes through the relay lens system 17, the relay lens 18, the diaphragm 19, and the relay lens system 20. Then, the observation illumination light is reflected on the peripheral part (i.e., the surrounding area of the aperture part) of the aperture mirror 21, penetrates the dichroic mirror 46, and refracted by the objective lens 22, thereby illuminating the subject's eye E (the fundus Ef thereof). The return light of the observation illumination light from the subject's eye E is refracted by the objective lens 22, penetrates the dichroic mirror 46, passes through the aperture part formed in the center area of the aperture mirror 21, passes through the dichroic mirror 55, travels through the photography focusing lens 31, and is reflected by the mirror 32. Furthermore, the return light passes through the half mirror 33A, is reflected by the dichroic mirror 33, and forms an image on the light receiving surface of the image sensor 35 by the condenser lens 34. The image sensor 35 detects the return light at a predetermined frame rate. Note that the focus of the photographing optical system 30 is adjusted to coincide with the fundus Ef or the anterior eye segment.

The light output from the photographing light source 15 (referred to as photographing illumination light) passes through the same route as that of the observation illumination light and is projected onto the fundus Ef. The return light of the photographing illumination light from the subject's eye E passes through the same route as that of the return light of the observation illumination light, is guided to the dichroic mirror 33, passes through the dichroic mirror 33, is reflected by the mirror 36, and forms an image on the light receiving surface of the image sensor 38 by the condenser lens 37.

The liquid crystal display (LCD) 39 displays a fixation target (fixation target image). Part of the light beam output from the LCD 39 is reflected by the half mirror 33A, reflected by the mirror 32, travels through the photography focusing lens 31 and the dichroic mirror 55, and passes through the aperture part of the aperture mirror 21. The light beam having passed through the aperture part of the aperture mirror 21 penetrates the dichroic mirror 46, and is refracted by the objective lens 22, thereby being projected onto the fundus Ef.

By changing the display position of the fixation target image on the screen of the LCD 39, the fixation position of the subject's eye E by the fixation target can be changed. Examples of the fixation position includes the followings: a fixation position for acquiring an image centered on the macula; a fixation position for acquiring an image centered on the optic nerve head; a fixation position for acquiring an image centered on the fundus center that is located between the macula and the optic nerve head; and a fixation position for acquiring an image of a site far away from the macula (periphery of the fundus). A user interface such as a graphical user interface (GUI) for designating at least one of such typical fixation positions can be provided. Further, a user interface such as a GUI for manually changing the fixation position (i.e., the display position of the fixation target) can be provided.

The configuration for presenting the fixation target, capable of changing the fixation position, to the subject's eye E is not limited to display devices such as an LCD. For example, a fixation matrix device can be adopted in place of a display device. The fixation matrix device includes a plurality of light emitting parts (e.g., light emitting diodes) that are disposed in a matrix-like arrangement (in a matrix array). In this case, the fixation position of the subject's eye E by the fixation target can be changed by lighting one (or more) of the plurality of light emitting parts in a selective manner. As another example, the fixation target usable for fixation position change may be generated by employing one or more movable light emitting parts.

The alignment optical system 50 generates an alignment indicator used for the alignment of the optical system with respect to the subject's eye E. The alignment light output from the light emitting diode (LED) 51 travels through the diaphragm 52, the diaphragm 53, and the relay lens 54, is reflected by the dichroic mirror 55, passes through the aperture part of the aperture mirror 21, penetrates the dichroic mirror 46, and is projected onto the subject's eye E via the objective lens 22. The return light of the alignment light from the subject's eye E (e.g., the cornea reflection light) passes through the same route as that of the return light of the observation illumination light and is guided to the image sensor 35. Based on the received image, manual alignment and/or automatic alignment can be performed. The received image is referred to as an alignment indicator image.

As in a conventional case, the alignment indicator image of the present example includes two bright spot images whose positions change according to the alignment state. When the relative position between the subject's eye E and the optical system changes in the xy direction, the two bright spot images are shifted in the xy direction in an integrated manner. When the relative position between the subject's eye E and the optical system changes in the z direction, the relative position (distance) between the two bright spot images changes. When the distance between the subject's eye E and the optical system in the z direction matches with a working distance set in advance, the two bright spot images overlap with each other. When the position of the subject's eye E matches with the position of the optical system in the xy direction, the two bright spot images are presented within or near a given alignment target. When the distance between the subject's eye E and the optical system in the z direction matches with the working distance, and the position of the subject's eye E matches with the position of the optical system in the xy direction, the two bright spot images overlap with each other and are presented within the alignment target.

For the automatic alignment, the data processor 230 detects the positions of the two bright spot images, and the main controller 211 controls the movement mechanism 150 (described later) on the basis of the positional relationship between the two bright spot images and the alignment target. In the manual alignment, the main controller 211 displays the two bright spot images together with the observation image of the subject's eye E on the display 241, and the user operates the movement mechanism 150 using the operation device 242 while referring to the two bright spot images displayed.

The focus optical system 60 generates a split indicator used for the focus adjustment with respect to the subject's eye E. In conjunction with the movement of the photography focusing lens 31 along the optical path of the photographing optical system 30 (referred to as the photographing optical path), the focus optical system 60 is moved along the optical path of the illumination optical system 10 (referred to as the illumination optical path). The reflection rod 67 is inserted into and removed from the illumination optical path. Before performing focus adjustment, the reflective surface of the reflection rod 67 is arranged in the slanted state in the illumination optical path. The focus light output from the LED 61 passes through the relay lens 62, is split into two light beams by the split indicator plate 63, passes through the two-hole diaphragm 64. The focus light, then, is reflected by the mirror 65, is converged on the reflective surface of the reflection rod 67 by the condenser lens 66, and is reflected by the reflective surface. Further, the focus light travels through the relay lens 20, is reflected by the aperture mirror 21, and penetrates the dichroic mirror 46, thereby being projected onto the subject's eye E via the objective lens 22. The return light of the focus light from the subject's eye E (the fundus reflection light, etc.) passes through the same route as that of the return light of the alignment light and is guided to the image sensor 35. Based on the received image, manual focusing and/or automatic focusing can be performed. The received image is referred to as a split indicator image.

The diopter correction lenses 70 and 71 can be selectively inserted into the photographing optical path between the aperture mirror 21 and the dichroic mirror 55. The diopter correction lens 70 is a positive lens (convex lens) for correcting high hyperopia. The diopter correction lens 71 is a negative lens (concave lens) for correcting high myopia.

The dichroic mirror 46 couples the optical path for fundus photography and the optical path for OCT scanning (measurement arm). The dichroic mirror 46 reflects the light of wavelength bands used for OCT scanning and transmits the light for fundus photography. Listed from the OCT unit 100 side, the collimator lens unit 40, the retroreflector 41, the dispersion compensation member 42, the OCT focusing lens 43, the optical scanner 44, and the relay lens 45 are arranged in the measurement arm.

The retroreflector 41 is movable in the directions indicated by the arrow in FIG. 13, whereby the length of the measurement arm is changed. The change in the optical path length of the measurement arm may be utilized for correcting the optical path length according to the axial length, and for adjusting the interference condition, for example.

Together with the dispersion compensation member 113 (described later) arranged in the reference arm, the dispersion compensation member 42 acts to equalize the dispersion characteristics of the measurement light LS and the dispersion characteristics of the reference light LR with each other.

The OCT focusing lens 43 is moved along the measurement arm in order to perform the focus adjustment of the measurement arm. The movement of the photography focusing lens 31, the movement of the focus optical system 60, and the movement of the OCT focusing lens 43 may be controlled in an interlocking manner.

The optical scanner 44 is placed substantially at a position optically conjugate with the pupil of the subject's eye E. The optical scanner 44 deflects the measurement light LS guided through the measurement arm. The optical scanner 44 is, for example, a galvanometer scanner capable of two dimensional scanning.

<OCT Unit 100>

Figure 14:
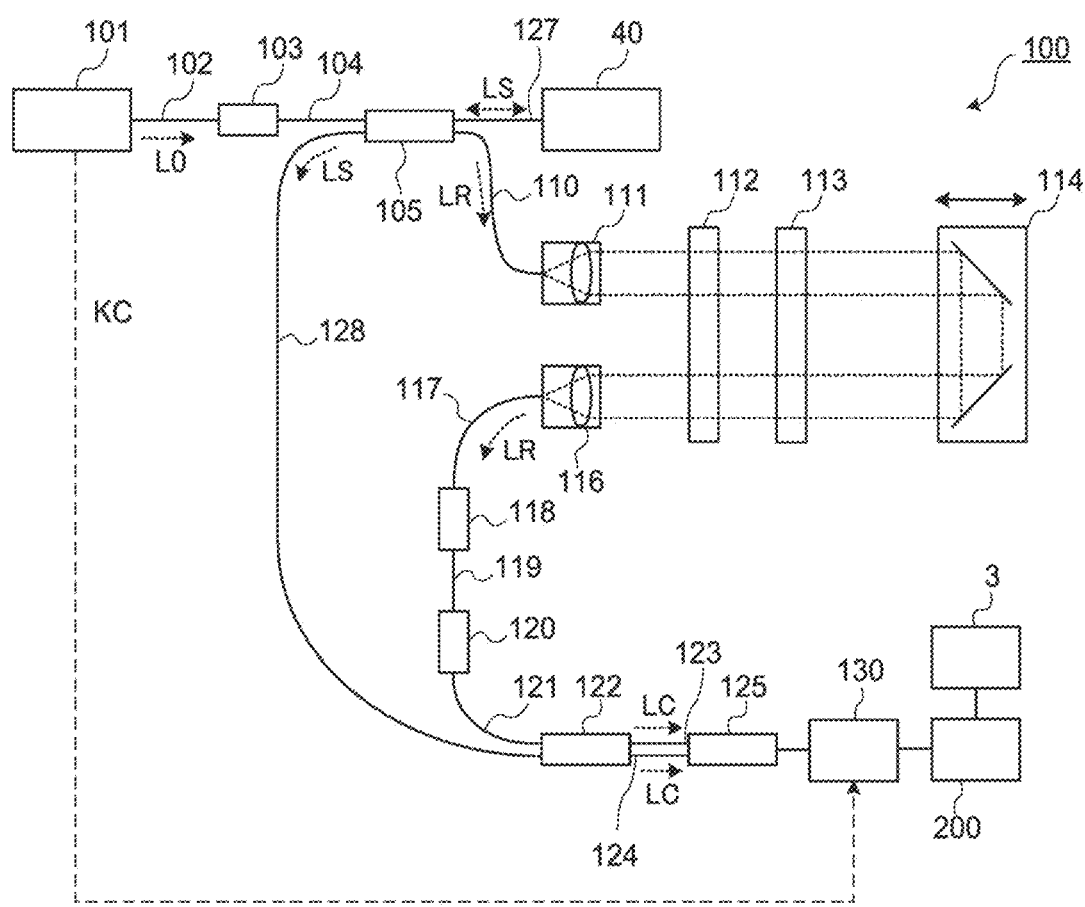
FIG. 14 is a schematic diagram illustrating an example of the configuration of the blood flow measurement apparatus according to the embodiment.

As illustrated in FIG. 14, the OCT unit 100 is provided with the optical system for performing swept source OCT. The optical system includes an interference optical system. The interference optical system is configured to split the light emitted from the light source of wavelength tunable type (or wavelength sweeping type) into measurement light and reference light, superpose the return light of the measurement light from the subject's eye E and the reference light having traveled through the reference optical path to generate interference light, and detect the interference light. The detection result (i.e., detection signal) obtained by the interference optical system is a signal representing a spectrum of the interference light. The detection signal is sent to the arithmetic and control unit 200.

The light source unit 101 includes, for example, a near infrared tunable laser configured to change the wavelengths of emitted light at high speed. The light L0 output from the light source unit 101 is guided to the polarization controller 103 through the optical fiber 102, and the polarization state of the light L0 is regulated. Further, the light L0 is guided to the fiber coupler 105 through the optical fiber 104 and is split into the measurement light LS and the reference light LR. The optical path of the measurement light LS is referred to as a measurement arm, a sample arm, or the like, and the optical path of the reference light LR is referred to as a reference arm or the like.

The reference light LR is guided through the optical fiber 110 to the collimator 111, is converted into a parallel light beam, travels through the optical path length correction member 112 and the dispersion compensation member 113, and is guided to the retroreflector 114. The optical path length correction member 112 acts to match the optical path length of the reference light LR and the optical path length of the measurement light LS with each other. The dispersion compensation member 113 acts to equalize the dispersion characteristics of the reference light LR and the dispersion characteristics of the measurement light LS with each other, together with the dispersion compensation member 42 arranged in the measurement arm. The retroreflector 114 is movable along the optical path of the reference light LR incident on the retroreflector 114. With this, the length of the reference arm is changed. The change in the optical path length of the reference arm can be utilized, for example, for the correction of the optical path length according to the axial length, and for the regulation of the interference condition.

The reference light LR that has passed through the retroreflector 114 travels through the dispersion compensation member 113 and the optical path length correction member 112, is converted from a parallel light beam to a convergent light beam by the collimator 116, and is incident on the optical fiber 117. The reference light LR incident on the optical fiber 117 is guided to the polarization controller 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided through the optical fiber 127 and is converted to a parallel light beam by the collimator lens unit 40. Then, the measurement light LS passes through the retroreflector 41, the dispersion compensation member 42, the OCT focusing lens 43, the optical scanner 44, and the relay lens 45, and then reaches the dichroic mirror 46. The measurement light LS is reflected by the dichroic mirror 46, is refracted by the objective lens 22, and is projected onto the subject's eye E. The measurement light LS is reflected and scattered at various depth positions of the subject's eye E. The return light of the measurement light LS from the subject's eye E travels along the same route as the outward way in the opposite direction, is directed to the fiber coupler 105, and then reaches the fiber coupler 122 via the optical fiber 128.

The fiber coupler 122 superposes the measurement light LS incident through the optical fiber 128 and the reference light LR incident through the optical fiber 121 with each other, to generate interference light. The fiber coupler 122 splits the generated interference light at a predetermined splitting ratio (e.g., 1 to 1) to generate a pair of interference light LC. The pair of the interference light LC is guided to the detector 125 through the optical fibers 123 and 124, respectively.

The detector 125 includes, for example, a balanced photo diode. The balanced photodiode includes a pair of photodetectors for respectively detecting the pair of the interference light LC. The balanced photodiode outputs the difference between the pair of detection results obtained by the pair of photodetectors. The detector 125 sends the output (i.e., detection signal) to the data acquisition system (DAQ) 130.

The clock KC is supplied from the light source unit 101 to the data acquisition system 130. The clock KC is generated in the light source unit 101 in synchronization with the output timings of the respective wavelengths varied within a predetermined wavelength range by the wavelength tunable type light source. For example, the light source unit 101 splits the light L0 of each output wavelength to generate two pieces of split light, optically delays one of the two pieces of split light, combines the two pieces of split light, detects the combined light obtained, and generates the clock KC based on the result of the detection of the combined light. The data acquisition system 130 performs the sampling of the detection signal input from the detector 125 based on the clock KC. The data acquisition system 130 sends the result of the sampling of the detection signal from the detector 125 to the arithmetic and control unit 200.

The present example is provided with both an element for changing the optical path length of the measurement arm (e.g., the retroreflector 41) and an element for changing the optical path length of the reference arm (e.g., the retroreflector 114 or a reference mirror). However, only one of these elements may be provided in other embodiments. Elements for changing the difference between the optical path length of the measurement arm and the optical path length of the reference arm (i.e., elements for changing the optical path length difference) are not limited to the aforesaid elements, and may be any type of element such as any type of optical members and any type of mechanisms.

<Processing System>

Figure 15:
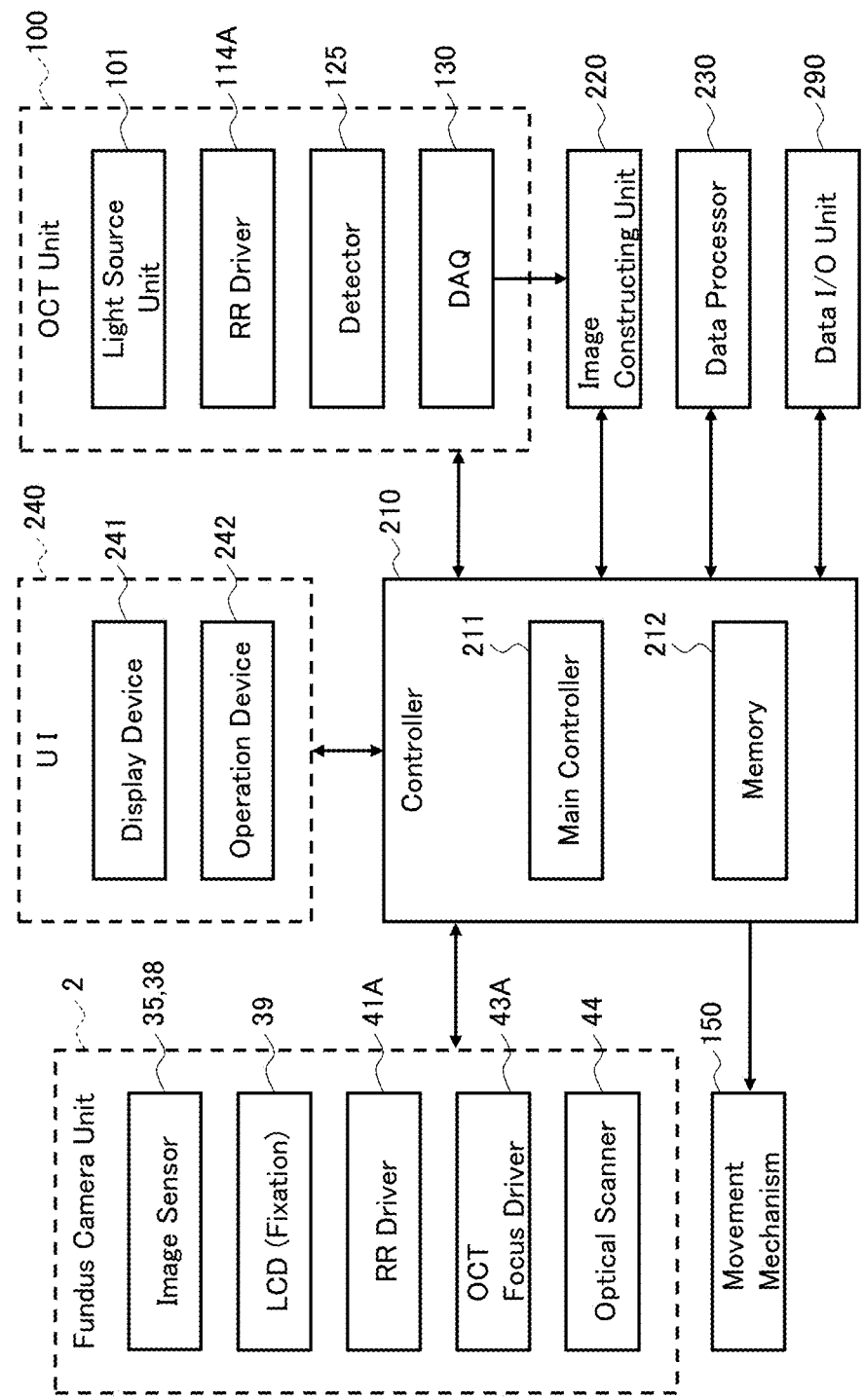
FIG. 15 is a schematic diagram illustrating an example of the configuration of the blood flow measurement apparatus according to the embodiment.
Figure 16:
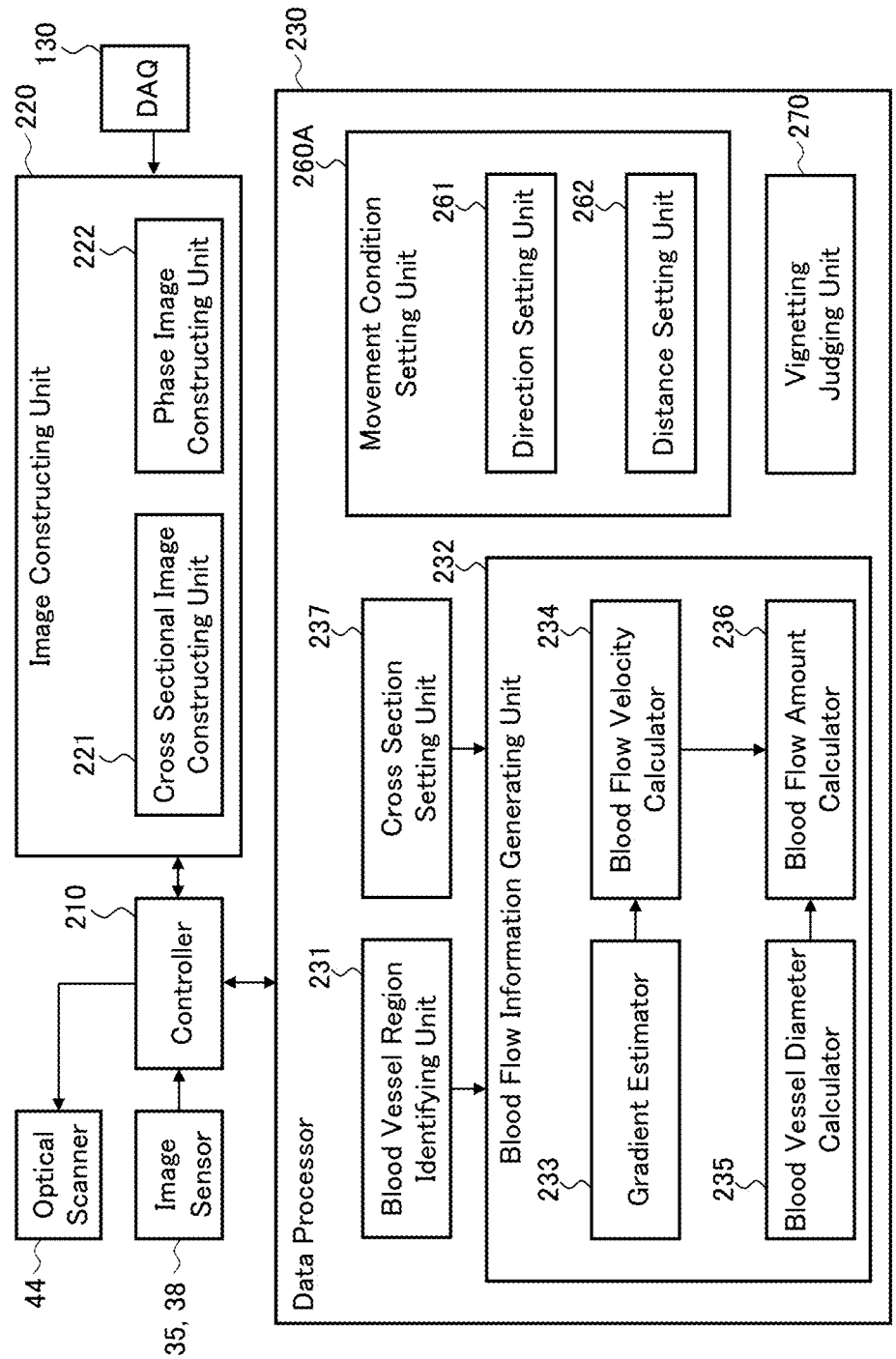
FIG. 16 is a schematic diagram illustrating an example of the configuration of the blood flow measurement apparatus according to the embodiment.

FIG. 15 and FIG. 16 show an example of the configuration of the processing system (arithmetic and control system) of the blood flow measurement apparatus 1A. The controller 210, the image constructing unit 220 and the data processor 230 are provided in the arithmetic and control unit 200.

<Controller 210>

The controller 210 performs various kinds of controls. The controller 210 includes the main controller 211 and the memory 212.

<Main Controller 211>

The main controller 211 includes a processor configured and programmed to operate according to a control program, and controls each unit and element of the blood flow measurement apparatus 1A (including the units and elements shown in FIG. 13 to FIG. 16).

The photography focusing lens 31 disposed in the photographing optical path and the focus optical system 60 disposed in the illumination optical path are moved in a synchronized manner by a photographing focus driver (not shown in the figures) under the control of the main controller 211. The retroreflector 41 disposed in the measurement arm is moved by the retroreflector driver (RR driver) 41A under the control of the main controller 211. The OCT focusing lens 43 disposed in the measurement arm is moved by the OCT focus driver 43A under the control of the main controller 211. The optical scanner 44 disposed in the measurement arm operates under the control of the main controller 211. The retroreflector 114 disposed in the reference arm is moved by the retroreflector driver (RR driver) 114A under the control of the main controller 211. Each of the aforesaid drivers includes an actuator such as a pulse motor which operates under the control of the main controller 211.

The movement mechanism 150 moves, for example, at least the fundus camera unit 2 in a three dimensional manner. In a typical example, the movement mechanism 150 includes the followings: an x stage movable in the ±x direction (i.e., left and right direction); an x movement mechanism that moves the x stage; a y stage movable in the ±y direction (i.e., up and down direction); a y movement mechanism that moves the y stage; a z stage movable in the ±z direction (i.e., depth direction); and a z movement mechanism that moves the z stage. Each of the aforesaid movement mechanisms includes an actuator such as a pulse motor which operates under the control of the main controller 211.

The main controller 211 controls the LCD 39. For example, the main controller 211 displays the fixation target at a preset position on the screen of the LCD 39. Further, the main controller 211 may change the display position of the fixation target displayed on the LCD 39. That is, the main controller 211 may change the fixation position. The fixation target movement may be performed in any manner such as continuous movement, intermittent movement, and discrete movement. Some examples of manners of moving the fixation position in the present embodiment will be described later.

The fixation position is represented by the display position (the pixel coordinates) of the fixation target image on the LCD 39, for example. The pixel coordinates are defined, for example, by using coordinates represented by a two dimensional coordinate system predefined on the display screen of the LCD 39. If the aforementioned fixation matrix device is used, the fixation position is represented, for example, by the position (coordinates) of the light emitting part lit for fixation. The coordinates of that light emitting part are, for example, the coordinates represented by a two dimensional coordinate system defined in advance on the plane on which the plurality of light emitting parts are arranged.

<Memory 212>

The memory 212 stores various kinds of data. Examples of the data stored in the memory 212 include OCT images, fundus images, and subject's eye information. The subject's eye information includes subject information such as the patient ID and the patient's name, identification information for the left eye and the right eye, and electronic medical record information.

<Image Constructing Unit 220>

The image constructing unit 220 constructs OCT image data of the fundus Ef based on the signal (sampling data, or sampled data) input from the data acquisition system 130. The image constructing unit 220 may construct B-scan image data (i.e., two dimensional cross sectional image data) and phase image data of the fundus Ef. These pieces of OCT image data will be described later. The image constructing unit 220 includes, for example, a processor configured and programmed to operate according to an image constructing program. In the present specification, "image data" and an "image" displayed or rendered based thereon may not be distinguished from one another unless otherwise mentioned.

The blood flow measurement of the present embodiment performs two types of scans on the fundus Ef. The two types of scans will be referred to as a main scan and a supplementary scan.

The main scan performs repetitive scanning (iterative scanning), with the measurement light LS, on a cross section of the fundus Ef that intersects a blood vessel of interest in order to acquire phase image data. The cross section of the fundus Ef that intersects a blood vessel of interest is referred to as a cross section of interest.

The supplementary scan performs a scan on a predetermined cross section with the measurement light LS in order to estimate the gradient (or, inclination, tilt, slope, slant, or the like) of the blood vessel of interest at the cross section of interest. The cross section to which the supplementary scan is applied is referred to as a supplementary cross section. In some examples, the supplementary cross section may be a cross section that intersects the blood vessel of interest and is located in the vicinity of the cross section of interest. Such a supplementary cross section is referred to as the first supplementary cross section. In some other examples, the supplementary cross section may be a cross section that intersects the cross section of interest and is oriented along the blood vessel of interest. Such a supplementary cross section is referred to as the second supplementary cross section.

Figure 17A:
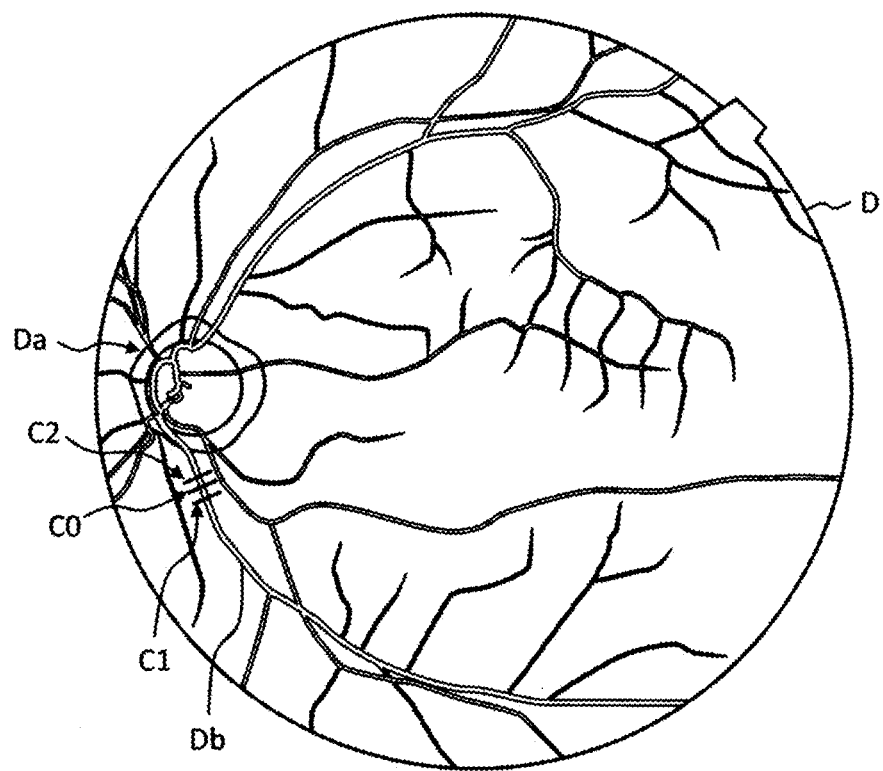
FIG. 17A is a schematic diagram for describing an example of the operation of the blood flow measurement apparatus according to the embodiment.

FIG. 17A shows an example in which the first supplementary cross section is employed. In the present example, as shown on the fundus image D, one cross section of interest C0 and two supplementary cross sections C1 and C2 are set to intersect the blood vessel of interest db. Here, the cross section of interest C0 is located near the optic nerve head Da of the fundus Ef, and the supplementary cross sections C1 and C2 are located near the cross section of interest C0. One of the two supplementary cross sections C1 and C2 is located on the upstream side of the blood vessel of interest db with respect to the cross section of interest C0, and the other is located on the downstream side. The cross section of interest C0 and the supplementary cross sections C1 and C2 are each oriented to be substantially orthogonal to the running direction of the blood vessel of interest db, for example.

Figure 17B:
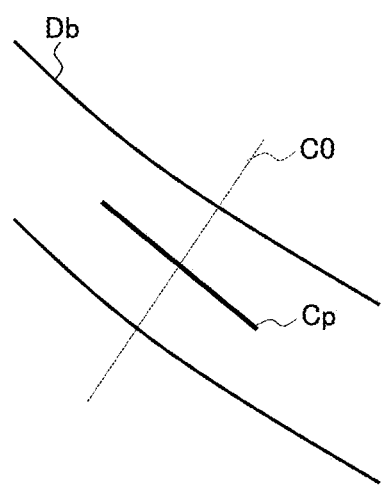
FIG. 17B is a schematic diagram for describing an example of the operation of the blood flow measurement apparatus according to the embodiment.

FIG. 17B shows an example in which the second supplementary cross section is employed. Similar to the above example shown in FIG. 17A, the cross section of interest C0 is set to be substantially orthogonal to the blood vessel of interest db in the present example. Further, in the present example, the supplementary cross section Cp is set to be substantially orthogonal to the cross section of interest C0. The supplementary cross section Cp is oriented along the blood vessel of interest db. As an example, the supplementary cross section Cp may be set to pass through the intersection between the central line of the blood vessel of interest db and the cross section of interest C0.

In the exemplary blood flow measurement, the main scan performs repetitive scanning over a period of time containing at least one cardiac cycle of the patient's heart. This makes it possible to obtain hemodynamics information for all cardiac phases. The period of time during which the main scan is performed may be a fixed length of time set in advance, or a length of time set for a target patient or an examination to be conducted. In the former case (fixed length of time), a period of time longer than the standard cardiac cycle is set (e.g., 2 seconds). In the latter case (non-fixed length of time), biometric data (medical parameters) such as the patient's electrocardiogram may be referred to. Here, any factor other than cardiac cycles may be considered. Examples of such factors include the length of time required for conduction of examination (e.g., burden on patients), the response time of the optical scanner 44 (e.g., scanning time interval), the response time of the detector 125 (e.g., scanning time interval), and the like.

The image constructing unit 220 includes the cross sectional image constructing unit 221 and the phase image constructing unit 222.

<Cross Sectional Image Constructing Unit 221>

The cross sectional image constructing unit 221 constructs cross sectional images that represent a temporal change (or, temporal variation, chronological change, chronological variation, time course, or the like) in the morphology (or structure) of the cross section of interest, based on sampling data obtained by the data acquisition system 130 with the main scan. Such a cross sectional image is referred to as a main cross sectional image. This cross sectional image construction process will be described in more detail. As described above, the main scan performs repetitive scanning on the cross section of interest C0. Sampling data is sequentially input from the data acquisition system 130 to the cross sectional image constructing unit 221 in response to the repetition of scans. The cross sectional image constructing unit 221 constructs one main cross sectional image corresponding to the cross section of interest C0, based on the sampling data corresponding to one scan performed on the cross section of interest C0. The cross sectional image constructing unit 221 repeats such processing as many times as the number of repetition of scans in the main scan, to construct a series of main cross sectional images in time series. Here, these main cross sectional images may be put into a plurality of groups, and then two or more main cross sectional images belonging to one group may be synthesized or composed to create an image having an improved image quality. Such processes are referred to as image averaging.

Further, the cross sectional image constructing unit 221 constructs a cross sectional image that represents the morphology (or structure) of the supplementary cross section, based on sampling data obtained by the data acquisition system 130 with the supplementary scan for the supplementary cross section(s). Such a cross sectional image is referred to as a supplementary cross sectional image. The supplementary cross sectional image constructing process may be executed in the same manner as the main cross sectional image constructing process described above. Here, the main cross sectional image is a series of cross sectional images in time series, but the supplementary cross sectional image may be one cross sectional image. Further, the supplementary cross sectional image may be an image having an improved image quality created by synthesizing or composing a plurality of cross sectional images acquired by a plurality of scans on the supplementary cross section (image averaging).

When the supplementary cross sections C1 and C2 illustrated in FIG. 17A are employed, the cross sectional image constructing unit 221 constructs a supplementary cross sectional image corresponding to the supplementary cross section C1 and a supplementary cross sectional image corresponding to the supplementary cross section C2. On the other hand, when the supplementary cross section Cp illustrated in FIG. 17B is employed, the cross sectional image constructing unit 221 constructs a supplementary cross sectional image corresponding to the supplementary cross section Cp.

The process of constructing a cross sectional image as described thus far includes noise elimination (noise reduction), filtering, and fast Fourier transform (FFT), as in conventional Fourier domain OCT. By applying fast Fourier transform, sampling data obtained by the data acquisition system 130 (i.e., interference signal, interferogram) is converted into an A-line profile. Such an A-line profile is a reflection intensity profile along the z direction. By performing imaging process on the A-line profile, that is, by assigning pixel values to the reflection intensity values in the A-line profile, an A-scan image is generated. Further, a two dimensional cross sectional image such as a B-scan image or a circle scan image is constructed by arranging a plurality of A-scan images thus generated according to the scan pattern. In the cases where an OCT apparatus of another type is employed, the cross sectional image constructing unit 221 executes a known process according to the type of OCT apparatus employed.

<Phase Image Constructing Unit 222>

The phase image constructing unit 222 constructs a phase image that represents a temporal change (or, temporal variation, chronological change, chronological variation, time course, or the like) in the phase differences in the cross section of interest, based on sampling data obtained by the data acquisition system 130 with the main scan. The sampling data used for constructing the phase image may be the same as the sampling data used for constructing the main cross sectional image by the cross sectional image constructing unit 221. Doing so makes it possible to perform registration between the main cross sectional image and the phase image. In other words, a natural correspondence may be defined between the pixels of the main cross sectional image and the pixels of the phase image.

An example will be described of a method of constructing such phase images. A phase image in the present example is obtained by calculating the phase difference between adjacent A-line complex signals (that is, signals corresponding to mutually adjacent scan points). In other words, the phase image in the present example is constructed based on the temporal change in the pixel values (brightness values) of the main cross sectional image. For an arbitrary pixel of the main cross sectional image, the phase image constructing unit 222 creates a graph of the temporal change in the brightness value of that pixel. The phase image constructing unit 222 determines the phase difference $\Delta\varphi$ between two time points t1 and t2 separated by a predetermined time interval $\Delta t$ in the graph created (t2=t1+$\Delta t$). Then, the phase difference $\Delta\varphi$ is defined as the phase difference $\Delta\varphi$ (t1) at the time point t1. More generally, the phase difference $\Delta\varphi$ may be defined as the phase difference at an arbitrary time point between the time points t1 and t2. By performing this process for each of a large number of time points set in advance, a temporal change in the phase difference for that pixel is obtained.

A phase image is an image representation of phase difference values of each pixel at each time point. This imaging process may be realized, for example, by representing the values of the phase difference with display colors or brightness. When applying such image representation, a display color indicating that a phase has increased in time series may be different from a display color indicating that a phase has decreased in time series. For example, red is assigned to phase increase, and blue is assigned to phase decrease. Further, the magnitude of the amount of change in a phase may be represented by the density of display colors. By adopting representation methods as described above, the direction and quantity of blood flow may be clearly indicated using display colors. A phase image is constructed by executing the above processing for each pixel.

Note that the temporal change in phase difference may be obtained by sufficiently reducing the time interval Δt described above to secure the correlation in phases. Here, oversampling may be performed in which the time interval Δt is set to a value less than the time period corresponding to the resolution of a cross sectional image in the scanning of the measurement light LS.

<Data Processor 230>

The data processor 230 performs various kinds of data processing. For example, the data processor 230 applies various kinds of image processing and/or various kinds of analysis processing, to an image constructed by the image constructing unit 220. As a specific example, the data processor 230 executes various kinds of correction processing such as brightness correction of an image and/or dispersion correction of an image. Further, the data processor 230 may perform various kinds of image processing and/or various kinds of analysis processing, on an image obtained by the fundus camera unit 2 (e.g., a fundus image, an anterior eye segment image), an image input from the outside, or other images.

The data processor 230 may construct three dimensional image data of the fundus Ef. Three dimensional image data means image data in which the positions of pixels are defined using a three dimensional coordinate system. Stack data and volume data are examples of such three dimensional image data.

Stack data is image data constructed by arranging a plurality of cross sectional images respectively obtained for a plurality of scan lines in a three dimensional fashion, based on the positional relationship of the scan lines. In other words, stack data is image data constructed by representing a plurality of cross sectional images, which are originally defined using mutually different two dimensional coordinate systems, using a common three dimensional coordinate system. In further other words, stack data is image data constructed by embedding such a plurality of cross sectional images in a common three dimensional space.

Volume data is image data whose picture elements are voxels that are arranged in a three dimensional manner. Volume data is also referred to as voxel data. Volume data is constructed by applying known interpolation, voxelization, or the like, to stack data.

The data processor 230 may construct an image to be displayed, by applying rendering to three dimensional image data. Examples of applicable rendering methods and techniques include volume rendering, surface rendering, maximum intensity projection (MIP), minimum intensity projection (MinIP), and multi planar reconstruction (MPR).

The data processor 230 includes the following exemplary elements for obtaining blood flow information: the blood vessel region identifying unit 231, the blood flow information generating unit 232, and the cross section setting unit 237. The blood flow information generating unit 232 includes the gradient estimator 233, the blood flow velocity calculator 234, the blood vessel diameter calculator 235, and the blood flow amount calculator 236.

<Blood Vessel Region Identifying Unit 231>

For each of the main cross sectional image, the supplementary cross sectional image, and the phase image, the blood vessel region identifying unit 231 identifies a blood vessel region in that image corresponding to the blood vessel of interest db. This processing may be performed by analyzing the pixel values of the image (e.g., thresholding).

Note that although the main cross sectional image and the supplementary cross sectional image have sufficient resolution to be subjected to analysis processing, the phase image may not have resolution enough to identify the boundary of a blood vessel region in some cases. However, since blood flow information is generated based on the phase image, it is necessary to identify a blood vessel region included therein with high precision and high accuracy. To do so, for example, the following processes may be employed to more accurately identify a blood vessel region in the phase image.

As described above, the main cross sectional image and the phase image are constructed from the same sampling data. Therefore, a natural correspondence between the pixels of the main cross sectional image and the pixels of the phase image may be established. For example, the blood vessel region identifying unit 231 may be configured to perform the following processes to identify a blood vessel region in the phase image: analyzing the main cross sectional image to identify a blood vessel region therein; identifying an image region in the phase image corresponding to the blood vessel region identified in the main cross sectional image based on the pixel correspondence described above; and adopting the image region identified in the phase image as a blood vessel region therein. Such processed make it possible to identify a blood vessel region in the phase image with high precision and high accuracy.

<Blood Flow Information Generating Unit 232>

The blood flow information generating unit 232 generates blood flow information on the blood vessel of interest db. As described above, the blood flow information generating unit 232 includes the gradient estimator 233, the blood flow velocity calculator 234, the blood vessel diameter calculator 235, and the blood flow amount calculator 236.

<Gradient Estimator 233>

The gradient estimator 233 derives an estimated value of the gradient of the blood vessel of interest db based on data of the supplementary cross section (e.g., cross sectional data, supplementary cross sectional image) acquired by the supplementary scan described above. The estimated gradient value may be, for example, a measured value or an approximate value of the gradient of the blood vessel of interest db at the cross section of interest.

An example is described of the case in which the gradient value of the blood vessel of interest db is actually measured (the first example of gradient estimation). In the cases where the supplementary cross sections C1 and C2 shown in FIG. 17A are applied, the gradient estimator 233 may calculate the gradient value of the blood vessel of interest db at the cross section of interest C0, based on the positional relationship between the cross section of interest C0, the supplementary cross section C1, and the supplementary cross section C2, and further based on the result of identification of the blood vessel regions obtained by the blood vessel region identifying unit 231.

A method of calculating the gradient of the blood vessel of interest db will be described with reference to FIG. 18A. The reference characters G0, G1 and G2 indicate the main cross sectional image at the cross section of interest C0, the supplementary cross sectional image at the supplementary cross section C1, and the supplementary cross sectional image at the supplementary cross section C2, respectively. The reference characters V0, V1 and V2 indicate a blood vessel region in the main cross sectional image G0, a blood vessel region in the supplementary cross sectional image G1, and a blood vessel region in the supplementary cross sectional image G2, respectively. The z coordinate axis shown in FIG. 18A substantially coincides with the incident direction of the measurement light LS. Further, the distance between the main cross sectional image G0 (the cross section of interest C0) and the supplementary cross sectional image G1 (the supplementary cross section C1) is denoted by d, and the distance between the main cross sectional image G0 (the cross section of interest C0) and the supplementary cross sectional image G2 (the supplementary cross section C2) is also denoted by d. The interval between adjacent cross sectional images, that is, the interval between adjacent cross sections is referred to as a distance between cross sections.

The gradient estimator 233 may calculate the gradient A of the blood vessel of interest db at the cross section of interest C0 based on the positional relationship between the three blood vessel regions V0, V1 and V2. This positional relationship is determined, for example, by connecting the three blood vessel regions V0, V1 and V2. As a specific example, the gradient estimator 233 may identify feature positions respectively of the three blood vessel regions V0, V1 and V2, and connect the feature positions. Examples of such a feature position include a center position, a center of gravity position, an uppermost location (i.e., the position having the smallest z coordinate value), a lowermost location (i.e., the position having the largest z coordinate value), and the like. Among these examples of feature positions, the identification of the uppermost location is considered to be the simplest processing. In addition, examples of methods of connecting the feature positions include a method of connecting with a line segment, a method of connecting with an approximate curve (e.g., spline curve, Bezier curve), and the like.

Further, the gradient estimator 233 calculates the gradient A based on the lines connecting the feature positions identified from the three blood vessel regions V0, and V2. When connecting with line segments, for example, the gradient A may be calculated based on the gradient of the first line segment and the gradient of the second line segment. Here, the first line segment connects the feature position of the cross section of interest C0 and the feature position of the supplementary cross section C1, and the second line segment connects the feature position of the cross section of interest C0 and the feature position of the supplementary cross section C2. An example of this calculation processing may be operated to calculate the average value of the gradients of the two line segments. On the other hand, an example of connecting with an approximate curve may be operated to calculate the gradient of the approximate curve at the position where the approximate curve intersects the cross section of interest C0. Note that the distance between cross sections d may be used, for example, when the cross sectional images G0 to G2 are embedded in the xyz coordinate system in the process of determining a line segment or an approximate curve.

In the above examples, the blood vessel regions in three cross sections are taken into consideration; however, other examples may take two cross sections into consideration to calculate the gradient. As a specific example thereof, one of the gradient of the first line segment and the gradient of the second line segment mentioned above may be selected as a targeted gradient. Furthermore, the gradient A of the blood vessel of interest db at the cross section of interest C0 may be calculated based on the two supplementary cross sectional images G1 and G2.

In the above examples, a single value of the gradient is obtained, but two or more values of the gradient may be obtained respectively for two or more positions (or regions) in the blood vessel region V0. If this is the case, the two or more gradient values obtained may be used separately. Alternatively, the two or more gradient values obtained may be subjected to statistical processing to derive a statistic (e.g., the mean value, the maximum value, the minimum value, the median, the mode), and the statistic may be used as the gradient A.

An example is described of the case in which an approximate value of the gradient of the blood vessel of interest is calculated (the second example of gradient estimation). In the event that the supplementary cross section Cp shown in FIG. 17B is applied, the gradient estimator 233 may analyze the supplementary cross sectional image corresponding to the supplementary cross section Cp to calculate an approximate value of the gradient of the blood vessel of interest db at the cross section of interest C0.

A method of approximating the gradient of the blood vessel of interest db will be described with reference to FIG. 18B. The reference character Gp denotes a supplementary cross sectional image of the supplementary cross section Cp. The reference character A denotes the gradient of the blood vessel of interest db at the cross section of interest C0, as in the example shown in FIG. 18A.

In the present example, the gradient estimator 233 may identify an image region corresponding to a predetermined tissue of the fundus Ef by analyzing the supplementary cross sectional image Gp. For example, the gradient estimator 233 may identify an image region M corresponding to the inner limiting membrane (ILM) that is a surface tissue of the retina. The image region M is referred to as an inner limiting membrane region. For example, any known segmentation processing may be used for the image region identification.

It is known that the internal limiting membrane and fundus blood vessels are substantially parallel to each other. The gradient estimator 233 calculates the gradient $A_{app}$ of the inner limiting membrane region M at the cross section of interest C0. The gradient $A_{app}$ of the inner limiting membrane region M at the cross section of interest C0 may be used as an approximate value of the gradient A of the blood vessel of interest db at the cross section of interest C0.

Figure 18A:
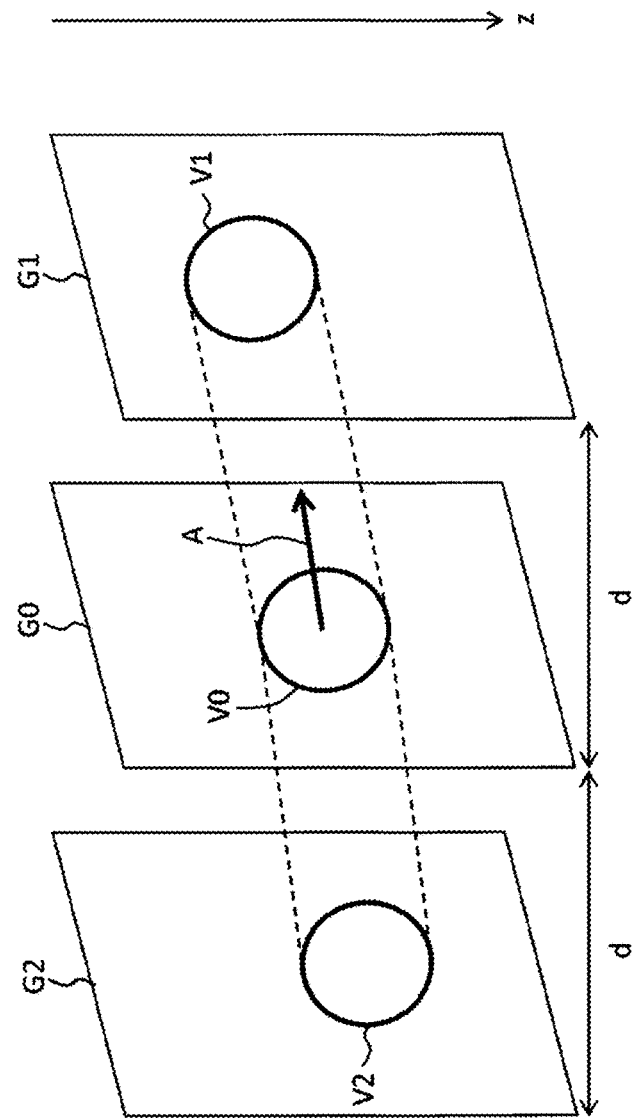
FIG. 18A is a schematic diagram for describing an example of the operation of the blood flow measurement apparatus according to the embodiment.
Figure 18B:
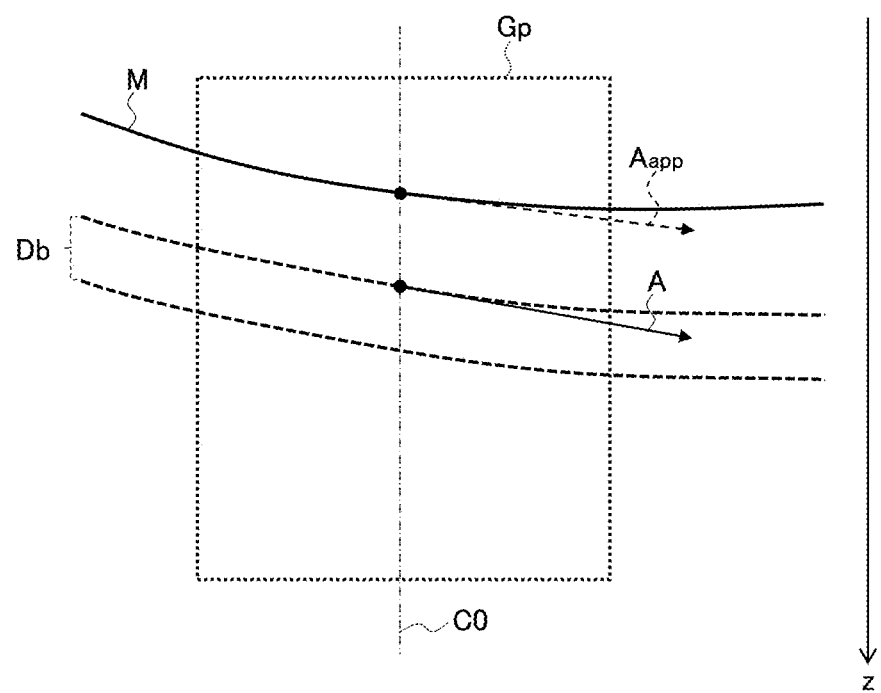
FIG. 18B is a schematic diagram for describing an example of the operation of the blood flow measurement apparatus according to the embodiment.

Note that the gradient A shown in FIG. 18A and the gradient A shown in FIG. 18B are vectors representing the orientation of the blood vessel of interest db, and the definition of such vector values may be arbitrary. As an example, the value of the gradient A may be defined to be the angle formed by the gradient (vector) A and the z axis. Similarly, the gradient $A_{app}$ shown in FIG. 18B is a vector representing the orientation of the inner limiting membrane region M, and the definition of the value of the vector may be arbitrary. For example, the value of the gradient $A_{app}$ may be defined to be the angle formed by the gradient (vector) $A_{app}$ and the z axis. Note that the direction of the z axis is substantially the same as the incident direction of the measurement light LS.

In the third example of the gradient estimation of the blood vessel of interest, the gradient estimator 233 may analyze the supplementary cross sectional image Gp shown in FIG. 18B to identify an image region corresponding to the blood vessel of interest db, and then calculate the gradient of the identified image region at the position corresponding to the cross section of interest C0. In such processing, the gradient estimator 233 may, for example, apply curve fitting to the boundary or the central axis of the image region corresponding to the blood vessel of interest db, and then determine the gradient of the approximate curve, obtained by the curve fitting, at the position corresponding to the cross section of interest C0. A similar curve fitting technique may be applied to the image region corresponding to the predetermined tissue of the fundus Ef described above (e.g., the inner limiting membrane region M).

The processing executed by the gradient estimator 233 is not limited to the above processing examples, and may be any processing capable of deriving an estimated value of the gradient of the blood vessel of interest db (e.g., a gradient value of the blood vessel of interest db itself, a value approximating the gradient of the blood vessel of interest db) based on cross sectional data acquired by applying OCT scanning to a cross section of the fundus Ef.

<Blood Flow Velocity Calculator 234>

Based on the temporal change in phase difference obtained as a phase image, the blood flow velocity calculator 234 calculates the blood flow velocity (or blood flow rate) at the cross section of interest C0 for blood flowing in the blood vessel of interest db. A parameter obtained by this calculation may be blood flow velocity at a certain time point, or may be a temporal change in blood flow velocity. The temporal change in blood flow velocity is referred to as blood flow velocity variation information. When blood flow velocity at a certain time point is to be determined, the blood flow velocity at a predetermined time phase in an electrocardiogram (e.g., a time phase corresponding to the R wave) may be selectively acquired, for example. When blood flow velocity variation information is to be determined, a time period during which blood flow velocity is measured is the whole or an arbitrary part of the time period taken for OCT scanning of the cross section of interest C0.

When the blood flow velocity variation information is acquired, the blood flow velocity calculator 234 may further calculate a statistic of the blood flow velocity in the measurement period. Examples of the statistic include the mean value, the standard deviation, the variance, the median, the mode, the global maximum, the global minimum, the local maximum, and the local minimum. The blood flow velocity calculator 234 may create a histogram on the blood flow velocity values.

The blood flow velocity calculator 234 calculates the blood flow velocity using Doppler OCT technique. In the blood flow velocity calculation, the gradient A (or its approximate value $A_{app}$) of the blood vessel of interest db at the cross section of interest C0 calculated by the gradient estimator 233 is taken into account. More specifically, the blood flow velocity calculator 234 may be configured to use the following relationship.

$$\Delta f = \frac{2nv\cos\theta}{\lambda} \quad \text{[Equation 3]}$$

Here: $\Delta f$ denotes the Doppler shift given to scattered light of the measurement light LS; n denotes the refractive index of medium; v denotes the flow velocity of the medium (blood flow velocity); $\theta$ denotes the angle between projection direction of the measurement light LS and the flow vector of the medium; and $\lambda$ denotes the center wavelength of the measurement light LS.

In the present embodiment, n and $\lambda$ are known, $\Delta f$ is derived from the temporal change of the phase difference, and $\theta$ is derived from the gradient A (or, from the approximate gradient value $A_{app}$). In some typical examples, $\theta$ is equal to the gradient A (or, to the approximate gradient value $A_{app}$). Substituting these values into the above equation yields the blood flow velocity v.

<Blood Vessel Diameter Calculator 235>

The blood vessel diameter calculator 235 calculates the diameter of the blood vessel of interest db at the cross section of interest C0. Examples of the blood vessel diameter calculation include the first calculation method on the basis of a fundus image (a front image of an eye fundus) and the second calculation method on the basis of a cross sectional image.

When applying the first calculation method, an area of the fundus Ef including the location of the cross section of interest C0 is photographed in advance. A fundus image thus obtained may be an observation image (e.g., a frame(s) thereof), or may be a photographed image. When the photographed image is a color image, any image obtained from the color image (e.g., a red-free image) may be used. The photographed image may be a fluorescence image obtained by fundus fluorescence angiography (e.g., fluorescein angiography), or may be a blood vessel emphasized image obtained by OCT angiography. An image created using OCT angiography is also referred to as an angiogram or a motion contrast image.

The blood vessel diameter calculator 235 sets a scale for fundus images based on various kinds of factors used to determine the relationship between the scale for images and the scale in the real space. Examples of such factors include the photographing angle of view (photographing magnification), the working distance, and information on an ocular optical system. The scale for fundus images may represent a length in the real space. As a specific example, the scale for fundus images may be configured to associate interval between adjacent pixels with a scale (distance) in the real space (e.g., pixel interval=10 μm). Note that it is possible to determine, in advance, the relationship between various values of the above factors and scales (values) in the real space, and then store a table or a graph that represents the relationship determined. In this case, the blood vessel diameter calculator 235 may select, from the table or the graph, a scale corresponding to the above factors and adopt the scale selected.

Based on the scale and the pixels included in the blood vessel region V0, the blood vessel diameter calculator 235 calculates the diameter of the blood vessel of interest db at the cross section of interest C0, that is, the diameter of the blood vessel region V0. As a specific example, the blood vessel diameter calculator 235 may calculate the maximum or the mean value of a plurality of diameters of the blood vessel region V0 corresponding to different directions. In some other examples, the blood vessel diameter calculator 235 may determine an approximate circle or an approximate ellipse of the contour of the blood vessel region V0, and then calculate the diameter of the approximate circle or the approximate ellipse. Note that once the blood vessel diameter of the blood vessel region V0 is determined, the area of the blood vessel region V0 can (substantially) be calculated. That is, it is possible to substantially associate blood vessel diameters with blood vessel areas in a one-to-one fashion. Therefore, an area of a blood vessel may be calculated in place of a diameter of the blood vessel.

The second calculation method will be described. In the second calculation method, typically, a cross sectional image at the cross section of interest C0 is used. The cross sectional image may be a main cross sectional image or any other image.

The scale of the cross sectional image is determined based on OCT measurement conditions. In the present embodiment, the cross section of interest C0 is scanned as shown in FIG. 17A or FIG. 17B. The length of the cross section of interest C0 is determined based on various kinds of factors that define the relationship between the scale of an image and the scale in the real space such as the working distance and information about ocular optical system. The blood vessel diameter calculator 235, for example, determines the interval between adjacent pixels based on the length of the cross section of interest C0, and calculates the diameter of the blood vessel of interest db at the cross section of interest C0 in the same manner as in the first calculation method.

<Blood Flow Amount Calculator 236>

Based on the calculation result of the blood flow velocity and the calculation result of the blood vessel diameter, the blood flow amount calculator 236 calculates a flow amount (or, flow volume) of blood that flows in the blood vessel of interest db. An example of the blood flow amount calculation will be described below.

It is assumed that the blood flow in a blood vessel is the Hagen-Poiseuille flow. The blood vessel diameter is denoted by w, and the maximum blood flow velocity is denoted by Vm. Then, the blood flow amount Q is expressed as in the following equation.

$$Q = \frac{\pi w^2}{8} Vm \qquad \text{[Equation 4]}$$

The blood flow amount calculator 236 substitutes the blood vessel diameter w calculated by the blood vessel diameter calculator 235 and the maximum blood flow velocity Vm based on the blood flow velocity calculated by the blood flow velocity calculator 234 into the above equation, thereby determining the targeted blood flow amount Q.

<Cross Section Setting Unit 237>

The main controller 211 displays a front image of the fundus Ef on the display 241. The front image may be any type of image, and may be any of an observation image, a photographed image, a fluorescence image, an OCT angiography image, an OCT projection image, and an OCT shadowgram.

The user operates the operation device 242 to designate one or more cross sections of interest in the displayed front image of the fundus Ef. Each cross section of interest is designated to intersect a blood vessel of interest. Based on the designated one or more cross sections of interest and the front image of the fundus Ef, the cross section setting unit 237 may set one or more supplementary cross sections for each of the one or more cross sections of interest. Note that a supplementary cross section may be set manually.

In another example, the cross section setting unit 237 may be configured to analyze a front image of the fundus Ef to identify one or more blood vessels of interest. The identification of the blood vessels of interest is performed based on, for example, the thickness of a blood vessel, the positional relationship between a blood vessel of interest and a predetermined site of a fundus (e.g., the optic nerve head, the macula), the type of a blood vessel (e.g., artery or vein), or the like. In addition, the cross section setting unit 237 may set one or more cross sections of interest and one or more supplementary cross sections, for each of the one or more blood vessels of interest identified.

In this manner, a cross section of interest and a supplementary cross section as illustrated in FIG. 17A or FIG. 17B are set with respect to the fundus Ef by the user, by the cross section setting unit 237, or by the cooperation between the user and the cross section setting unit 237.

<Movement Condition Setting Unit 260A>

As described above, in order to obtain optimum Doppler signals for eye fundus blood flow measurements, it is necessary to make the measurement light LS enter at an appropriate angle with respect to the running direction (the blood flow direction) of the blood vessel of interest. In the present embodiment, this is realized by shifting (or, moving, deviating, or displacing) the optical axis of the optical system (the optical axis of the objective lens 22) with respect to the optical axis of the subject's eye E. The movement condition setting unit 260A sets the movement condition of the optical system with respect to the optical axis of the subject's eye E. The movement condition setting unit 260A includes the direction setting unit 261 and the distance setting unit 262.

<Direction Setting Unit 261>

The direction setting unit 261 analyzes an OCT image of the fundus Ef to set a movement direction of the optical system. Note that as will be described below, the direction setting unit 261 may execute the same or similar processing as or to another element such as the blood vessel region identifying unit 231 or the gradient estimator 233. If this is the case, the direction setting unit 261 may have that function separately from the corresponding element, may use a result of processing executed by the corresponding element, may request the corresponding element to perform the processing instead, or may include the corresponding element. It should be noted that detailed descriptions will not be provided again for the same or similar processes as or to those executed by other elements among the processes executable by the direction setting unit 261.

The movement direction set by the direction setting unit 261 is a direction orthogonal to the optical axis of the optical system. Here, the optical axis of the optical system corresponds to the optical axis of the measurement arm and the optical axis of the objective lens 22. In other words, the movement direction set by the direction setting unit 261 is a direction defined in the xy plane and has only one of the x direction component and the y direction component. Alternatively, the movement direction set by the direction setting unit 261 has only both of the x direction component and the y direction component. In short, the movement direction set by the direction setting unit 261 has no z direction component.

In some typical examples, the movement direction set by the direction setting unit 261 is the movement direction applied to the first movement of the optical system (initial movement direction). Note that the direction setting unit 261 may be capable of setting the movement direction applied to the second (or, the third or subsequent) movement of the optical system.

The OCT image analyzed by the direction setting unit 261 may be any kind of OCT image. For example, the direction setting unit 261 may be configured to set the initial movement direction by analyzing at least two cross sectional images of the main cross sectional image G0, the supplementary cross sectional image G1, and the supplementary cross sectional image G2 shown in FIG. 18A. More generally, the direction setting unit 261 may be configured to set the initial movement direction by analyzing two or more cross sectional images constructed by applying an OCT scan to each of two or more cross sections each of which intersects the blood vessel of interest.

In some other examples, the direction setting unit 261 may be configured to set the initial movement direction by analyzing the supplementary cross sectional image Gp shown in FIG. 18B. More generally, the direction setting unit 261 may be configured to set the initial movement direction by analyzing a cross sectional image constructed by applying an OCT scan to a cross section lying along the blood vessel of interest. Note that OCT images analyzed for the setting of the initial movement direction is not limited to these examples.

As a first example, a case will be described of analyzing at least two cross sectional images among the main cross sectional image G0, the supplementary cross sectional image G1, and the supplementary cross sectional image G2 shown in FIG. 18A in order to set the initial movement direction of the optical system. Although the present example is configured to analyze the combination of the supplementary cross sectional image G1 and the supplementary cross sectional image G2, similar analysis may be performed on other combinations of images to be analyzed.

In the present example, the direction setting unit 261 analyzes the supplementary cross sectional image G1 to identify the blood vessel region V1, and analyzes the supplementary cross sectional image G2 to identify the blood vessel region V2. Next, the direction setting unit 261 identifies a feature position from each of the two blood vessel regions V1 and V2 identified, and derives an estimated value of the gradient of the blood vessel of interest db from the difference between the z coordinate values of the two feature positions identified. The direction setting unit 261 may set the initial movement direction of the optical system based on the estimated value of the gradient of the blood vessel of interest db derived in this manner.

In some modifications of the first example, the direction setting unit 261 may be configured to set the initial movement direction of the optical system based on the difference between the z coordinate values of the two feature positions identified from the two blood vessel regions V1 and V2 respectively.

In some other modifications of the first example, the direction setting unit 261 analyzes the supplementary cross sectional image G1 to identify an inner limiting membrane region, and also analyzes the supplementary cross sectional image G2 to identify an inner limiting membrane region. Next, the direction setting unit 261 identifies a feature position from each of the two inner limiting membrane regions identified. Here, each of the feature positions thus identified may be, for example, a position directly above the blood vessel of interest db. The direction setting unit 261 may set the initial movement direction of the optical system based on the difference between the z coordinate values of the two feature positions identified. Alternatively, the direction setting unit 261 may set the initial movement direction of the optical system based on an estimated value of the gradient of the blood vessel of interest db calculated from the difference between the z coordinate values of the two feature positions identified.

As a second example, a case will be described of analyzing the supplementary cross sectional image Gp shown in FIG. 18B in order to set the movement direction of the optical system.

In the present example, the direction setting unit 261 analyzes the supplementary cross sectional image Gp to identify the inner limiting membrane region M. Next, the direction setting unit 261 obtains an estimated value of the gradient of the blood vessel of interest db based on the inner limiting membrane region M identified. The direction setting unit 261 may set the initial movement direction of the optical system based on the estimated value of the gradient of the blood vessel of interest db.

In some modifications of the second example, the direction setting unit 261 analyzes the supplementary cross sectional image Gp to identify a blood vessel region corresponding to the blood vessel of interest db. Next, the direction setting unit 261 obtains an estimated value of the gradient of blood vessel of interest db based on the blood vessel region identified. The direction setting unit 261 may set the initial movement direction of the optical system based on the estimated value of the gradient of the blood vessel of interest db.

Figure 19A:
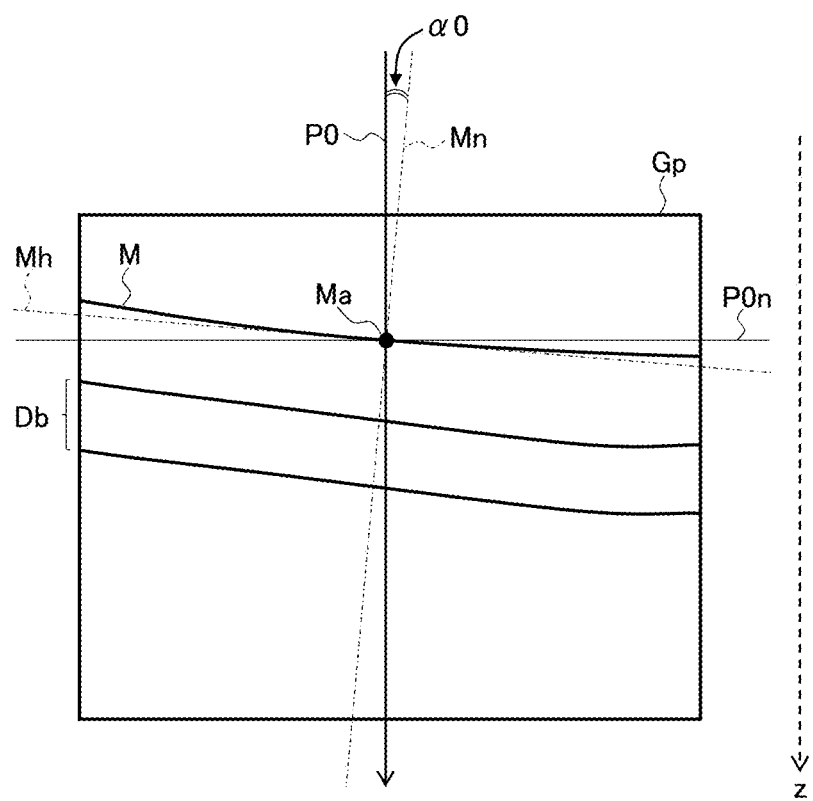
FIG. 19A is a schematic diagram for describing an example of the operation of the blood flow measurement apparatus according to the embodiment.
Figure 19B:
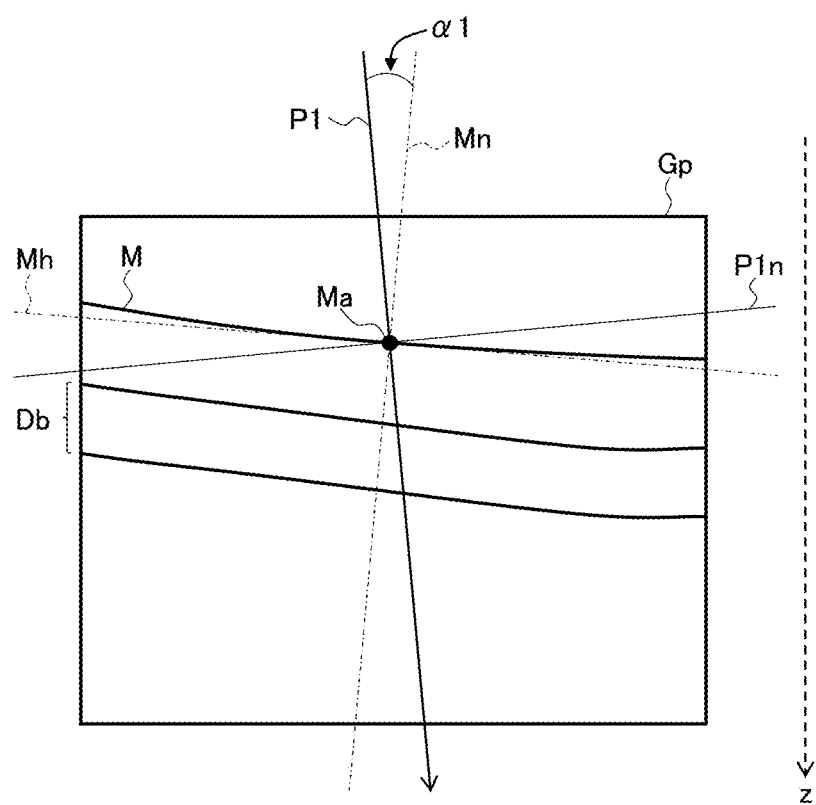
FIG. 19B is a schematic diagram for describing an example of the operation of the blood flow measurement apparatus according to the embodiment.

The process of setting the initial movement direction based on the gradient of the blood vessel of interest db will be described. The same or similar processing can be applied to any parameter equivalent to the gradient of the blood vessel of interest db. Examples of such a parameter include the followings: the gradient of the inner limiting membrane region M; the difference in the z coordinate values of the blood vessel regions in two or more cross sections of the blood vessel of interest db; and the difference in the z coordinate values of the inner limiting membrane regions in the two or more cross sections of the blood vessel of interest db. FIG. 19A and FIG. 19B are referred to in the following description.

The blood vessel of interest db and the inner limiting membrane (inner limiting membrane region M) are depicted in the supplementary cross sectional image Gp shown in FIG. 19A. The reference character Ma denotes the crossing position (intersection) of the inner limiting membrane region M and the cross section of interest C0 (see FIG. 18B etc.). The crossing position Ma corresponds to the position at which the gradient of the inner limiting membrane region M is calculated (the position at which the estimated gradient value of the blood vessel of interest db is calculated). The straight line denoted by the reference character Mh is a line indicating the slanted direction of the inner limiting membrane region M at the gradient calculation position Ma. The line Mh is referred to as a slanted line. The straight line denoted by the reference character Mn is a line indicating the normal direction of the slanted line Mh at the gradient calculation position Ma. The line Mn is referred to as a slanted normal line.

The straight line denoted by the reference character P0 is the path (a scan position) of the measurement light LS before the movement of the optical system (an initial position). The initial position of the optical system corresponds to, for example, a state where the alignment matches with the center of the pupil of the subject's eye E, in other words, a state where the optical axis of the optical system (the optical axis of the objective lens 22) passes through the center of the pupil of the subject's eye E. In the present example, the measurement path P0 passes through the gradient calculation position Ma and is parallel to the z direction. The straight line denoted by reference character P0$n$ is a line indicating the normal direction of the measurement path P0 at the gradient calculation position Ma. The line P0$n$ is referred to as a measurement normal line.

The angle formed by the measurement path P0 and the slanted normal line Mn is denoted by $\alpha 0$. The angle $\alpha 0$ is the incident angle of the measurement light LS with respect to the inner limiting membrane of the subject's eye E when the optical system is located at the initial position. That is, the angle $\alpha 0$ is used as the incident angle of the measurement light LS with respect to the blood vessel of interest db when the optical system is located at the initial position. It should be noted that the angle formed by the measurement normal line P0$n$ and the slanted line Mh is also $\alpha 0$.

The gradient of the blood vessel of interest db may be defined by the angle "α" formed by the measurement path and the slanted normal line, or by the angle "α" formed by the measurement normal line and the slanted line. Alternatively, the gradient of the blood vessel of interest db may be defined by the angle "90 degrees−α" formed by the measurement path and the slanted line, or the angle "90 degrees−α" formed by the measurement normal line and the slanted normal line. A range of an angle appropriate for the blood flow measurement (referred to as a target angle range) is set to, for example, "α=5 degrees to 10 degrees", that is, "90 degrees−α=80 degrees to 85 degrees". Here, the angle "α" is the incident angle of the measurement light LS with respect to the inner limiting membrane (the blood vessel of interest db). Further, the complementary angle "90 degrees−α" of the angle "α" is represented by "β".

The direction setting unit 261 sets the movement direction of the optical system so that the incident angle α is included in the target angle range (e.g., α=5 degrees to 10 degrees). As a condition equivalent to this, the direction setting unit 261 sets the movement direction of the optical system so that the complementary angle β is included in the target angle range (e.g., β=80 degrees to 85 degrees).

As is clear from FIG. 19 of Japanese Unexamined Patent Application Publication No. 2017-42602 (Patent Document 1), if the incident angle α=α0 shown in FIG. 19A is smaller than the target angle range, the direction setting unit 261 sets the movement direction of the optical system so that the incident angle α is included in the target angle range, that is, so that the incident angle α becomes larger. The movement direction set in such a case is the left direction in FIG. 19A. As a result, for example, as shown in FIG. 19B, scanning may be performed on the cross section of interest C0 with the measurement light LS that passes through the measurement path P1 in which the incident angle α=α1 (α1>α0). Here, the straight line denoted by the reference character P1*n* is a line indicating the normal direction of the measurement path P1 (the measurement normal line) at the gradient calculation position Ma.

On the contrary, if the incident angle α=α0 is larger than the target angle range, the direction setting unit 261 sets the movement direction of the optical system so that the incident angle α falls within the target angle range, that is, so that the incident angle α becomes smaller. The movement direction set in such a case is the right direction in FIG. 19A. Although illustration is omitted, such movement of the optical system allows performing scanning on the cross section of interest C0 with the measurement light LS that passes through the measurement path P2 in which the incident angle α=α2 (α2<α0).

<Distance Setting Unit 262>

As mentioned above, the optical system is moved in the initial movement direction set by the direction setting unit 261. The movement distance (an initial movement amount) in this movement may be set in advance. In the present embodiment, the initial movement amount is set by the distance setting unit 262. Note that the distance setting unit 262 may be capable of setting the movement amount applied to the second (or, the third or subsequent) movement of the optical system.

The first example of processing executable by the distance setting unit 262 will be described. The distance setting unit 262 in the present example may set the initial movement amount according to the actual pupil diameter of the subject's eye E.

Information indicating the pupil diameter of the subject's eye E (pupil diameter information) is acquired by the pupil diameter information acquiring unit. For example, the pupil diameter information acquiring unit includes an element for measuring the pupil diameter of the subject's eye E. As a specific example thereof, the pupil diameter information acquiring unit may include a processor configured and programmed to analyze an anterior eye segment image of the subject's eye E acquired by the illumination optical system 10 and the photographing optical system 30 to identify a pupil region, and then calculate the diameter of the pupil region. The identification of the pupil region may include a process such as thresholding and/or edge detection. The calculation of the diameter of the pupil region may include a process such as an approximation by ellipse and/or an approximation by circle.

The pupil diameter information acquiring unit may be configured to acquire, from the electronic medical record of the subject, a measured value of the pupil diameter of the subject's eye E acquired in the past. The pupil diameter information acquiring unit of the present example includes a communication device (the data input and output unit 290) for accessing an apparatus in which the electronic medical records or the like are stored.

The distance setting unit 262 may set the initial movement amount based on the value of the pupil diameter acquired by the pupil diameter information acquiring unit. For example, the distance setting unit 262 may set, as the initial movement amount, a value that is a half of the value of the pupil diameter acquired by the pupil diameter information acquiring unit. Such an initial movement amount corresponds to the value of the radius of the pupil of the subject's eye E or its approximate value.

According to the present example, the initial movement amount can be set based on the actual measured value of the pupil diameter of the subject's eye E. Therefore, the time required for achieving an optimum shift position can be shortened in the offset operation of the measurement arm for obtaining optimum Doppler signals for the eye fundus blood flow measurement. This leads to reduction of the burden on the subject.

The second example of processing executable by the distance setting unit 262 will be described. In the cases where the subject's eye E has a small pupil or cataract, or where the blood vessel of interest is located in the peripheral part of the fundus Ef, a drug (a mydriatic agent) may be administered to the subject's eye E for dilating the pupil in some cases. The distance setting unit 262 of the present example may set the initial movement amount according to whether or not the mydriatic agent has been administered to the subject's eye E.

The distance setting unit 262 of the present example stores, in advance, the first initial movement amount and the second initial movement amount. The first initial movement amount is an initial movement amount applied to the cases where the mydriatic agent is not administered and the second initial movement amount is a movement distance applied to the cases where the mydriatic agent is administered. The first initial movement amount is set to a value that is a half of a standard pupil diameter (the radius of a pupil of a standard size), for example. The second initial movement amount is set to a value that is a half of the diameter of a dilated pupil after the mydriatic agent has been administered to an eye having a standard pupil diameter. Note that an initial movement amount(s) according to the attributes (age, sex, etc.) of subjects or an initial movement amount(s) according to the attributes of subject's eye may be stored in advance.

The fact whether or not the mydriatic agent has been administered to the subject's eye E may be input by the user using the operation device 242, for example. Alternatively, the fact whether or not the mydriatic agent has been administered to the subject's eye E may be determined by referring to the electronic medical record of the subject via the data input and output unit 290.

The distance setting unit 262 may select one of a plurality of stored initial movement amounts based on information indicating whether or not the mydriatic agent has been administered to the subject's eye E.

According to the present embodiment, the initial movement amount may be set according to the size of the pupil of the subject's eye E (in particular, the pupil diameter according to whether or not the mydriatic agent has been administered). Therefore, the time required for achieving an optimum shift position can be shortened in the offset operation of the measurement arm for obtaining optimum Doppler signals for the eye fundus blood flow measurement. As a result of this, the burden on the subject can be reduced.

<Vignetting Judging Unit 270>

The vignetting judging unit 270 judges (determines) occurrence (presence or absence) of vignetting based on a detection result of the return light of the light incident on the subject's eye E through the optical system provided in the blood flow measurement apparatus 1A.

The type, purpose, and intensity (amount) of the light incident on the subject's eye E for the vignetting judgement may be arbitrary. The type of the incident light may be infrared light or visible light, for example. The purpose of the incident light may be, for example, imaging, examination, or measurement.

The incident light that can be employed for the present embodiment may be, for example, the measurement light LS for OCT scanning, or the observation illumination light, the photographing illumination light or excitation light for fundus imaging. The detection result of the return light of the incident light may be, for example, an OCT reflection intensity profile, an OCT image, an observation image, a photographed image, or a fluorescence image.

The "vignetting" in the present embodiment includes vignetting (decrease in brightness) that occurs when part or all of incident light for the eye fundus blood flow measurement or the return light of the incident light is blocked by the pupil. The "occurrence of vignetting" in the present embodiment includes any of the following: whether or not vignetting occurs; whether or not the degree of vignetting exceeds a predetermined level.

Examples of the processing executed by the vignetting judging unit 270 will be described. The first example and the second example will be described below regarding the vignetting judgement methods and techniques. However, the methods and techniques of judging the occurrence of vignetting are not limited thereto.

In the first example, the incident light for the vignetting judgement is the measurement light LS, and a predetermined OCT scan is applied. For example, the mode of the OCT scan in the present example may be an OCT scan for the cross section of interest C0 (or for the supplementary cross section C1 and/or for the supplementary cross section C2) shown in FIG. 17A. As an alternative, the mode of the OCT scan may be an OCT scan for the supplementary cross section Cp shown in FIG. 17B. The OCT scan in the present example is repetitive scanning for the same cross section, for example.

When applying the repetitive scanning to the supplementary cross section Cp (or, to the supplementary cross section C1 and/or to the supplementary cross section C2), the gradient estimation of the blood vessel of interest db may be performed in parallel with the vignetting judgement. Alternatively, when applying the repetitive scanning to the supplementary cross section Cp (or, to the supplementary cross section C1 and/or to the supplementary cross section C2), a smooth transition from the vignetting judgement to the gradient estimation of the blood vessel of interest db is possible. Further, the setting of the movement condition (the setting if the movement direction, the setting of the movement distance) may be performed in parallel with the vignetting judgement.

Figure 20A:
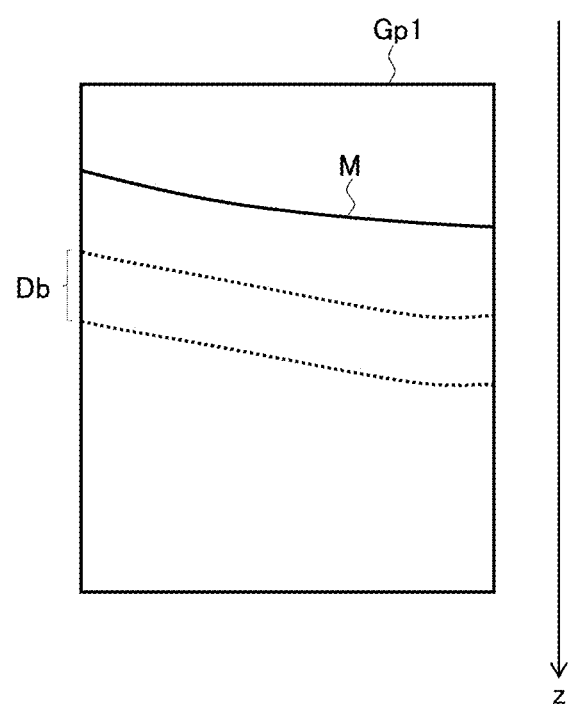
FIG. 20A is a schematic diagram for describing an example of the operation of the blood flow measurement apparatus according to the embodiment.
Figure 20B:
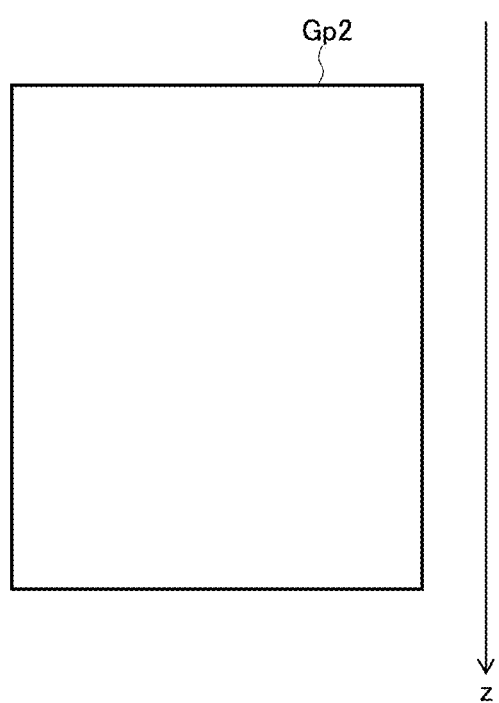
FIG. 20B is a schematic diagram for describing an example of the operation of the blood flow measurement apparatus according to the embodiment.

In the cases where the supplementary cross section Cp is employed to be subjected to the repetitive scanning and if there is no occurrence of vignetting, the cross sectional image Gp1 (cross sectional data) is obtained. The cross sectional image Gp1 represents the morphology (or structure) of the supplementary cross section Cp as shown in FIG. 20A. On the other hand, if there is occurrence of vignetting, the cross sectional image Gp2 (cross sectional data) is obtained in which the morphology (or structure) of the supplementary cross section Cp is not depicted as shown in FIG. 20B. Note that, in a state where the alignment is appropriate, the optical scanner 44 is placed at a position substantially conjugate with the pupil of the subject's eye E, and thus the deflection center (pivot) of the measurement light LS substantially coincides with the pupil. Therefore, when the vignetting of the measurement light LS occurs on the pupil, the cross sectional image Gp2 (cross sectional data) is obtained in which the morphology (or structure) of the supplementary cross section Cp is not depicted.

The vignetting judging unit 270 analyzes the cross sectional image obtained through the OCT scan for the supplementary cross section Cp and judges whether or not the morphology (or structure) of the supplementary cross section Cp is depicted. For example, the vignetting judging unit 270 may be configured to judge whether or not the inner limiting membrane region (M) is depicted in the cross sectional image. The judgement result that "the inner limiting membrane region is depicted in the cross sectional image" corresponds to the judgement result that "vignetting does not occur (or no occurrence of vignetting)". On the contrary, the judgement result that "the inner limiting membrane region is not depicted in the cross sectional image" corresponds to the judgement result that "vignetting occurs (or occurrence of vignetting)".

The second example of the processing executed by the vignetting judging unit 270 will be described. In the present example, the incident light for the vignetting judgement is the illumination light for fundus photography (fundus imaging). The incident light may also be the observation illumination light or the photographing illumination light. The vignetting judging unit 270 analyzes a fundus image to judge whether or not a decrease in light amount attributable to the vignetting has occurred. For example, the vignetting judging unit 270 judges whether or not there is a difference between the brightness of the central part of the fundus image and the brightness of the peripheral part of the fundus image. More specifically, the vignetting judging unit 270 judges whether or not the light amount in the peripheral part of the fundus has decreased. Such a judgement on the decrease in the light amount is performed with reference to the values of the pixels that constitute the fundus image. In some typical examples, the values of the pixels here refer to the brightness distribution over the pixels. The judgement includes, for example, image processing such as thresholding and labeling.

According to the second example, the degree of vignetting may be easily judged. The degree of vignetting is evaluated based on, for example, the characteristics or features of the image region in which the peripheral light amount of the fundus image has decreased. The vignetting judging unit 270 may calculate an evaluation value in this way, and may judge the occurrence of vignetting based on the magnitude of the evaluation value. The evaluation value may be, for example, the size (area) of the region in which the peripheral light amount has decreased. The "occurrence (presence or absence) of vignetting" in the present example corresponds to, for example, whether or not the degree of vignetting exceeds a predetermined degree. In some typical examples, the vignetting judging unit 270 compares the calculated evaluation value with a threshold value and judges that "vignetting occurs" if the evaluation value exceeds the threshold value. If the evaluation value is less than or equal to the threshold value, the vignetting judging unit 270 judges that "no vignetting occurs".

The data processor 230 that functions as described above may include, for example, a processor, a RAM, a ROM, a hard disk drive, and the like. A storage device such as a hard disk drive may store, in advance, a computer program that causes the processor to execute the above functions.

<User Interface 240>

The user interface (UI) 240 includes the display 241 and the operation device 242. The display 241 includes the display 3 shown in FIG. 13 and/or another display device. The operation device 242 includes any types of operation devices. The user interface 240 may include, for example, a device having both a display function and an operation function, such as a touch panel.

<Data Input and Output Unit 290>

The data input and output unit (data I/O unit) 290 performs input of data into the blood flow measurement apparatus 1A and output of data from the blood flow measurement apparatus 1A.

The data input and output unit 290 has, for example, a function for communicating with external devices (not shown in the figures). The data input and output unit 290 with such a communication function includes a communication interface according to the form or aspect of connection with external devices. External devices may be, for example, one or more of any type of ophthalmic apparatus. Further, External devices may be one or more of any types of information processing devices such as a hospital information system (HIS) server, a digital imaging and communications in medicine (DICOM) server, a doctor's terminal, a mobile terminal, a personal terminal, a cloud server, and other devices.

The data input and output unit 290 may include a device that reads out information from a recording medium (i.e., a data reader device), and/or a device that writes or records information into a recording medium (i.e., a data writer device), for example.

<Operation>

Figure 21:
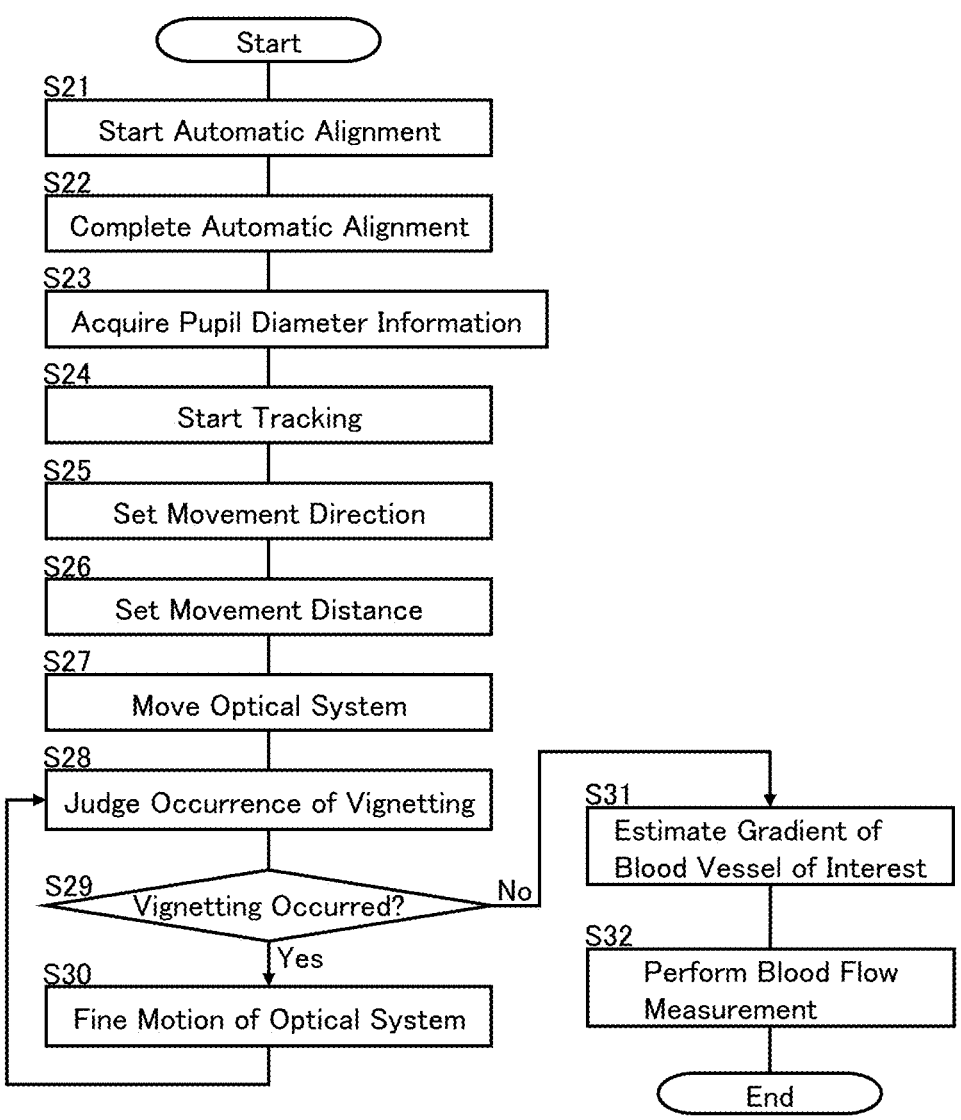
FIG. 21 is a flowchart showing an example of the operation of the blood flow measurement apparatus according to the embodiment.

An example of the operation of the blood flow measurement apparatus 1A will be described. FIG. 21 shows an example of the operation of the blood flow measurement apparatus 1A. It is assumed that preparatory processing such as input of the patient ID has already been performed.

(S1: Start Automatic Alignment)

First, the blood flow measurement apparatus 1A executes automatic alignment. The automatic alignment is performed using the alignment indicator as described above, for example. Alternatively, the automatic alignment may be performed using two or more anterior eye segment cameras, as disclosed in Japanese Unexamined Patent Application Publication No. 2013-248376. The method and technique of performing automatic alignment are not limited to these examples.

(S22: Complete Automatic Alignment)

The automatic alignment is completed when the relative position between the subject's eye E and the optical system matches with each other in all the x, y, and z directions.

(S23: Acquire Pupil Diameter Information)

The blood flow measurement apparatus 1A acquires the pupil diameter information of the subject's eye E by the pupil diameter information acquiring unit described above.

(S24: Start Tracking)

After the completion of the automatic alignment, the blood flow measurement apparatus 1A starts tracking in order to move the optical system in accordance with the movement of the subject's eye E (the fundus Ef). The tracking is carried out by the combination of the following operations, for example: an operation of acquiring an observation image of the fundus Ef using infrared light; an operation of analyzing the observation image to detect the movement of the fundus Ef; and an operation of moving the optical system in accordance with the movement of the fundus Ef detected. Further, the tracking may also include an operation of controlling the optical scanner 44 according to the movement of the fundus Ef.

Here, setting of the fundus imaging conditions such as focus adjustment with respect to the fundus Ef and setting of the OCT measurement conditions such as optical path length adjustment and focus adjustment may be performed. Further, the selection of a blood vessel of interest, the setting of a cross section of interest, the setting of a supplementary cross section, and the like may be executed at this stage or at any other timing. In the present operation example, it is assumed that the blood vessel of interest db, the cross section of interest C0, and the supplementary cross section Cp shown in FIG. 17B are set.

(S25: Set Movement Direction)

The blood flow measurement apparatus 1A applies an OCT scan to the supplementary cross section Cp. The direction setting unit 261 sets the movement direction (i.e., an initial movement direction) of the optical system (at least of the measurement arm) by analyzing the supplementary cross sectional image Gp that represents the supplementary cross section Cp.

(S26: Set Movement Distance)

The distance setting unit 262 sets the movement distance (i.e., an initial movement amount) of the optical system based on the pupil diameter information acquired in the step S23. Note that the distance setting unit 262 may set the movement distance according to whether or not the mydriatic agent has been administered to the subject's eye E.

(S27: Move Optical System)

At this stage, typically, the center of the pupil (or the corneal apex) and the optical axis of the optical system substantially match with each other in the xy directions as well as the distance between the subject's eye E and the optical system (the objective lens 22) in the z direction substantially matches with the working distance.

The main controller 211 controls the movement mechanism 150 to move the optical system in the initial movement direction set in the step S25 by the initial movement amount set in the step S26. In other words, the main controller 211 applies the first movement control to the movement mechanism 150 in order to move the optical system by the initial movement amount from the optical axis in the initial movement direction orthogonal to the optical axis of the optical system.

Figure 22A:
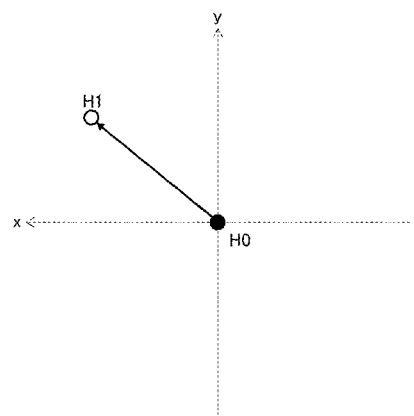
FIG. 22A is a schematic diagram for describing an example of the operation of the blood flow measurement apparatus according to the embodiment.

As a result of the first movement control, for example, as shown in FIG. 22A, the optical axis of the optical system is moved from the position H0 to the position H1. Here, the position H0 is a position that substantially coincides with the center of the pupil (or the corneal apex) in the xy directions while the position H1 is a position that is separated from the position H0 by a predetermined distance in the upper left direction.

In the present embodiment, the movement direction of the optical system in the first movement control (i.e., the initial movement direction) is set based on an OCT image of the fundus Ef. On the other hand, the movement distance of the optical system in the first movement control (i.e., the initial movement amount) may be any distance such as any of the followings, for example: a distance set based on the pupil diameter information and/or the fact whether or not the mydriatic agent is administered; and a distance set as a default.

(S28: Judge Occurrence of Vignetting)

After the first movement control (the first movement of the optical system) in the step S27, the main controller 211 starts the scanning of the supplementary cross section Cp shown in FIG. 17B. This scanning is employed as an OCT scan for the vignetting judgement. The vignetting judging unit 270 judges the occurrence of vignetting based on cross sectional data acquired by the OCT scan.

In some examples, the judgement of the occurrence of vignetting in the present step includes the following processes: the image constructing unit 220 (the cross sectional image constructing unit 221) constructs a cross sectional image from the data acquired by the OCT scan for the supplementary cross section Cp; and the vignetting judging unit 270 judges the occurrence of vignetting by determining whether or not the morphology (or structure) of the supplementary cross section Cp is depicted in the cross sectional image constructed.

(S29: Vignetting Occurred?)

If the vignetting judging unit 270 has judged in the step S28 that the vignetting has occurred (S29: Yes), the operation proceeds to the step S30. On the other hand, if the vignetting judging unit 270 has judged that the vignetting has not occurred (S29: No), the operation proceeds to the step S31.

(S30: Fine Motion of Optical System)

If the vignetting judging unit 270 has judged in the step S29 that the vignetting has occurred (S29: Yes), the main controller 211 applies the second movement control to the movement mechanism 150 in order to perform fine adjustment of the position of the optical system.

In some typical examples, the movement distance in the second movement control is shorter than the movement distance (the initial movement amount) in the first movement control in the step S27. In addition, the movement direction in the second movement control is opposite to the initial movement direction in the first movement control in the step S27. Here, the movement distance in the second movement control may be, for example, a distance set as a default or a distance set by the distance setting unit 262.

Figure 22B:
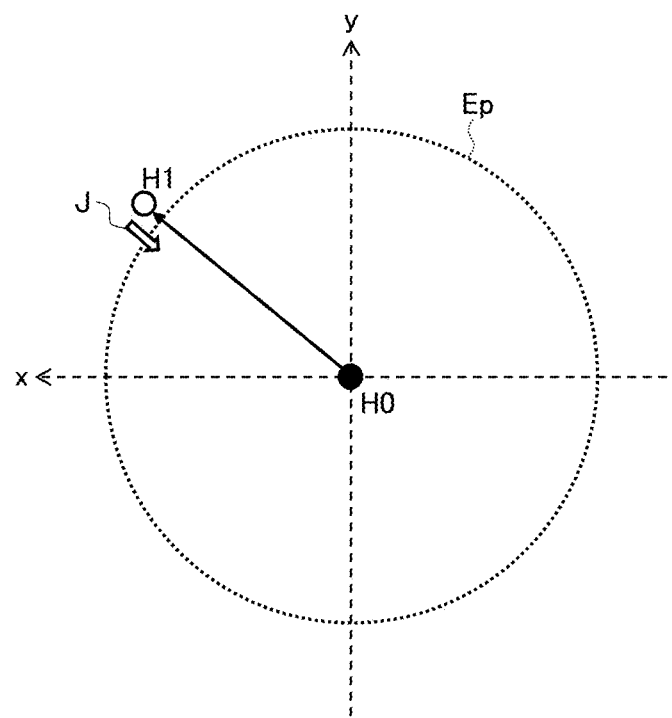
FIG. 22B is a schematic diagram for describing an example of the operation of the blood flow measurement apparatus according to the embodiment.

The case where the vignetting judging unit 270 judges in the step S29 that the vignetting has occurred will be described. As shown in FIG. 22B, for example, when the optical axis position H1 after the first movement control is located outside the pupil Ep, the measurement light LS is blocked by the iris or the like. In such a case, a cross sectional image is obtained in which the morphology (or structure) of the supplementary cross section Cp is not depicted, as shown in FIG. 20B. As a result of this, the vignetting judging unit 270 obtains a judgement result that the vignetting has occurred. As indicated by the reference character J in FIG. 22B, the main controller 211 controls the movement mechanism 150 to move the optical system in the direction opposite to the initial movement direction by a predetermined distance. Here, the initial movement direction is the direction from the position H0 to the position H1, and the predetermined distance is a predetermined amount of fine motion. In this way, when the vignetting judging unit 270 judges in the step S29 that the vignetting has occurred, the optical axis of the optical system is moved in the direction toward the optical axis position H0 that is the position of the optical axis immediately after the automatic alignment.

After the fine movement of the optical system has been performed, the process returns to the step S28. The steps S28 to S30 are repeated until the determination result becomes "Yes" in the step S29. Note that when the steps S28 to S30 have been repeated a predetermined number of times or when the steps S28 to S30 have been repeated for a predetermined period of time, the blood flow measurement apparatus 1A may output the determination indicating an error.

(S31: Estimate Gradient of Blood Vessel of Interest)

If the vignetting judging unit 270 judges in the step S29 that the vignetting has not occurred (S29: No), the blood flow measurement apparatus 1A performs the estimation of the gradient of the blood vessel of interest db in the manner as described above. For the gradient estimation of the present example, the cross sectional data of the supplementary cross section Cp may be used as in the vignetting judgement, for example.

Figure 22C:
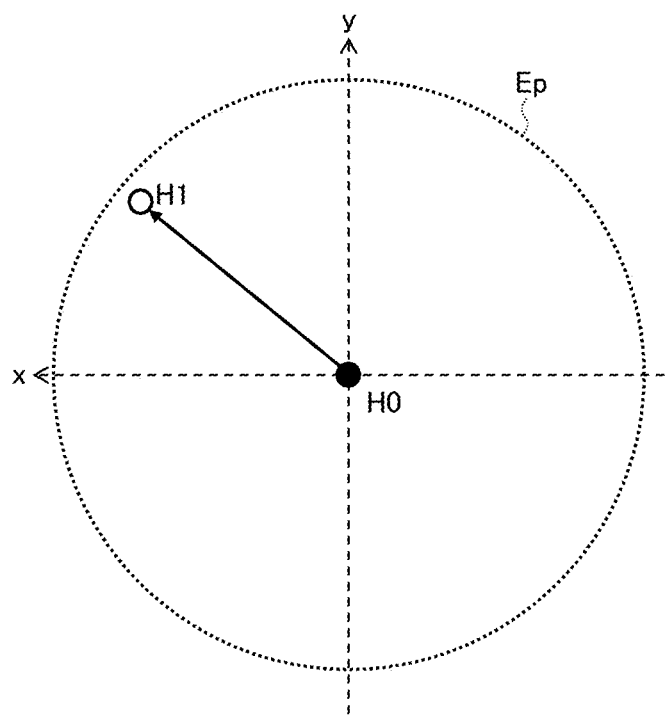
FIG. 22C is a schematic diagram for describing an example of the operation of the blood flow measurement apparatus according to the embodiment.

Note that if the vignetting judging unit 270 judges in the step S29 that the vignetting has not occurred, the optical axis position H1 after the first movement control is located inside the pupil Ep, as shown in FIG. 22C, for example.

(S32: Perform Blood Flow Measurement)

After the estimated value of the gradient of the blood vessel of interest db is obtained in the step S31, the blood flow measurement apparatus 1A performs the blood flow measurement on the cross section of interest C0 and then generates blood flow information in the same manner as described above. (End).

Some modification examples will be described of the operation described above. The main controller 211 may display the information indicating the initial movement direction set in the step S25 on the display device 241. Further, the main controller 211 may display the information indicating the initial movement amount set in the step S26 on the display device 241. Furthermore, the main controller 211 may display the information indicating the estimated value of the gradient obtained by the gradient estimator 233 on the display device 241. Moreover, the main controller 211 may display the information indicating the difference between the estimated value of the gradient and the target angle range on the display device 241.

As described above, the target angle range is set to a range of 80 degrees to 85 degrees, for example. The target angle range may be a single value or a range defined by an upper limit and/or a lower limit. The target angle range may be any of the followings, for example: a default value; a default range; a value or a range set by the user or another person (e.g., a maintenance service person); and a value or a range set by the blood flow measurement apparatus 1A or another apparatus (e.g., a server in a medical/health facility, and an apparatus that monitors the operation of the blood flow measurement apparatus 1A). Examples of ways of setting the target angle range, in the cases where the blood flow measurement apparatus 1A or the like set the target angle range, include the followings: setting once again the target angle range applied to the subject's eye E in the past; setting the target angle range according to the attributes of the subject; and setting the target angle range according to the attributes of the subject's eye E.

The user may refer to the displayed information and input an instruction regarding the movement direction or an instruction regarding the movement distance. These instructions are given, for example, when an appropriate measurement angle cannot be achieved even after the second movement control has been repeatedly performed.

<Actions and Effects>

Some actions and effects of the blood flow measurement apparatus according to the exemplary embodiment will be described.

The blood flow measurement apparatus (1) of the exemplary embodiment includes a scanning optical system, a movement mechanism, an image constructing unit, a direction setting unit, a controller, and a blood flow information acquiring unit.

The scanning optical system is configured to apply an OCT scan to a fundus of a subject's eye. In the present embodiment, the optical system that includes the OCT unit 100 and the measurement arm in the fundus camera unit 2 is an example of the scanning optical system.

The movement mechanism is configured to move the scanning optical system. The movement mechanism 150 of the present embodiment is an example of the movement mechanism.

The image constructing unit is configured to construct an image from first data acquired by the scanning optical system. The image constructed from the first data may be a reflection intensity profile or an image (image data) generated from the reflection intensity profile. The image constructing unit 220 of the present embodiment is an example of the image constructing unit.

The direction setting unit is configured to analyze the image constructed by the image constructing unit to set a first direction (an initial movement direction) orthogonal to an optical axis of the scanning optical system. The direction setting unit 261 of the present embodiment is an example of the direction setting unit.

The controller is configured to apply a first movement control to the movement mechanism to move the scanning optical system in the first direction. The controller 210 (the main controller 211) of the present embodiment is an example of the controller.

The blood flow information acquiring unit is configured to acquire blood flow information from second data acquired by the scanning optical system after the first movement control. The image constructing unit 220 and the data processor 230 (the blood vessel region identifying unit 231, the blood flow information generating unit 232) of the present embodiment are examples of the blood flow information acquiring unit.

In some exemplary embodiments, the scanning optical system may be configured to apply an OCT scan to a cross section lying along (oriented along) a blood vessel of interest of the fundus to acquire the first data. Further, the direction setting unit may be configured to analyze an image of the cross section constructed from the first data to set the first direction. The scanning optical system may apply an OCT scan to the blood vessel of interest to acquire the second data after the first movement control.

In some exemplary embodiments, the direction setting unit may be configured to analyze the image of the cross section lying along (oriented along) the blood vessel of interest to obtain an estimated value of gradient of the blood vessel of interest, and to set the first direction based on the estimated value of the gradient.

In some exemplary embodiments, the direction setting unit may be configured to analyze the image of the cross section lying along (oriented along) the blood vessel of interest to identify an image region corresponding to a surface of the fundus (an inner limiting membrane region), and to obtain the estimated value of the gradient based on the image region.

In some exemplary embodiments, the direction setting unit may be configured to analyze the image of the cross section lying along (oriented along) the blood vessel of interest to identify an image region corresponding to the blood vessel of interest, and obtains the estimated value of the gradient based on the image region.

In some exemplary embodiments, the direction setting unit may be configured to set the first direction so that an incident angle of OCT scan light with respect to the blood vessel of interest is included within a predetermined range.

In some exemplary embodiments, the controller may be configured to perform the first movement control to move the scanning optical system in the first direction by a distance (an initial movement amount) set in advance.

The blood flow measurement apparatus according to some exemplary embodiments may further include a pupil diameter information acquiring unit and a first setting unit. The pupil diameter information acquiring unit is configured to acquire pupil diameter information of the subject's eye. The first setting unit is configured to set the initial movement amount based on the pupil diameter information acquired. In the present embodiment, the illumination optical system 10, the photographing optical system 30, and the processor are examples of the pupil diameter information acquiring unit. Further, in the present embodiment, the data input and output unit 290 is another example of the pupil diameter information acquiring unit. In addition, the distance setting unit 262 of the present embodiment is an example of the first setting unit.

The blood flow measurement apparatus according to some exemplary embodiments may further include a second setting unit configured to set the initial movement amount according to whether or not a mydriatic agent has been administered to the subject's eye. The distance setting unit 262 of the present embodiment is an example of the second setting unit.

The blood flow measurement apparatus according to some exemplary embodiments may further include a judging unit configured to judge the occurrence of vignetting based on a detection result of return light of light incident on the subject's eye through the scanning optical system after the first movement control. Further, the controller may be configured to apply a second movement control to the movement mechanism to further move the scanning optical system according to a judgement result obtained by the judging unit. The vignetting judging unit 270 of the present embodiment is an example of the judging unit.

In some exemplary embodiments, the scanning optical system may be configured to apply an OCT scan to the fundus to acquire the second data if the judging unit has judged that the vignetting has not occurred. That is, the scanning optical system may be configured to apply the OCT scan to the fundus to acquire the second data without having to perform further movement control if the judging unit has judged that the vignetting has not occurred.

In some exemplary embodiments, the controller may be configured to apply the second movement control to the movement mechanism to move the scanning optical system in a second direction opposite to the first direction (the initial movement direction) by a distance shorter than a movement distance (the initial movement amount) in the first movement control if the judging unit has judged that the vignetting has occurred.

According to such an embodiment, in the offset operation of the optical system (the measurement arm) to obtain optimum Doppler signals for the eye fundus blood flow measurement, the blood flow measurement can be performed after the measurement arm has been shifted in the direction set based on an OCT image. Therefore, the offset direction (shift direction, movement direction) of the measurement arm with respect to the optical axis of the subject's eye can be set in an appropriate manner. In addition, the shift position of the incident light for measuring the fundus blood flow can be optimized.

According to the present embodiment, the shift position of the incident light for the eye fundus blood flow measurement can be optimized in an automatic fashion.

According to the present embodiment, information for assisting the user can be presented when part of the operation of optimizing the shift position of the incident light for the eye fundus blood flow measurement is performed in a manual fashion.

The embodiments described above are merely illustrative aspects of the implementation of the present invention. Therefore, any modifications (e.g., omission, substitution, replacement, addition, etc.) may be made within the scope of the present invention.

The invention claimed is:

1. A blood flow measurement apparatus comprising:
    a blood flow measuring unit that includes an optical system for applying an optical coherence tomography (OCT) scan to a fundus of a subject's eye, and processing circuitry that is configured to obtain blood flow information based on data acquired by the OCT scan;
    a movement mechanism including at least one actuator configured to move the optical system;
    a controller circuit configured to apply a first movement control to the movement mechanism to move the optical system in a first direction orthogonal to an optical axis of the optical system by a predetermined distance from the optical axis; and
    the processing circuitry further configured to judge occurrence of vignetting based on a detection result of return light of light incident on the subject's eye through the optical system after the first movement control and produce a vignetting judgment result,
    wherein the controller circuit applies a second movement control to the movement mechanism to further move the optical system based on Raphe vignetting judgement result.

2. The blood flow measurement apparatus of claim 1, wherein
    the optical system applies the OCT scan to a cross section along a blood vessel of interest of the fundus to acquire cross sectional data after the first movement control, and
    the processing circuitry is further configured to judge the occurrence of the vignetting and produce the vignetting judgement result based on the cross sectional data.

3. The blood flow measurement apparatus of claim 2, wherein the processing circuitry is further configured to obtain an estimated value of gradient of the blood vessel of interest based on the cross sectional data.

4. The blood flow measurement apparatus of claim 3, wherein the controller circuit displays the estimated value of the gradient obtained by the processing circuitry after the second movement control and a target value of gradient set in advance on a display device.

5. The blood flow measurement apparatus of claim 4, further comprising a user interface,
    wherein the controller circuit performs the first movement control again if the target value is changed using the user interface.

6. The blood flow measurement apparatus of claim 3, wherein the controller circuit controls the blood flow measuring unit to obtain the blood flow information if the estimated value of the gradient obtained by the processing circuitry after the second movement control substantially matches with a target value of gradient set in advance.

7. The blood flow measurement apparatus of claim 1, wherein
    the controller circuit performs the second movement control to further move the optical system in the first direction if the processing circuitry judges that the vignetting does not occur, and
    the controller circuit performs the second movement control to move the optical system in a direction opposite to the first direction if the processing circuitry judges that the vignetting occurs.

8. The blood flow measurement apparatus of claim 7, wherein the controller circuit repeatedly performs the second movement control until the processing circuitry judges that the vignetting does not occur and the optical system is located at a position in which a shift from a position of the optical axis immediately before the first movement control becomes maximum.

9. The blood flow measurement apparatus of claim 1, further comprising:
    an observation system configured to acquire an infrared observation image of the fundus; and
    the processing circuitry is further configured to evaluate the infrared observation image to produce an infrared evaluation result,
    wherein the controller circuit performs the second movement control based on the vignetting judgement result and the infrared evaluation result.

10. The blood flow measurement apparatus of claim 9, wherein
    the controller circuit performs the second movement control to further move the optical system in the first direction if the processing circuitry judges that the vignetting does not occur and the infrared evaluation result indicates that the infrared observation image is appropriate, and
    the controller circuit performs the second movement control to move the optical system in a direction opposite to the first direction if the processing circuitry judges that the vignetting occurs, or if the infrared evaluation result indicates that the infrared observation image is not appropriate.

11. The blood flow measurement apparatus of claim 10, wherein the controller circuit repeatedly performs the second movement control until the processing circuitry judges that the vignetting does not occur, the infrared evaluation result indicates that the infrared observation image is appropriate, and the optical system is located at a position in which a shift from a position of the optical axis immediately before the first movement control becomes maximum.

12. The blood flow measurement apparatus of claim 9, wherein the processing circuitry is further configured to detect movement of the fundus by analyzing the infrared observation image,
wherein the controller circuit applies tracking control to the movement mechanism to move the optical system according to movement of the fundus detected by the processing circuitry.

13. The blood flow measurement apparatus of claim 1, wherein the processing circuitry is further configured to set the predetermined distance used in the first movement control according to whether or not a mydriatic agent is administered to the subject's eye.

14. The blood flow measurement apparatus of claim 1,
wherein the processing circuitry is further configured to acquire a value of a pupil diameter of the subject's eye and set the predetermined distance used in the first movement control based on the value of the pupil diameter.

15. A blood flow measurement apparatus comprising:
a scanning optical system including an optical coherence tomography (OCT) scanner configured to scan a fundus of a subject's eye;
a movement mechanism including at least one actuator configured to move the scanning optical system;
processing circuitry configured to construct an image from first data acquired by the scanning optical system;
the processing circuitry further configured to analyze the image to set a first direction orthogonal to an optical axis of the scanning optical system;
a controller circuit configured to apply a first movement control to the movement mechanism to move the scanning optical system in the first direction; and
the processing circuitry is further configured to acquire blood flow information from second data acquired by the scanning optical system after the first movement control.

16. The blood flow measurement apparatus of claim 15, wherein
the scanning optical system applies an OCT scan to a cross section along a blood vessel of interest of the fundus to acquire the first data,
the processing circuitry analyzes an image of the cross section constructed from the first data to set the first direction, and
the scanning optical system applies an OCT scan to the blood vessel of interest to acquire the second data after the first movement control.

17. The blood flow measurement apparatus of claim 16, wherein the processing circuitry analyzes the image of the cross section to obtain an estimated value of gradient of the blood vessel of interest, and sets the first direction based on the estimated value of the gradient.

18. The blood flow measurement apparatus of claim 17, wherein the processing circuitry analyzes the image of the cross section to identify an image region corresponding to a surface of the fundus, and obtains the estimated value of the gradient based on the image region.

19. The blood flow measurement apparatus of claim 17, wherein the processing circuitry analyzes the image of the cross section to identify an image region corresponding to the blood vessel of interest, and obtains the estimated value of the gradient based on the image region.

20. The blood flow measurement apparatus of claim 16, wherein the processing circuitry sets the first direction so that an incident angle of OCT scan light with respect to the blood vessel of interest is included within a predetermined range.

21. The blood flow measurement apparatus of claim 15, wherein the controller circuit performs the first movement control to move the scanning optical system in the first direction by a distance set in advance.

22. The blood flow measurement apparatus of claim 21,
wherein the processing circuitry is further configured to acquire a value of a pupil diameter of the subject's eye and set the distance based on the pupil diameter information.

23. The blood flow measurement apparatus of claim 21, wherein the processing circuitry is further configured to set the distance according to whether or not a mydriatic agent is administered to the subject's eye.

24. The blood flow measurement apparatus of claim 15, wherein the processing circuitry is further configured to judge occurrence of vignetting based on a detection result of return light of light incident on the subject's eye through the scanning optical system after the first movement control and produce a vignetting judgment result,
wherein the controller circuit applies a second movement control to the movement mechanism to further move the scanning optical system according to the vignetting judgement result.

25. The blood flow measurement apparatus of claim 24, wherein the scanning optical system applies an OCT scan to the fundus to acquire the second data if the vignetting judgement result indicates that the vignetting does not occur.

26. The blood flow measurement apparatus of claim 24, wherein the controller circuit applies the second movement control to the movement mechanism to move the scanning optical system in a second direction opposite to the first direction by a distance shorter than a movement distance in the first movement control if the vignetting judgement result indicates that the vignetting occurs.

* * * * *